United States Patent [19]
Akahoshi et al.

[11] Patent Number: 5,948,785
[45] Date of Patent: Sep. 7, 1999

[54] HETEROCYCLIC AMIDE COMPOUNDS AND PHARMACEUTICAL USE OF THE SAME

[75] Inventors: Fumihiko Akahoshi; Takuya Yoshimura; Masahiro Eda; Atsuyuki Ashimori; Hajime Fukuyama; Masahide Nakajima; Teruaki Imada, all of Hirakata; Hideki Okunishi, Ohtsu; Mizuo Miyazaki, Nagaokakyo, all of Japan

[73] Assignee: The Green Cross Corporation, Osaka, Japan

[21] Appl. No.: 08/952,319

[22] PCT Filed: Apr. 26, 1996

[86] PCT No.: PCT/JP96/01171

§ 371 Date: Oct. 27, 1997

§ 102(e) Date: Oct. 27, 1997

[87] PCT Pub. No.: WO96/33974

PCT Pub. Date: Oct. 31, 1996

[30] Foreign Application Priority Data

Apr. 27, 1995 [JP] Japan ................................. 7-104314

[51] Int. Cl.[6] .......................... A61K 31/44; C07D 213/64
[52] U.S. Cl. ................... 514/269; 514/227.8; 514/235.8; 514/237.2; 514/255; 514/318; 514/349; 544/58.2; 544/58.4; 544/58.6; 544/60; 544/123; 544/131; 544/295; 544/319; 544/360; 546/193; 546/268.1; 546/276.4; 546/279.1; 546/297
[58] Field of Search .................................. 514/269, 349, 514/227.8, 235.8, 237.2, 255, 318; 544/319, 58.2, 58.4, 58.6, 60, 123, 131, 295, 360; 546/193, 268.1, 276.4, 279.1

[56] References Cited

FOREIGN PATENT DOCUMENTS 0528633  8/1992  European Pat. Off. .
0509769  10/1992  European Pat. Off. .
WO9321212  10/1993  WIPO .
WO9526958  10/1995  WIPO .

OTHER PUBLICATIONS

*Journal of Hypertension 1993*, vol. 11, No. 11, Nov. 1, 1993, pp. 1155–1159 "The chymase–angiotensin system in humans".

*European Heart Journal*, vol. 14, No. SUPPL. I, Jan. 1, 1993, pp. 177–182 "Cardiac angiotensin II formation: the angiotensin–I converting enzyme and human chymase".

*Primary Examiner*—Mukund J. Shah
*Assistant Examiner*—Brenda Coleman
*Attorney, Agent, or Firm*—Sughrue, Mion, Zinn, Macpeak & Seas, PLLC

[57] ABSTRACT

Heterocyclic amide compounds of the formula (I)

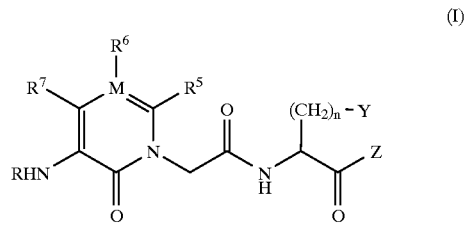

wherein each symbol is as defined in the specification, pharmacologically acceptable salts thereof, pharmaceutical compositions thereof and pharmaceutical use thereof. The heterocyclic amide compounds and pharmacologically acceptable salts thereof of the present invention have superior inhibitory activity against chymase groups in mammals inclusive of human, and can be administered orally or parenterally. Therefore, they are useful as chymase inhibitors and can be effective for the prophylaxis and treatment of various diseases caused by chymase, such as those caused by angiotensin II.

14 Claims, No Drawings

HETEROCYCLIC AMIDE COMPOUNDS AND PHARMACEUTICAL USE OF THE SAME

TECHNICAL FIELD

This application is a 371 of PCT/JP96/01171, filed Apr. 26, 1996.

The present invention relates to novel heterocyclic amide compounds, pharmacologically acceptable salts thereof, pharmaceutical compositions thereof and pharmaceutical use thereof. More particularly, the present invention relates to pyridone- and pyrimidoneacetamide derivatives which are useful pharmacologically, diagnostically and for the prophylaxis and treatment of diseases, and pharmacologically acceptable salts thereof. The present invention also relates to intermediates necessary for the synthesis of the above-mentioned heterocyclic amide compounds.

BACKGROUND ART

Angiotensin II shows physiological activities such as vasopression by strong contraction of blood vessel, stimulation of aldosterone secretion from adrenal cortex (aldosterone retains sodium), and the like, and is considered to be a causative substance or risk factor of diseases such as hypertension, hypercardia, myocardial infarction, arteriosclerosis, diabetic and non-diabetic renal diseases, vascular restenosis after PTCA (percutaneous transluminal coronary angioplasty) and the like.

It is known that this angiotensin II is generated by cleavage of two amino acid residues from angiotensin I, which is a peptide consisting of ten amino acids present in a living body, and that angiotensin converting enzyme (ACE) is involved in said cleavage. Thus, numerous ACE inhibitors have been developed for the prophylaxis and treatment of the above-mentioned diseases.

Meanwhile, actions of a chymase group including human heart chymase, human mast cell chymase and human cutis chymase, which is one of the subfamilies of serine protease, have been drawing attention in recent years.

It has been clarified that chymase is involved in the course of generation, which is independent from ACE, of angiotensin II in the conversion of the above-mentioned angiotensin I to angiotensin II (Okunishi et al., Jpn. J. Pharmacol. 1993, 62, p. 207 etc. and others). Also, chymase is known to use, as substrates, numerous physiologically active substances such as extracellular matrix, cytokine, substance P, VIP (vasoactive intestinal polypeptide), apoprotein B and the like, and known to be responsible for the activation of other proteases such as collagenase (Igakuno Ayumi, Miyazaki et al., 1995, 172, p. 559).

Therefore, chymase inhibitors are expected to become inhibitors of angiotensin II action, as well as agents for the prophylaxis and treatment of various diseases caused by chymase, since it inhibits generation of ACE non-dependent angiotensin II. A patent application drawn to a chymase inhibitor based on these ideas has been already filed (WO93/25574).

The above-mentioned patent application WO93/25574 in the name of PFIZER INC. discloses a series of peptide compounds which are chymase (inclusive of human heart chymase) inhibitors. However, these compounds are peptide compounds which are unsatisfactory in terms of oral absorption, and no pharmacological test data are available.

Patent applications filed by ZENECA LTD. (Japanese Patent Unexamined Publication Nos. 5-286946, 6-56785 and WO93/21210), J. Med. Chem. 1994, 37, p. 3090, J. Med. Chem. 1994, 37, p. 3303, J. Med. Chem. 1994, 37, p 3313 and others disclose or report heterocyclic compounds which are human leukocyte elastase inhibitors, and these compounds are known to selectively inhibit human leukocyte elastase.

It is therefore an object of the present invention to provide novel compounds having superior chymase inhibitory activity, pharmaceutical compositions thereof and chymase inhibitors.

DISCLOSURE OF THE INVENTION

The present inventors have conducted intensive studies in an attempt to achieve the above-mentioned objects, and found that, by modifying or converting a part of the structure of the compound disclosed by ZENECA LTD., compounds can be obtained that inhibit chymase group, inclusive of human heart chymase, with high selectivity, without inhibiting other enzymes such as human leukocyte elastase, and exhibit superior absorption and safety, which resulted in the completion of the present invention.

Accordingly, the present invention relates to heterocyclic amide compounds of the formula (I)

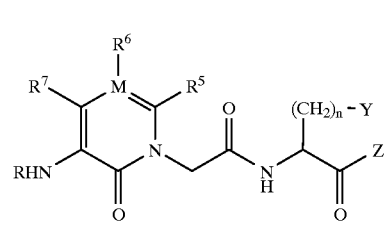

wherein

R is hydrogen, alkyl, —CHO, —CONH$_2$, —COR$^1$, —COOR$^1$, —CONHOR$^1$, —CONHR$^1$, —CONR$^1$R$^{11}$, —CONHSO$_2$R$^1$, —COSR$^1$, —COCOR$^2$, —COCOOR$^2$, —CONHCOOR$^2$, —COCONR$^3$R$^4$, —CSXR$^1$, —SO$_2$WR$^1$, —SO$_2$NR$^1$R$^{11}$ or —SO$_2$E wherein R$^1$ and R$^{11}$ may be the same or different and each is independently alkyl, cycloalkyl, cycloalkylalkyl, aryl, arylalkyl, heteroaryl, heteroarylalkyl, heterocycle or heterocyclealkyl, R$^2$, R$^3$ and R$^4$ may be the same or different and each is independently hydrogen, alkyl or arylalkyl, —NR$^3$R$^4$ may, in combination, show heterocycle, X is a direct bond, —NH—, —O— or —S—, W is a direct bond, —NH—, —NHCO—, —NHCOC— or —NHCONH—, and E is hydroxy or amino;

R$^5$, R$^6$ and R$^7$ may be the same or different and each is independently hydrogen or alkyl, or one of R$^5$, R$^6$ and R$^7$ is aryl, arylalkyl, arylalkenyl, heteroaryl, heteroarylalkyl or heteroarylalkenyl and the rest are hydrogen;

M is a carbon or nitrogen, provided that when M is a nitrogen, R$^6$ is void;

Y is cycloalkyl, aryl or heteroaryl;

Z is —CF$_2$R$^8$, —CF$_2$CONR$^9$R$^{10}$, —CF$_2$COOR$^9$, —COOOR$^9$ or —CONR$^9$R$^{10}$ wherein
R[8] is hydrogen, halogen, alkyl, perfluoroalkyl, aminoalkyl, alkylaminoalkyl, dialkylaminoalkyl, alkoxyalkyl, hydroxyalkyl, aryl, arylalkyl, arylalkenyl, heteroaryl, heteroarylalkyl or heteroarylalkenyl, R[9] and R[10] may be the same or different and each is independently hydrogen, alkyl, alkenyl, cycloalkyl, cycloalkylalkyl, heterocyclealkyl, aryl, arylalkyl, arylalkenyl, heteroaryl, heteroarylalkyl or heteroarylalkenyl, and —NR[9]R[10] may, in combination, show heterocycle; and n is 0 or 1;

provided that,
of the above-mentioned groups, alkyl, cycloalkyl, cycloalkylalkyl, aryl, arylalkyl, arylalkenyl, heteroaryl, heteroarylalkyl, heteroarylalkenyl, heterocycle and heterocyclealkyl optionally have substituent(s), (hereinafter this compound is also referred to as compound (I)) and pharmacologically acceptable salts thereof.

The present invention also relates to the above-mentioned heterocyclic amide compounds wherein, in the formula (I), Y is aryl optionally having substituent(s), and pharmacologically acceptable salts thereof; the above-mentioned heterocyclic amide compounds wherein, in the formula (I), Z is —CF$_2$R[8] or —CF$_2$CONR[9]R[10], and pharmacologically acceptable salts thereof; and the above-mentioned heterocyclic amide compounds wherein, in the formula (I), one of R[5], R[6] and R[7] is aryl optionally having substituent(s) and the rest are hydrogen, provided that when M is nitrogen, R[6] is void, and pharmacologically acceptable salts thereof.

The present invention further relates to compounds of the formula (II) which are useful for synthesizing compound (I)

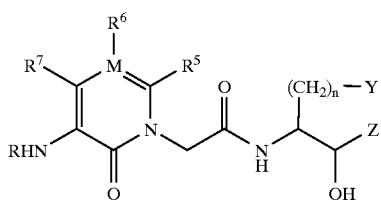

(II)

wherein each symbol is as defined above (hereinafter this compound is also referred to as compound (II)).

The present invention also relates to pharmaceutical positions containing compound (I) or a pharmacologically acceptable salt thereof and a pharmacologically acceptable carrier, and to pharmaceutical use thereof, particularly to chymase inhibitors.

Each symbol used in ths specification is explained in the following.

Alkyl CHR, R[1], R[11] and R[2]–R[10] may be straight or branched and preferably has 1 to 6 carbon atoms, and is exemplified by methyl, ethyl, n-propyl, isopropyl, n-butyl, isobutyl, sec-butyl, tert-butyl, n-pentyl, isopentyl, n-hexyl and the like.

Cycloalkyl at R[1], R[11], R[9], R[10] and Y preferably has 3 to 7 carbon atoms, and is exemplified by cyclopropyl, cyclobutyl, cyclopentyl, cyclohexyl, cycloheptyl and the like.

Cycloalkylalkyl at R[1], R[11], R[9] and R[10] has the same cycloalkyl moiety as above and its alkyl moiety may be straight or branched and preferably has 1 to 3 carbon atoms. Examples thereof include cyclopropylmethyl, 2-cyclobutylethyl, 3-cyclopentylpropyl, cyclohexylmethyl, 2-cyclohexylethyl, cycloheptylmethyl and the like.

Aryl at R[1], R[11], R[5]–R[10] and Y is preferably phenyl, naphthyl, an ortho-fused bicyclic group having 8 to 10 cyclic atoms wherein at least one ring is aromatic ring (e.g., indenyl) and the like.

Arylalkyl at R[1], R[11] and R[2]–R[10] has the same aryl moiety as above and its alkyl moiety may be straight or branched and preferably has 1 to 3 carbon atoms. Examples thereof include benzyl, phenethyl, 3-phenylpropyl, 1-naphthylmethyl, 2-naphthylmethyl, 2-(1-naphthyl)ethyl, 2-(2-naphthyl)ethyl, 3-(1-naphthyl)propyl, 3-(2-naphthyl)propyl and the like.

Arylalkenyl at R[5]–R[7] has the same aryl moiety as above and its alkenyl moiety may be straight or branched and preferably has 2 to 6 carbon atoms. Examples thereof include 3-phenyl-2-propenyl, 4-phenyl-3-butenyl, 5-phenyl-4-pentenyl, 6-phenyl-5-hexenyl, 3-(1-naphthyl)-2-propenyl, 4-(2-naphthyl)-3-butenyl and the like.

Arylalkenyl at R[8]–R[10] has the same aryl moiety as above and its alkenyl moiety may be straight or branched and preferably has 3 to 6 carbon atoms. Examples thereof include 3-phenyl-2-propenyl, 4-phenyl-3-butenyl and the like.

Heteroaryl at R[1], R[11], R[5]–R[10] and Y is preferably a 5 or 6-membered ring having carbon atom(s) and 1 to 4 hetero atoms (oxygen, sulfur or nitrogen) and an ortho-fused bicyclic heteroaryl having 8 to 10 cyclic atoms, particularly benzo derivatives, and those produced by fusing propenylene, trimethylene or tetramethylene therewith, and its stable N-oxide and the like. Examples thereof include pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,2,4-thiadiazolyl, pyridyl, pyranyl, pyrazinyl, pyrimidinyl, pyridazinyl, 1,2,4-triazinyl, 1,2,3-triazinyl, 1,3,5-triazinyl, benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl, benzoxazinyl and the like.

Heteroarylalkyl at R[1], R[11] and R[5]–R[10] has the same heteroaryl moiety as above and its alkyl moiety may be straight or branched and preferably has 1 to 3 carbon atoms. Examples thereof include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)-ethyl, 3-(2-pyrrolyl)propyl and the like.

Heteroarylalkenyl at R[5]–R[7] has the same heteroaryl moiety as above and its alkenyl moiety may be straight or branched and preferably has 2 to 6 carbon atoms. Examples thereof include 3-(2-pyridyl)-2-propenyl, 4-(3-pyridyl)-3-butenyl, 5-(2-pyrrolyl)-4-pentenyl, 6-(2-thienyl)-5-hexenyl and the like.

Heteroarylalkenyl at R[8]–R[10] has the same heteroaryl moiety as above and its alkenyl moiety may be straight or branched and preferably has 3 to 6 carbon atoms. Examples thereof include 3-(2-pyridyl)-2-propenyl, 4-(2-pyridyl)-3-butenyl and the like.

Heterocycle at $R^1$ and $R^{11}$ is a 4 to 6-membered ring having carbon atom(s) and 1 to 4 hetero atoms (oxygen, sulfur or nitrogen), which is exemplified by azetidinyl, pyrrolidinyl, piperidinyl, piperidino, piperazinyl, morpholinyl, morpholino, thiomorpholinyl, oxothiomorpholinyl, dioxothiomorpholinyl, tetrahydropyranyl, dioxacyclohexyl and the like.

Heterocycle represented by —$NR^3R^4$ and —$NR^9R^{10}$ is a 4 to 6-membered ring having carbon atom(s), at least one nitrogen atom and optionally other hetero atom (oxygen or sulfur), which is exemplified by azetidinyl, pyrrolidinyl, piperidino, piperazinyl, morpholino, thiomorpholino, oxothiomorpholino, dioxothiomorpholino and the like.

Heterocyclealkyl at $R^1$, $R^{11}$, $R^9$ and $R^{10}$ has the same heterocycle moiety as above ($R^1$, $R^{11}$) and its alkyl moiety may be straight or branched and preferably has 1 to 3 carbon atoms. Examples thereof include azetidinylethyl, pyrrolidinylpropyl, piperidinylmethyl, piperidinoethyl, piperazinylethyl, morpholinylpropyl, morpholinomethyl, thiomorpholinylethyl, oxothiomorpholinylethyl, dioxothiomorpholinylethyl, tetrahydropyranylpropyl, dioxacyclohexylmethyl and the like.

Halogen at $R^8$ is exemplified by fluorine, chlorine, bromine and iodine.

Perfluoroalkyl at $R^8$ may be straight or branched and preferably has 1 to 6 carbon atoms. Examples thereof include trifluoromethyl, pentafluoroethyl, heptafluoropropyl and the like.

Aminoalkyl at $R^8$ has an alkyl moiety which may be straight or branched and preferably has 1 to 6 carbon atoms. Examples thereof include aminomethyl, aminoethyl, aminopropyl, aminobutyl, aminopentyl, aminohexyl and the like.

Alkylaminoalkyl at $R^8$ has an alkyl moiety which may be straight or branched and preferably has 1 to 6 carbon atoms. Examples thereof include methylaminomethyl, methylaminoethyl, ethylaminopropyl, ethylaminobutyl, methylaminopentyl, methylaminohexyl and the like.

Dialkylaminoalkyl at $R^8$ has an alkyl moiety which may be straight or branched and preferably has 1 to 6 carbon atoms. Examples thereof include dimethylaminomethyl, dimethylaminoethyl, diethylaminopropyl, diethylaminobutyl, dimethylaminopentyl, dimethylaminohexyl and the like.

Alkoxyalkyl at $R^8$ has an alkoxy moiety and alkyl moiety which may be respectively straight or branched and preferably have 1 to 6 carbon atoms. Examples thereof include methoxymethyl, methoxyethyl, ethoxypropyl, ethoxybutyl, methoxypentyl, methoxyhexyl and the like.

Hydroxyalkyl at $R^8$ has an alkyl moiety which may be straight or branched and preferably has 1 to 6 carbon atoms. Examples thereof include hydroxymethyl, hydroxyethyl, hydroxypropyl, hydroxybutyl, hydroxypentyl, hydroxyhexyl and the like.

Alkenyl at $R^9$ and $R^{10}$ may be straight or branched and preferably has 3 to 6 carbon atoms, and exemplified by 2-propenyl, 3-butenyl, 4-pentenyl, 5-hexenyl and the like.

Of the above-mentioned substituents, alkyl, cycloalkyl, cycloalkylalkyl, aryl, arylalkyl, arylalkenyl, heteroaryl, heteroarylalkyl, heteroarylalkenyl, heterocycle and heterocyclealkyl may be substituted by one or more substituents from the following.

Examples of the substituent include halogen, hydroxy, nitro, cyano, trifluoromethyl, alkyl, alkoxy, alkylthio, formyl, acyloxy, oxo, phenyl, arylalkyl, —COORa, —$CH_2COORa$, —$OCH_2COORa$, —CONRbRc, —$CH_2CONRbRc$, —$OCH_2CONRbRc$, —$COO(CH_2)_2NReRf$, —$SO_2T^1$, —$CONRdSO_2T^1$, —NReRf, —NRgCHO, —$NRgCOT^2$, —$NRgCOOT^2$, —NRhCQNRiRj, —$NRkSO_2T^3$, —$SO_2NRlRm$, —$SO_2NRnCOT^4$ and the like.

With respect to the above-mentioned substituents, halogen, alkyl and arylalkyl are exemplified by those mentioned above. Alkoxy may be straight or branched and preferably has 1 to 6 carbon atoms. Examples thereof include methoxy, ethoxy, propoxy, butoxy, pentyloxy, hexyloxy and the like. Alkylthio may be straight or branched and preferably has 1 to 6 carbon atoms. Examples thereof include methylthio, ethylthio, propylthio, butylthio, pentylthio, hexylthio and the like. Acyloxy may be straight or branched and preferably has 1 to 6 carbon atoms. Examples thereof include formyloxy, acetyloxy, propionyloxy, butyryloxy, valeryloxy, pivaloyloxy, hexanoyloxy and the like.

Ra-Rn means hydrogen, alkyl (as defined above) or arylalkyl (as defined above). —NRbRc, —NReRf, —NRiRj and —NRlRm may, together with the adjacent nitrogen, mean heterocycle (same as those exemplified by —$NR^3R^4$ and —$NR^9R^{10}$, which may be substituted by the above-mentioned substituents), and —NReRf may mean heteroaryl having =O (e.g., 2-pyrrolidinon-1-yl, succinimido, oxazolidin-2-on-3-yl, 2-benzoxazolinon-3-yl, phthalimido, cis-hexahydrophthalimido and the like). $T^1$–$T^4$ mean the same groups as the above-mentioned $R^1$, which may be substituted by the above-mentioned substituents. Q means =O or =S.

The compound (I) can exist as optically active compounds and racemates due to asymmetric carbon to which —$(CH_2)$n-Y is bonded. Said racemates can be resolved into optically active compounds by a method known per se. When compound (I) has additional asymmetric carbon, the compound can exist as diastereomer mixtures or a single diastereomer. Each diastereomer can be isolated by a method known per se.

The compound (I) can exhibit a polymorphism, and can exist as more than one tautomers. In addition, it can exist as solvates (e.g., ketone solvate, hydrate and the like.).

Therefore, the present invention encompasses any stereoisomers, optical isomers, polymorphs, tautomers, solvates mentioned above and optional mixtures thereof.

When the compound (I) is an acidic compound, its pharmacologically acceptable salt is exemplified by alkali metal salt (e.g., salts with lithium, sodium, potassium and the like), alkaline earth metal salt (e.g., salts with calcium, magnesium and the like), aluminum salt, ammonium salt, salts with organic base (e.g., salts with triethylamine, morpholine, piperidine, triethanolamine and the like), and the like.

When the compound (I) is a basic compound, its pharmacologically acceptable salt is exemplified by inorganic acid addition salt (e.g., salts with hydrochloric acid, hydrobromic acid, hydriodic acid, sulfuric acid, phosphoric acid and the like), organic acid addition salt (e.g., salts with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid and the like), salts with amino acid (e.g., salts with glutamic acid, aspartic acid and the like), and the like.

More preferable compound is exemplified by the compounds of Examples to be mentioned later, namely, compounds of Examples 3, 4, 7, 8, 29, 33, 48, 50, 61, 62, 83, 84, 87, 88, 90 and 93 and the like.

The production method of the compound (I) of the present invention is shown in the following scheme I.

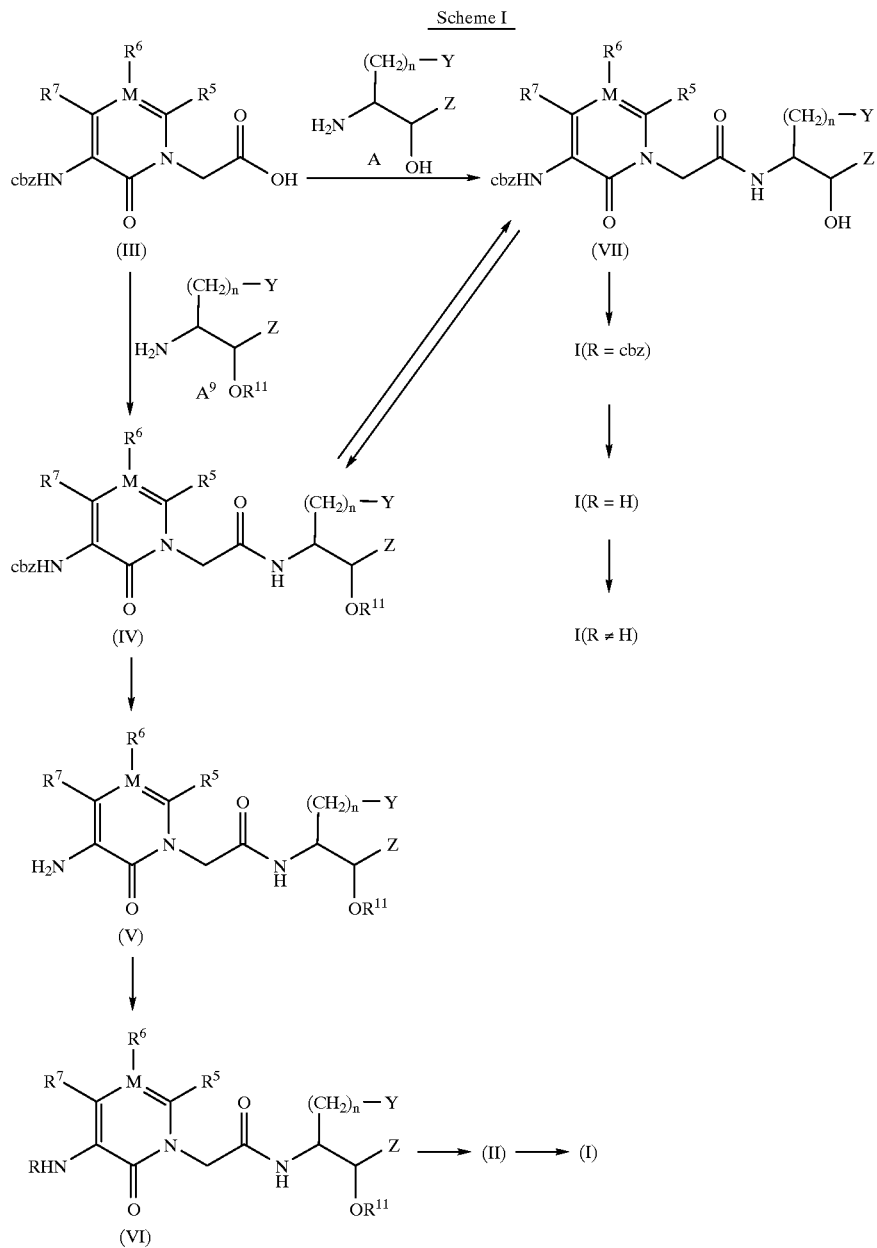

Of the compounds of the present invention, preferable compound is a compound wherein, in the formula (I), Y is aryl optionally having substituent(s); a compound wherein, in the formula (I), Z is $-CF_2R^8$ or $-CF_2CONR^9R^{10}$; a compound wherein, in the formula (I), one of $R^5$, $R^6$ and $R^7$ is aryl optionally having substituent(s) and the rest are hydrogen, provided that when M is nitrogen, $R^6$ is void; and the like.

wherein $R^{11}$ is hydroxy-protecting group (e.g., tert-butyldimethylsilyl, triisopropylsilyl, tert-butyldiphenylsilyl and the like), cbz is benzyloxycarbonyl and other symbols are as defined above.

As shown in the above scheme I, compound (III) is condensed with amine A to give compound (VII) or compound (III) is condensed with amine A' to give compound (IV).

The compound (III) may be a compound disclosed in publications (e.g., Japanese Patent Unexamined Publication Nos. 6-56785, 5-286946, Warner et al., J. Med. Chem. 1994, 37, p. 3090, Damewood et al., J. Med. Chem. 1994, 37, p. 3303, Veale et al., J. Med. Chem. 1995, 38,. p. 98, WO93/21210 and the like) or can be prepared by a conventional method based on these publications. The production methods of amine A and amine A' are described later.

A condensing agent used for this condensation and which activates carboxylic acid of compound (III) may be suitably dicyclohexylcarbodiimide (DCC)/hydroxybenzotriazole (HOBT), N-(3-dimethylaminopropyl)-N'-ethylcarbodiimide (WSCI), hydrochloride thereof/HOBT, WSCI or hydrochrolide thereof/4-dimethylaminopyridine (DMAP), 2-ethoxy-1-ethoxycarbonyl-1,2-dihydroquinoline (EEDQ), carbonyldiimidazole (CDI)/HOBT, diethylphosphoryl cyanide and the like.

Said reaction is generally carried out in an inert solvent wherein the inert solvent used may be any as long as it is aprotic. Suitable examples thereof include acetonitrile, dichloromethane, chloroform, N,N-dimethylformamide and the like. The condensation is generally carried out at a temperature of −30° C. to 80° C., preferably 0° C. to 25° C.

The hydroxy group of compound (VII) thus obtained may be protected to give compound (IV). Conversely, the hydroxy-protective group ($R^{11}$) of compound (IV) may be deprotected to give compound (VII).

Benzyloxycarbonyl of compound (IV) can be removed by a conventional method, such as hydrogenolysis and the like, to give compound (V).

The amino bound to carbon on heterocyclic ring (e.g., pyridone ring or pyrimidone ring) of compound (V) is acylated or sulfonylated by a conventional method to give a compound (VI) wherein R is substituent other than hydrogen.

A compound (VI) wherein R is —CHO, —CONH$_2$, —COR$^1$, —COOR$^1$, —CONHOR$^1$, —CONHR$^1$, —CONR$^1$R$^{11}$, —CONHSO$_2$R$^1$, —COSR$^1$, —COCOR$^2$, —COCOOR$^2$, —CONHCOOR$^2$ or —COCONR$^3$R$^4$ is synthesized by using an active carboxylic acid derivative such as acid halide, using carboxylic acid and a coupling agent, and other method.

When a compound (VI) wherein R is —CONH$_2$, —CONHR$^1$, —CONHSO$_2$R$^1$ or —CONHCOOR$^2$ is synthesized using isocyanate and the like. Alternatively, carbonyldiimidazole, phosgene, diphosgene (trichloromethyl chloroformate), triphosgene [bis (trichloromethyl)carbonate] or the like is used with an alcohol of the formula: R$^1$OH, thiol of the formula: R$^1$SH or an amine of the formula: R$^1$NH$_2$, (R$^1$)$_2$NH or R$^1$ONH$_2$, and a base such as triethylamine and the like.

When a compound (VI) wherein R is —CSXR$^1$ is synthesized, the method therefor includes the use of activated thiocarboxylic acid derivative (e.g., thioyl chloride, lower alkyl ester of dithioic acid and the like), the use of thioic acid and a coupling agent, and the like. Alternatively, a method may be used wherein dimethyl trithiocarbonate and the like is used with an alcohol of the formula: R$^1$OH, thiol of the formula: R$^1$SH or amine of the formula: R$^1$NH$_2$. When a compound (VI) wherein X is —NH— is synthesized, isothiocyanate may be used.

When a compound (VI) wherein R is —SO$_2$WR$^1$, —SO$_2$NR$^1$R$^{11}$ or —SO$_2$E is synthesized, the following method is suitable for sulfonylation. For example, a sulfonic acid of the formula: HO—SO$_2$WR$^1$, HO—SO$_2$NR$^1$R$^{11}$ or HO—SO$_2$E, or a corresponding acid halide, particularly, sulfonyl (or sulfamoyl) chloride of the formula: Cl—SO$_2$WR$^1$, Cl—SO$_2$NR$^1$R$^{11}$ or Cl—SO$_2$E and an organic base (e.g., triethylamine, pyridine and the like) or inorganic base (e.g., sodium carbonate, potassium carbonate and the like) are used in an inert solvent (e.g., dichloromethane, tetrahydrofuran, toluene and the like).

When compound (VI) comprises —COORa (carboxyl) wherein Ra is hydrogen as a substituent of each substituent at R or Z, for example, said compound is obtained by decomposing the corresponding ester (compound (VI) having, as substituent of substituent, —COORa wherein Ra is not hydrogen) synthesized using a suitably-removable acid protecting group. This decomposition can be carried out by a various methods known in organic chemistry, such as basic hydrolysis using lithium hydroxide or sodium hydroxide or hydrogenolysis of benzyl ester and the like.

When compound (VI) comprises —COORa, —CONRbRc, —COO(CH$_2$)$_2$NReRf or —CONRdSO$_2$T$^1$ as a substituent of each substituent at R or Z, for example, said compound is obtained by reacting a compound of the formula: HORa, HNRbRc, HO(CH$_2$)$_2$NReRf or HNRdSO$_2$T$^1$ (when Ra-Rf is not hydrogen), and compound (VI) having, as substituent of substituent, —COORa (carboxyl) wherein Ra is hydrogen, or its active derivative.

When compound (VI) comprises —OCH$_2$COORa or —OCH$_2$CONRbRc as a substituent of each substituent at R$^5$–R$^7$, R or Z, for example, said compound is obtained by reacting a compound of the formula: BrCH$_2$COORa, ICH$_2$COORa, BrCH$_2$CONRbRc or ICH$_2$CONRbRc (when Ra-Rc is not hydrogen) and compound (VI) having, as substituent of substituent, hydroxy in the presence of a base such as sodium hydride and the like.

When compound (VI) comprises —NRgCOT$^2$, —NRgCOOT$_2$, —NRhCQNRiRj, —NRkSO$_2$T$^3$ or acyloxy as a substituent of each substituent at R$^5$–R$^7$, R or Z, for example, said compound is obtained by reacting the corresponding compound (VI) having, as substituent of substituent, hydroxy or amino such as —NHRg, —NHRh or —NHRk, with an active derivative of an acid of the formula: HOCOT$^2$, HOCOOT$^2$, HOCQNRiRj or HOSO$_2$T$^3$.

When compound (VI) comprises heteroaryl-N-oxide in R$^5$–R$^7$, R or Z, said compound is obtained by oxidizing the corresponding compound (VI) having heteroaryl in R$^5$–R$^7$, R or Z using a conventional oxidizing agent such as dioxirane in acetone and the like.

While conversion and the like of a substituent of each substituent in R, Z and the like have been explained by referring to compound (VI), such conversion and the like are not limited to compound (VI) alone, but, as long as they are unaffecting other functional groups present in the chemical structure, applicable to various other compounds. For example, when substituent of substituent in R, Z and the like is amino or hydroxy, the conversion is preferably carried out not with respect to compound (VI) but compound (I).

The compound (II) is obtained by removing the hydroxy-protecting group ($R^{11}$) of compound (VI). This compound (II) is useful as an intermediate for the synthesis of compound (I).

The hydroxy-protecting group is removed using tetrabutylammonium fluoride in an inert solvent such as tetrahydrofuran, wherein the reaction mixture is preferably bufferred using an acid such as acetic acid.

Then, hydroxy of compound (II) is oxidized to give compound (I).

The oxidization is preferably carried out by, for example, using dimethyl sulfoxide in excess and water soluble carbodiimide at about room temperature in an inert solvent such as toluene and using dichloroacetic acid as a catalyst. Other useful methods include, for example, the use of aqueous alkaline potassium permanganate solution; the use of oxalyl chloride, dimethyl sulfoxide and tertiary amine; the use of acetic anhydride and dimethyl sulfoxide; the use of pyridine-sulfur trioxide complex and dimethyl sulfoxide; the use of chromium (VI) oxide-pyridine complex in methylene chloride; and the use of hypervalent iodine reagent such as periodinane (e.g., 1,1,1-triacetoxy- 1,1-dihydro-1,2-benziodoxol-3(1H)-one) in dichloromethane or dimethylformamide.

Hydroxy of compound (VII), which is obtained by condensing compound (III) and amine A or elimination of hydroxy-protecting group of compound (IV), is oxidized by the above-mentioned method to give compound (I) having amino protected by benzyloxycarbonyl.

This compound is then deprotected by removing benzyloxycarbonyl by the above-mentioned method to give compound (I) wherein R is hydrogen.

This compound may be subjected to acylation and the like to give compound (I) wherein R is other than hydrogen.

Scheme II shows different production method of compound (IV). This method is applicable only when M is carbon.

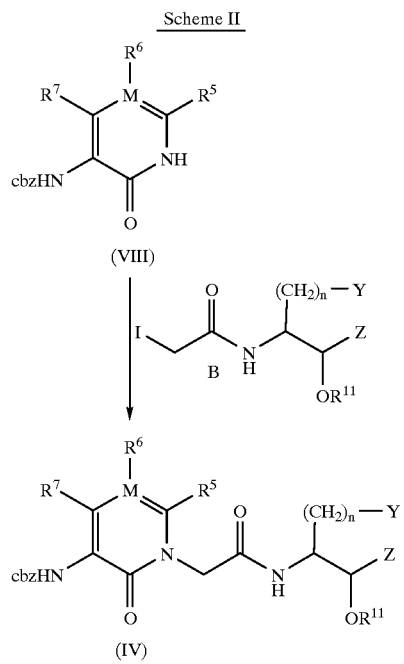

wherein each symbol is as defined above.

As shown in the above scheme II, compound (VIII) (compound disclosed in publications such as Japanese Patent Unexamined Publication No. 6-56785, Warner et al., J. Med. Chem. 1994, 37, p. 3090 and Damewood et al., J. Med. Chem. 1994, 37, p. 3303, or compound prepared by a conventional method according to these publications) and compound B are reacted to give compound (IV). The production method of compound B is to be described later.

This reaction includes, for example, as disclosed in Japanese Patent Unexamined Publication No. 6-56785 and J. Med. Chem. 1994, 37, p. 3303, treating compound (VIII) in an aprotic solvent, particularly an inert solvent such as N,N-dimethylformamide and tetrahydrofuran, using a base, such as sodium hydride and potassium hydride, at −30° C. to 80° C., preferably at 0° C. to 30° C. and then reacting the resulting compound with compound B at −30° C. to 80° C., preferably at 0° C. to 30° C.

The compound (IV) thus obtained is converted to compound (I) by the method shown in scheme I.

Amine A, amine A' and compound B necessary for the above-mentioned synthesis can be synthesized by the methods shown in the following schemes III–VII.

In scheme III, synthetic method of amine A wherein Z is —$CF_2R^8$ wherein $R^8$ is hydrogen, fluorine, alkyl or perfluoroalkyl is shown.

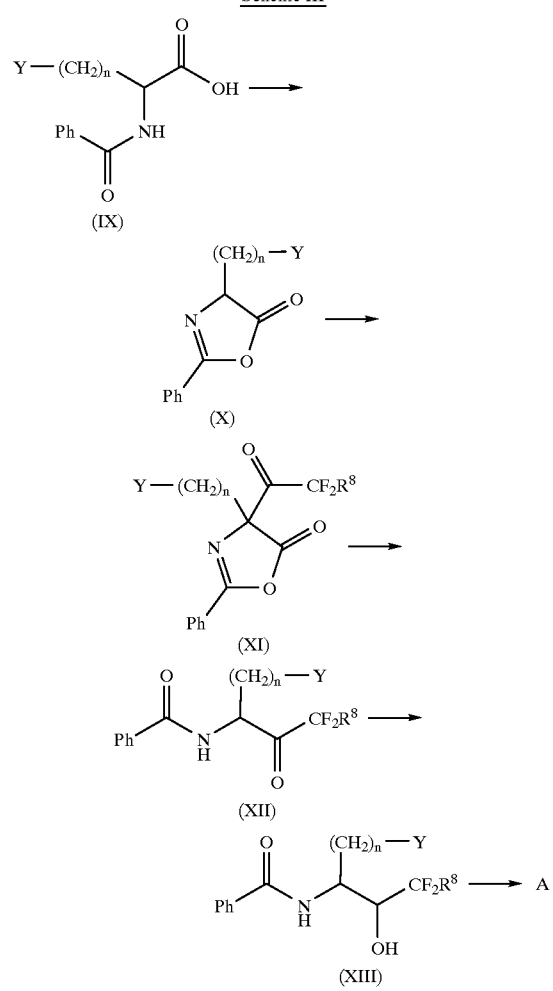

wherein Ph is phenyl and other symbols are as defined above.

As disclosed in the reports of Kolb et al. (Liebigs Ann. Chem. 1990, p. 1) and Peet et al. (J. Med. Chem. 1990, 33, p. 394), N-aroylamino acid derivative (IX) is treated with acetic anhydride to give oxazolone (X). This oxazolone (X) is reacted with acid anhydride (e.g., when Z is $CF_3$, it is trifluoroacetic anhydride) having the desired Z to give compound (XI) into which acyl has been introduced. Then, the compound is subjected to decarboxylation using oxalic acid to give compound (XII), followed by reduction of carbonyl adjoining —$CF_2R^8$ to give compound (XIII). Finally, hydrolysis using an acid to remove aroyl gives amine A.

In the following method shown in scheme IV, amine A can be synthesized wherein Z is —$CF_2R^8$ wherein $R^8$ is not limited to hydrogen, fluorine, alkyl and perfluoroalkyl.

Scheme IV

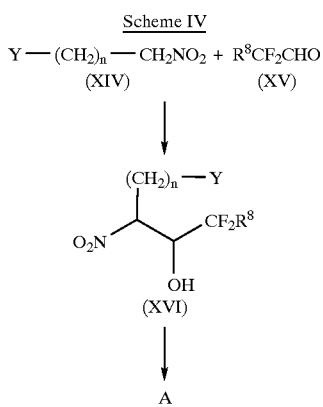

wherein each symbol is as defined above.

As disclosed in the report of McBee et al. (J. Am. Chem. Soc. 1956, 78, p. 4053), a suitable nitroalkane (XIV) is condensed with compound (XV) to give nitro alcohol (XVI). The compound (XV) can be synthesized by, for example, the method disclosed in the report of Welch (Tetrahedron Lett. 1987, 43, p. 3123) combined with general methods in organic chemistry. In addition, compound (XV) can exist as hydrate or hemiacetal. Then, according to the method of, for example, Abeles et al. (Biochemistry, 1987, 26, p. 4474), nitro of this compound (XVI) is reduced with a suitable reducing agent to give amine A.

When $R^8$ is a substituent having amino and hydroxy, said amino and the like need to be protected by a stable protecting group in each reaction mentioned above.

Scheme V shows synthetic method of amine A wherein Z is —$COOR^9$.

Scheme V

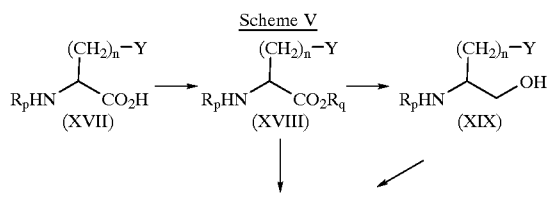

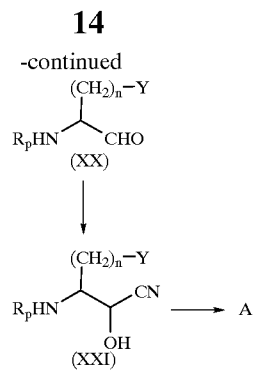

wherein Rp is amino-protecting group (e.g., benzyloxycarbonyl (cbz), tert-butoxycarbonyl (BOC) and the like), Rq is alkyl having 1 to 6 carbon atoms and other symbols are as defined above.

Compound (XVII) is esterified first to give compound (XVIII).

This esterification may be carried out by, for example, reacting the compound with alkyl halide corresponding to Rq, in the presence of a base such as potassium hydrogencarbonate, or by reacting with diazoalkane.

While a number of α-amino acids of the formula (XVII) wherein amino is protected are commercially available, when using one which is not commercially available, such α-amino acid can be synthesized by obtaining amino acid from aldehyde Y—$(CH_2)$nCHO by Strecker synthesis method or other method known per se, followed by protection of the amino.

Then, compound (XVIII) is reduced using, for example, diisobutylaluminum hydride to give compound (XX) with ease. As shown in the report of Fehrentz et al. (Synthesis, 1983, p. 676), compound (XVII) is condensed with N,O-dimethylhydroxylamine to give an amide derivative and the derivative is reduced with lithium aluminum hydride for the desired synthesis.

A different method include reducing compound (XVIII) with, for example, sodium borohydride/lithium chloride to give compound (XIX) and oxidizing compound (XIX) by the oxidizing method, which has been described for conversion of compound (II) to compound (I), to give compound (XX).

Then, compound (XX) treated with cyanide salt, preferably potassium cyanide or sodium cyanide, in the presence of an auxiliary solvent such as tetrahydrofuran, ethyl acetate and dioxane in an aqueous solution to give compound (XXI).

The compound (XXI) thus obtained can be converted to amine A wherein Z is —$COOR^9$ by decomposition of cyano by the addition of alcohol.

This reaction is generally done by reacting compound (XXI) and compound $R^9OH$ in the presence of a suitable proton source (e.g., hydrogen chloride). In this case, the protecting group Rp of amino may be simultaneously removed. In the contrary case, the protecting group is eliminated by a method known per se. The points to note when $R^9$ is a substituent having amino and the like are as described above.

When Z is —$CONR^9R^{10}$, amine A is synthesized as in the following.

The amino group of amine A wherein Z is —$COOR^9$ is protected with Rp, and ester ($COOR^9$) is hydrolyzed by the above-mentioned method known per se. The resulting hydroxy acid and amine $HNR^9R^{10}$ are condensed by the above-mentioned method known per se. Finally, the protecting group Rp is removed to give a desired compound.

A different method includes reacting amine A wherein Z is $-COOR^9$ with excess amine $HNR^9R^{10}$ in a lower alcohol, preferably methanol, ethanol or isopropanol, at 25–100° C. In this case, a reaction in a closed system using a stainless steel autoclave and the like is preferable. The points to note when $R^9$ and $R^{10}$ are substituents having amino and the like are as described above.

Scheme VI shows synthetic method of amine A wherein Z is $-CF_2COOR^9$ or $-CF_2CONR^9R^{10}$.

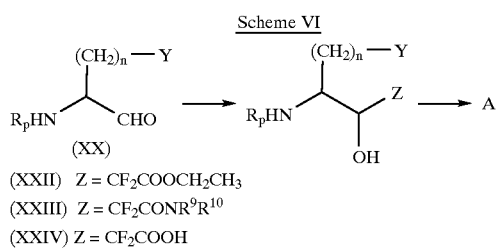

Scheme VI (XXII) $Z = CF_2COOCH_2CH_3$
(XXIII) $Z = CF_2CONR^9R^{10}$
(XXIV) $Z = CF_2COOH$ wherein each symbol is as defined above.

For example, compound (XX) synthesized in scheme V is reacted with (1) ethyl bromodifluoroacetate in the presence of zinc powder according to the method of Hallinan and Fried (Tetrahedron Lett. 1984, 25, p. 2301) and Thairivongs et al. (J. Med. Chem. 1986, 29, p. 2080); or (2) ethyl chlorodifluoroacetate in the presence of zinc powder according to the method of Lang and Schaub (Tetrahedron Lett. 1988, 29, p. 2943); or (3) ethyl bromodifluoroacetate, zinc powder and titanium tetrachloride according to the method of Hoover (U.S. Pat. No. 4,855,303) to give compound (XXII) wherein Z is $-CF_2COOCH_2CH_3$.

This compound (XXII) is reacted with amine $HNR^9R^{10}$ in a protic polar solvent, preferably ethanol or methanol, to give compound (XXIII) wherein Z is $-CF_2CONR^9R^{10}$.

Removal of amino-protecting group Rp of compound (XXII) results in amine A wherein Z is $-CF_2COOCH_2CH_3$.

Removal of amino-protecting group Rp of compound (XXIII) results in amine A wherein Z is $-CF_2CONR^9R^{10}$.

Moreover, amine A wherein Z is $-CF_2CONR^9R^{10}$ or $-CF_2COOR^9$ can be synthesized from compound (XXII) wherein Z is $-CF_2COOCH_2CH_3$ by the following method.

That is, the corresponding carboxylic acid obtained by hydrolysis of an ester of compound (XXII) wherein Z is $-CF_2COOCH_2CH_3$ or alkali metal salt, namely compound (XXIV) wherein Z is $-CF_2COOH$ or alkali metal salt thereof, is condensed with amine $HNR^9R^{10}$ or alcohol $R^9OH$ according to the above-mentioned method known per se. The protecting group Rp of the compound thus produced wherein Z is $-CF_2CONR^9R^{10}$ or $-CF_2COOR^9$ is removed to give amine A wherein Z is $-CF_2CONR^9R^{10}$ or $-CF_2COOR^9$. The points to note when $R^9$ and $R^{10}$ are substituents having amino and the like are as disclosed above.

While amine A can be obtained as mentioned above, hydroxy of this amine A is protected by a hydroxy-protecting group ($R^{11}$) to give amine A'. The hydroxy-protecting group is to be introduced when amino is protected by a protecting group Rp, and thereafter, amino-protecting group is removed.

Scheme VII shows synthetic method of compound B.

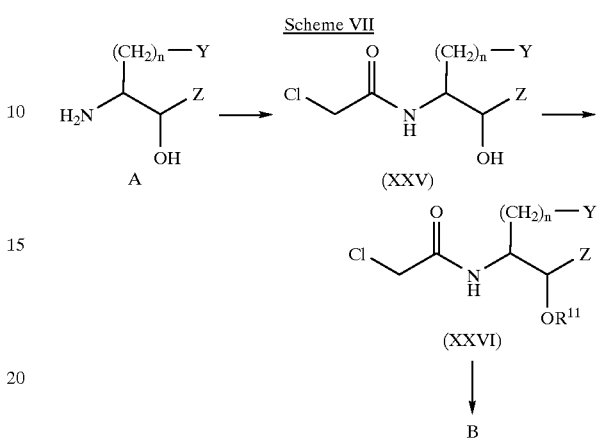

wherein each symbol is as defined above.

For example, this compound B is synthesized according to the report of Damewood et al. (J. Med. Chem. 1994, 37, p. 3303), wherein amine A is reacted with chloroacetyl chloride in an inert solvent such as tetrahydrofuran in the presence of an organic base such as N-methylmorpholine, at −20° C. to 60° C., preferably at 0° C. to 30° C., to give compound (XXV), whose hydroxy is protected by the above-mentioned protecting group ($R^{11}$), of which preferred is silyl such as tert-butyldimethylsilyl, to give compound (XXVI). This compound is reacted with sodium iodide or potassium iodide in an inert solvent such as acetone at −20° C. to 60° C., preferably at 0° C. to 30° C., to give the desired compound B.

The compound (I) of the present invention thus produced can be recovered at optional purity by known methods for separation and purification, such as concentration, extraction, chromatography, reprecipitation, recrystallization and the like.

The pharmacologically acceptable salts of said compound (I) can be also produced by a known method. Further, various isomers of said compound (I) can be produced by a known method.

The compound (I) and pharmacologically acceptable salts thereof of the present invention have superior inhibitory action on chymase groups in mammals such as human, dog, cat and the like.

The compound (I) and pharmacologically acceptable salts thereof of the present invention are useful as inhibitors of chymase groups inclusive of human heart chymase and are useful for the prophylaxis and treatment of various diseases caused by chymase, namely, for the prophylaxis and treatment of diseases considered to be caused by angiotensin II (e.g., hypertension, hypercardia, myocardial infarction, arteriosclerosis, diabetic and non-diabetic renal diseases, vascular restenosis after PTCA).

When the compound (I) and pharmacologically acceptable salts thereof of the present invention are used as pharmaceutical products, pharmacologically acceptable carrier and the like are used to prepare pharmaceutical composition in the form of granules, tablets, capsules, injection, ointments, creams, aerosols and the like which can be administered orally or parenterally. The above-mentioned pharmaceutical preparation contains an effective amount of compound (I) or its pharmacologically acceptable salt.

The dose of said compound (I) and its pharmacologically acceptable salt varies depending on administration route, symptoms of patients, body weight and age, and appropriately determined according to the administration purposes. In general, 0.01–1000 mg/kg body weight/day, preferably 0.05–500 mg/kg body weight/day, thereof is administered orally to an adult in a single to several doses per day.

The present invention is described in more detail by way of Examples, which should not be construed as limiting the invention.

$^1$H-NMR was determined at 200, 300 or 500 MHz. The chemical shift of $^1$H-NMR is expressed in parts per million (ppm) of relative delta ($\delta$) values using tetramethylsilane (TMS) as an internal standard. The coupling constant is expressed by s (singlet), d (doublet), t (triplet), q (quartet), m (multiplet), dd (doublet of doublets), brs (broad singlet), ABq (AB quartet) and the like, while indicating obvious multiplicity by hertz (Hz). Thin layer and column chromatographies were performed using a silica gel manufactured by Merck. For concentration, a rotary evaporator manufactured by Tokyo Rikakikai Co., Ltd. was used.

REFERENCE EXAMPLE 1

Synthesis of 3-amino-1,1,1-trifluoro-4-phenyl-2-butanol.

(1) To a mixture of phenylalanine (500 g, 3.03 mol), 2N aqueous sodium hydroxide solution (4 L) and ether (500 mL) was added dropwise benzoyl chloride (455 mL, 3.93 mol) under ice-cooling over about 55 min. The resulting mixture was stirred at room temperature for 16 h, cooled with ice and acidified with conc. hydrochloric acid to pH 2. The precipitated crystals were extracted with ethyl acetate. The obtained extracts were combined and washed with water, dried over anhydrous sodium sulfate and concentrated to ca. 2 L. Then hexane was added to the resulting suspension. The resulting precipitate was collected by filtration to give 815 g (100%) of N-benzoylphenylalanine.

(2) A suspension of the target compound in step (1) (815 g, 3.03 mol) in acetic anhydride (3.5 L) was stirred at room temperature for 16 h, and then concentrated under reduced pressure. To the resulting oil was added petroleum ether (3.5 L), and insolubles were removed by decantation. After cooling the supernatant, precipitates were collected by filtration to give 570 g (75%) of 2-phenyl-4-(phenylmethyl)-5(4H)-oxazolone as colorless needles.

(3) A mixture of the target compound in step (2) (259 g, 1.03 mol) and trifluoroacetic anhydride (260 g, 1.24 mol) was stirred at room temperature for 72 h. Excess trifluoroacetic anhydride and acetic acid formed were removed under reduced pressure, and then oxalic anhydride (139.1 g, 1.55 mol) was added to the residue. The resulting mixture was heated to 110° C. with stirring, and then, after gas evolving ceased, cooled to room temperature. Ethyl acetate (10 L) was added and the mixture was washed with water (2 L). The aqueous layer was further extracted with ethyl acetate and combined with the organic layers obtained earlier. The resulting mixture was dried over anhydrous magnesium sulfate and the solvent was concentrated to ca. 1 L. Hexane was added to the resulting suspension, and the precipitated solid was collected by filtration to give 215 g (65%) of N-[3,3,3-trifluoro-2-oxo-1-(phenylmethyl)propyl] benzamide.

(4) To a suspension of the target compound in step (3) (215 g, 673 mmol) in ethanol (1 L) was added sodium borohydride (25.4 g, 673 mmol) under ice-cooling. The resulting mixture was stirred for 4 h, cooled with ice, adjusted with 6N hydrochloric acid to pH 3, and then extracted with ethyl acetate. The extracts were combined and washed with saturated aqueous sodium hydrogencarbonate solution and brine, and dried over anhydrous sodium sulfate. The solvent was concentrated to ca. 300 mL and hexane was added to the resulting suspension. The precipitated solid was collected by filtration to give 130 g (60%) of N-[3,3,3-trifluoro-2-hydroxy-1-(phenylmethyl)propyl] benzamide.

(5) A mixture of the target compound in step (4) (130 g, 202 mmol), 12N hydrochloric acid (1.3 L), water (700 mL) and ethanol (900 mL) was refluxed under heating for 24 h. Thereto were added 12N hydrochloric acid (400 mL) and ethanol (800 mL) and the resulting mixture was further refluxed under heating for 72 h, concentrated to 1.2 L and cooled to room temperature. The precipitated crystals were extracted with ether. Sodium hydroxide was added to the aqueous layer under ice-cooling until its pH became 12, and the precipitated crystals were extracted with ethyl acetate. The ethyl acetate layer was dried over anhydrous sodium sulfate and the solvent was evapoarated. The residue was recrystallized from ethyl acetate-hexane (1:5) to give 58.7 g (66%) of the title compound as colorless crystals.

mp 110–111° C.; $^1$H-NMR (200 MHz, CDCl$_3$) $\delta$ 7.39–7.18 (m, 5H), 4.08–3.93 (m, 1H), 3.32–3.23 (m, 1H), 3.09 (dd, J=3.1, 13.7 Hz, 1H), 2.59 (dd, J=10.9, 13.7 Hz, 1H), 2.30 (brs, 2H); IR (KBr) 3320, 3300, 3050, 2920, 2860, 2700, 1615 cm$^{-1}$

REFERENCE EXAMPLE 2

Synthesis of (5-benzyloxycarbonylamino-6-oxo-2-phenyl-1,6-dihydro-1-pyrimidinyl)acetic acid.

(1) A solution of benzonitrile (60.0 g, 0.582 mol) in ethanol (500 mL) was saturated by blowing in hydrogen chloride under ice-cooling. The resulting solution was stirred at room temperature for 18 h and the solvent was evaporated under reduced pressure. The obtained crystals were washed with ether and dried in vacuo to give 73.6 g (68%) of ethyl benzimidate hydrochloride as colorless crystals.

(2) To a solution of the target compound in step (1) (72.0 g, 0.388 mol) in ethanol (300 mL) was added aminoacetaldehyde diethyl acetal (68 mL, 0.47 mol) under ice-cooling. The resulting mixture was stirred at 4° C. for 18 h. After evaporation of ethanol under reduced pressure, the condensate obtained was poured into 1N aqueous sodium hydroxide solution (800 mL) and extracted with chloroform. The extract was dried over anhydrous magnesium sulfate. Evaporation of the solvent under reduced pressure gave 141.2 g of a colorless oil containing N-(2,2-diethoxyethyl) benzamidine.

(3) To a solution of the target compound in step (2) (a half of the crude product obtained in the above reaction, 70.6 g) in ethanol (100 mL) was added dropwise diethyl ethoxymethylenemalonate (58 mL, 0.29 mol). The reaction mixture was heated to 100° C. and stirred for 2 h. Then the solvent was evaporated under reduced pressure, and the obtained concentrate was poured into saturated aqueous ammonium chloride solution (600 mL) and extracted with ethyl acetate. The extract was washed with water and dried over anhydrous magnesium sulfate. Concentration followed by separation and purification by silica gel column chromatography (50:50 hexane-ethyl acetate) gave 58.2 g of ethyl 1-(2,2-diethoxyethyl)-2-phenylpyrimidin-6(1H)-one-5-carboxylate as a pale yellow oil.

(4) To a solution of the target compound in step (3) (57.7 g, 0.160 mmol) in tetrahydrofuran (THF) (500 mL) was added 0.5N aqueous sodium hydroxide solution (360 mL). The resulting mixture was stirred at room temperature for 1 h, and then washed with chloroform. After addition of 1N hydrochloric acid (200 mL) to the aqueous layer, the resulting mixture was extracted with chloroform, and the extract was dried over anhydrous magnesium sulfate. Evaporation of the solvent under reduced pressure gave 36.9 g of a yellow oil containing 1-(2,2-diethoxyethyl)-2-phenylpyrimidin-6(1H)-one-5-carboxylic acid.

(5) A solution of diphenylphosphoryl azide (27.5 mL, 0.123 mol) in 1,4-dioxane (100 mL) was heated to 110° C. and a solution of the target compound in step (4) crude product obtained in the above reaction, 36.9 g) and triethylamine (34.0 mL, 0.244 mol) in 1,4-dioxane (300 mL) was added dropwise thereto over 1.5 h. The resulting mixture was refluxed under heating for 1 h, and benzyl alcohol (25 mL, 0.24 mol) was added. The mixture was further refluxed under heating for 14 h, cooled to room temperature, and then concentrated under reduced pressure. The obtained oil was poured into saturated aqueous ammonium chloride solution (500 mL) and extracted with ethyl acetate. The extract was washed with 1N aqueous sodium hydroxide solution (600 mL) and brine, and dried over anhydrous magnesium sulfate. Concentration followed by separation and purification by silica gel column chromatography (hexane-ethyl acetate, 50:50) gave 24.7 g of a mixture of (5-benzyloxycarbonylamino-6-oxo-2-phenyl-1,6-dihydro-1-pyrimidinyl)acetaldehyde diethyl acetal and benzyl alcohol as a pale-brown oil.

(6) A mixture of a solution of the target compound in step (5) (mixture with benzyl alcohol, 24.3 g, 47.1 mmol) in THF (210 mL) and 1N hydrochloric acid (150 mL) was heated to 60° C. and stirred for 18 h. After removal of THF under reduced pressure, the concentrate was neutralized with saturated aqueous sodium hydrogencarbonate solution (pH 7) and then extracted with ethyl acetate. The extract was dried over anhydrous magnesium sulfate, and the solvent was evaporated under reduced pressure to give 22.4 g a pale-brown oil containing (5-benzyloxycarbonylamino-6-oxo-2-phenyl-1,6-dihydro-1-pyrimidinyl)-acetaldehyde.

(7) To a mixture of the target compound in step (6) (crude product obtained in the above reaction, 22.4 g), 2-methyl-2-propanol (300 mL) and 2-methyl-2-butene (50 mL, 0.47 mol) was added a solution of sodium dihydrogenphosphate dihydrate (51.4 g, 0.329 mol) and sodium chlorite (85%, 36.6 g, 0.344 mol) in water (130 mL). The resulting mixture was stirred at room temperature for 3 h. The organic solvents were removed under reduced pressure and the residue was adjusted with 3N hydrochloric acid to pH 3, followed by extraction with chloroform. The extract was dried over anhydrous magnesium sulfate and the solvent was evaporated under reduced pressure to give crystals. The crystals were washed with hexane-ether (1:1) and dried in vacuo to afford 16.0 g of the title compound as colorless crystals.

mp 179–183° C.; $^1$H-NMR (200 MHz, DMSO-$d_6$) δ 13.1 (brs, 1H), 8.99 (s, 1H), 8.47 (s, 1H), 7.2–7.6 (m, 10H), 5.19 (s, 2H), 4.51 (s, 2H); IR (KBr) 3600–2200, 1720, 1655, 1605, 1510 cm$^{-1}$

REFERENCE EXAMPLE 3

Synthesis of [5-benzyloxycarbonylamino-2-(4-fluorophenyl)-6-oxo-1,6-dihydro-1-pyrimidinyl]acetic acid.

(1) Ethyl 4-fluorobenzimidate hydrochloride was synthesized in the same manner as in Reference Example 2. That is, 4-fluorobenzonitrile (50.8 g, 0.407 mol) was treated with hydrogen chloride in ethanol (500 mL) to give 82.1 g (99%) of the target compound as colorless crystals.

(2) N-(2,2-Diethoxyethyl)-4-fluorobenzamidine was synthesized in the same manner as in Reference Example 2. That is, the target compound in step (1) (50.0 g, 0.246 mol) was reacted with aminoacetaldehyde diethyl acetal (43 mL, 0.30 mol) in ethanol (200 mL) to give a colorless, transparent oil containing the target compound.

(3) Ethyl 1-(2,2-diethoxyethyl)-2-(4-fluorophenyl) pyrimidin-6(1H)-one-5-carboxylate was synthesized in the same manner as in Reference Example 2. That is, the target compound in step (2) (crude product obtained in the above reaction) was reacted with diethyl ethoxymethylenemalonate (55 mL, 0.27 mol) in ethanol (100 mL) to give 70.2 g of the target compound as a pale-yellow oil.

(4) To a solution of the target compound in step (3) (55.0 g, 0.145 mol) in pyridine (200 mL) was added lithium iodide (49.0 g, 0.366 mol). The resulting mixture was heated to 100° C. and stirred for 16 h. The organic solvents were removed under reduced pressure. To the residue was added toluene (200 mL), and the trace amount of the remaining pyridine was removed under reduced pressure. After addition of saturated aqueous sodium hydrogencarbonate solution to the residue, the mixture was extracted with ethyl acetate to extract organic matters other than carboxylic acid. After collection of insolubles by filtration, the aqueous layer was adjusted with 3N hydrochloric acid (400 mL) to pH 2, followed by extraction with ethyl acetate. The extract was washed with saturated brine and dried over anhydrous magnesium sulfate. Evaporation of the solvent under reduced pressure gave 14.5 g of 1-(2,2-diethoxyethyl)-2-(4-fluorophenyl)pyrimidin-6(1H)-one-5-carboxylic acid as a pale-yellow oil. The insolubles obtained above were added to 2N hydrochloric acid (500 mL), and the mixture was extracted with ethyl acetate. The extract was washed with saturated brine and dried over anhydrous magnesium sulfate. Evaporation of the solvent under reduced pressure further afforded 29.7 g (total yield 87%) of the target compound as a pale-yellow oil.

(5) [5-Benzyloxycarbonylamino-2-(4-fluorophenyl)-6-oxo-1,6-dihydro-1-pyrimidinyl]acetaldehyde diethyl acetal was synthesized in the same manner as in Reference Example 2. That is, the target compound in step (4) (43.6 g, 0.124 mol) was reacted with diphenylphosphoryl azide (31 mL, 0.14 mol) in 1,4-dioxane (400 mL) in the presence of triethylamine (35 mL, 0.25 mol), and then with benzyl alcohol (26 mL, 0.25 mol), to give 45.2 g (65%) of a mixture of the target compound and benzyl alcohol as a pale-brown oil.

(6) [5-Benzyloxycarbonylamino-2-(4-fluorophenyl)-6-oxo-1,6-dihydro-1-pyrimidinyl]acetaldehyde was synthesized in the same manner as in Reference Example 2. That is, the target compound in step (5) (mixture with benzyl alcohol, 44.6 g, 79.1 mmol) was treated with 1N hydrochloric acid (250 mL) in THF (350 mL) to give 20.7 g (55%) of a mixture of the target compound and benzyl alcohol as a colorless solid.

(7) [5-Benzyloxycarbonylamino-2-(4-fluorophenyl)-6-oxo-1,6-dihydro-1-pyrimidinyl]acetic acid was synthesized in the same manner as in Reference Example 2. That is, the target compound in step (6) (mixture with benzyl alcohol, 20.2 g, 42.3 mmol) was treated with sodium chlorite (85%, 36.6 g, 0.344 mol) in the presence of 2-methyl-2-butene (50 mL, 0.47 mol) and sodium dihydrogenphosphate dihydrate (51.4 g, 0.329 mol), in a mixed solvent of 2-methyl-2-propanol (300 mL) and water (130 mL) to give 15.5 g (86%) of a mixture of the title compound and benzyl alcohol as a colorless solid.

$^1$H-NMR (500 MHz, DMSO-$d_6$) δ 13.3 (brs, 1H), 8.99 (s, 1H), 8.46 (s, 1H), 7.56 (dd, J=8.9, 5.4 Hz, 2H), 7.44 (d, J=7.2 Hz, 2H), 7.30–7.42 (m, 5H), 5.19 (s, 2H), 4.53 (s, 2H); IR (KBr) 3650–2300, 1720, 1660, 1600 cm$^{-1}$

REFERENCE EXAMPLE 4

Synthesis of [5-benzyloxycarbonylamino-6-oxo-2-(p-tolyl)-1,6-dihydro-1-pyrimidinyl]acetic acid.

(1) Ethyl 4-methylbenzimidate hydrochloride was synthesized in the same manner as in Reference Example 2. That is, p-tolunitrile (25.6 g, 0.219 mol) was treated with hydrogen chloride in ethanol (250 mL) to give 42.3 g (97%) of the target compound as colorless crystals.

(2) N-(2,2-Diethoxyethyl)-4-methylbenzamidine was synthesized in the same manner as in Reference Example 2. That is, the target compound in step (1) (25.0 g, 0.125 mol) was reacted with aminoacetaldehyde diethyl acetal (21 mL, 0.14 mol) in ethanol (100 mL) to give 40.0 g of a colorless, transparent oil containing the target compound.

(3) Ethyl 1-(2,2-diethoxyethyl)-2-(p-tolyl)pyrimidin-6(1H)-one-5-carboxylate was synthesized in the same manner as in Reference Example 2. That is, the target compound in step (2) (crude product obtained in the above reaction) was treated with diethyl ethoxymethylenemalonate (28 mL, 0.14 mol) in ethanol (50 mL) to give 36.1 g of the target compound as a pale-yellow oil.

(4) 1-(2,2-Diethoxyethyl)-2-(p-tolyl)pyrimidin-6(1H)-one-5-carboxylic acid was synthesized in the same manner as in Reference Example 3. That is, the target compound in step (3) (35.0 g, 93.5 mmol) was reacted with lithium iodide (30.0 g, 244 mmol) in pyridine (140 mL) to give 24.0 g (74%) of the target compound as pale-brown crystals.

(5) [5-Benzyloxycarbonylamino-6-oxo-2-(p-tolyl)-1,6-dihydro-1-pyrimidinyl]acetaldehyde diethyl acetal was synthesized in the same manner as in Reference Example 2. That is, the target compound in step (4) (23.0 g, 66.4 mmol) was reacted with diphenylphosphoryl azide (16.5 mL, 73.6 mmol) in the presence of triethylamine (18.5 mL, 133 mmol) in 1,4-dioxane (200 mL), and then with benzyl alcohol (10 mL, 97 mmol) to give 29.8 g (86%) of a mixture of the target compound and benzyl alcohol as a colorless solid.

(6) [5-Benzyloxycarbonylamino-6-oxo-2-(p-tolyl)-1,6-dihydro-1-pyrimidinyl]acetaldehyde was synthesized in the same manner as in Reference Example 2. That is, the target compound in step (5) (mixture with benzyl alcohol, 29.1 g, 55.9 mmol) was treated with 1N hydrochloric acid (150 mL) in THF (200 mL) to give 25.3 g of a mixture containing the target compound as a colorless solid.

(7) [5-Benzyloxycarbonylamino-6-oxo-2-(p-tolyl)-1,6-dihydro-1-pyrimidinyl]acetic acid was synthesized in the same manner as in Reference Example 2. That is, the target compound in step (6) (crude product obtained in the above reaction, 25.3 g) was treated with sodium chlorite (85%, 43.4 g, 0.408 mol) in the presence of 2-methyl-2-butene (60 mL, 0.57 mol) and sodium dihydrogenphosphate dihydrate (61.0 g, 0.391 mol) in a mixed solvent of 2-methyl-2-propanol (350 mL) and water (150 mL) to give 17.5 g of the title compound as colorless crystals.

mp 251–254° C.; $^1$H-NMR (500 MHz, DMSO-$d_6$) δ 13.27 (brs, 1H), 8.95 (s, 1H), 8.45 (s, 1H), 7.44 (d, J=7.4 Hz, 2H), 7.37–7.42 (m, 4H), 7.31–7.35 (m, 3H), 5.19 (s, 2H), 4.52 (s, 2H), 2.38 (s, 3H); IR (KBr) 3600–2300, 1735, 1715, 1660, 1605, 1525 cm$^{-1}$

REFERENCE EXAMPLE 5

Synthesis of [5-benzyloxycarbonylamino-6-oxo-2-(m-tolyl)-1,6-dihydro-1-pyrimidinyl]acetic acid.

(1) Ethyl 3-methylbenzimidate hydrochloride was synthesized in the same manner as in Reference Example 2. That is, m-tolunitrile (25.2 g, 0.215 mol) was treated with hydrogen chloride in ethanol (250 mL) to give 41.7 g (97%) of the target compound as colorless crystals.

(2) N-(2,2-Diethoxyethyl)-3-methylbenzamidine was synthesized in the same manner as in Reference Example 2. That is, the target compound in step (1) (25.0 g, 0.125 mol) was reacted with aminoacetaldehyde diethyl acetal (21 mL, 0.14 mol) in ethanol (100 mL) to give 40.1 g of a colorless, transparent oil containing the target compound.

(3) Ethyl 1-(2,2-diethoxyethyl)-2-(m-tolyl)pyrimidin-6 (1H)-one-5-carboxylate was synthesized in the same manner as in Reference Example 2. That is, the target compound in step (2) (crude product obtained in the above reaction) was reacted with diethyl ethoxymethylenemalonate (28 mL, 0.14 mol) in ethanol (50 mL) to give 35.8 g of the target compound as a pale-yellow oil.

(4) 1-(2,2-Diethoxyethyl)-2-(m-tolyl)pyrimidin-6(1H)-one-5-carboxylic acid was synthesized in the same manner as in Reference Example 3. That is, the target compound in step (3) (34.8 g, 92.9 mmol) was reacted with lithium iodide (30.0 g, 244 mmol) in pyridine (140 mL) to give 22.7 g (71%) of the target compound as brown crystals.

(5) [5-Benzyloxycarbonylamino-6-oxo-2-(m-tolyl)-1,6-dihydro-1-pyrimidinyl]acetaldehyde diethyl acetal was synthesized in the same manner as in Reference Example 2. That is, the target compound in step (4) (22.0 g, 63.5 mol) was reacted with diphenylphosphoryl azide (16 mL, 71 mmol) in 1,4-dioxane (200 mL) in the presence of triethylamine (18 mL, 0.13 mol), and then with benzyl alcohol (10 mL, 97 mmol) to give 30.1 g (86%) of a mixture of the target compound and benzyl alcohol as a pale-yellow oil.

(6) [5-Benzyloxycarbonylamino-6-oxo-2-(m-tolyl)-1,6-dihydro-1-pyrimidinyl]acetaldehyde was synthesized in the same manner as in Reference Example 2. That is, the target compound in step (5) (mixture with benzyl alcohol, 29.4 g, 53.6 mmol) was treated with 1N hydrochloric acid (150 mL) in THF (200 mL) to give 26.1 g of a mixture containing the target compound as a colorless solid.

(7) [5-Benzyloxycarbonylamino-6-oxo-2-(m-tolyl)-1,6-dihydro-1-pyrimidinyl]acetic acid was synthesized in the same manner as in Reference Example 2. That is, the target compound in step (6) (crude product obtained in the above reaction, 26.1 g) was treated with sodium chlorite (85%, 41.6 g, 0.391 mol) in the presence of 2-methyl-2-butene (60 mL, 0.57 mol) and sodium dihydrogenphosphate dihydrate (58.5 g, 0.375 mol) in a mixed solvent of 2-methyl-2-propanol (350 mL) and water (150 mL) to give 18.9 g of the title compound as colorless crystals.

mp 183–185° C.; $^1$H-NMR (500 MHz, DMSO-$d_6$) δ 13.27 (brs, 1H), 8.97 (s, 1H), 8.46 (s, 1H), 7.44 (d, J=7.3 Hz, 2H), 7.32–7.42 (m, 5H), 7.31 (s, 1H), 7.27 (d, J=7.4 Hz, 1H), 5.19 (s, 2H), 4.51 (s, 2H), 2.35 (s, 3H); IR (KBr) 3600–2300, 1720, 1655, 1600, 1515 cm$^{-1}$ REFERENCE EXAMPLE 6
Synthesis of N-[4(S)-amino-2,2-difluoro-3(R)-hydroxy-5-phenylpentanoyl]benzylamine.

(1) To a mixture of N-tert-butoxycarbonylphenylalanine (13.3 g, 50.0 mmol), potassium hydrogencarbonate (10.0 g, 100 mmol) and N,N-dimethylformamide (80 mL) was added methyl iodide (5 mL, 80 mmol). The resulting mixture was stirred at room temperature for 5 h, and water (200 mL) was added. The mixture was extracted with ethyl acetate-benzene (1:1), and the organic layer was washed successively with water, 5% aqueous sodium sulfite solution and saturated brine, and dried over anhydrous sodium sulfate. The solvent was evaporated and the obtained residue was separated and purified by silica gel column chromatography (hexane-ethyl acetate, 90:10) to give 13.6 g (96%) of N-tert-butoxycarbonylphenylalanine methyl ester as a colorless oil.

(2) To a solution of the target compound in step (1) (10.8 g, 38.9 mmol) in THF (50 mL) were added anhydrous lithium chloride (3.29 g, 77.3 mmol) and sodium borohydride (2.92 g, 77.3 mmol) under an argon stream. The resulting mixture was stirred at room temperature for 16 h, cooled with ice and adjusted with 10% aqueous citric acid solution to pH 4. THF was removed under reduced pressure. To the residue was added water (100 mL), and the mixture was extracted with dichloromethane. The extract was dried over anhydrous sodium sulfate. The solvent was evaporated and the obtained residue was recrystallized from ethyl acetate-hexane (1:7) to give 9.49 g (97%) of N-tert-butoxycarbonylphenylalaninol as colorless crystals.

(3) To a solution of the target compound in step (2) (7.16 g, 28.5 mmol) in dichloromethane (85 mL) were added successively triethylamine (15.8 mL, 113.9 mmol) and a solution of sulfur trioxidepyridine complex (18.1 g, 113.9 mmol) in dimethylsulfoxide (85 mL). The resulting mixture was stirred at room temperature for 15 min, poured into a mixture of ice and saturated brine (300 mL), and then extracted with cold ether. The organic layer was washed successively with cold 10% aqueous citric acid solution and cold saturated brine, and dried over anhydrous sodium sulfate. The solvent was evaporated and hexane was added to the obtained residue to suspend same. Insolubles were collected by filtration to give 6.41 g (90%) of N-tert-butoxycarbonylphenylalaninal. To a suspension of zinc powder (5.59 g, 85.5 mmol) in THF (1 mL) was added dropwise a solution of the above-mentioned N-tert-butoxycarbonylphenylalaninal (6.41 g, 25.7 mmol) and ethyl bromodifluoroacetate (11.1 mL, 85.5 mmol) in THF (16 mL) with ultrasonication. After 3 hr of ultrasonication, dichloromethane (200 mL) and 1N aqueous potassium hydrogensulfate solution (100 mL) were added. The organic layer was separated and dried over anhydrous sodium sulfate. The solvent was evaporated and the obtained residue was separated and purified by silica gel column chromatography (hexane-ethyl acetate, 75:25) to give 2.60 g (27%) of ethyl 4(S)-[(tert-butoxycarbonyl)amino]-2,2-difluoro-3(R)-hydroxy-5-phenylpentanoate as colorless crystals.

(4) To a solution of the target compound in step (3) (2.00 g, 5.36 mmol) in THF (12 mL) was added 1N aqueous sodium hydroxide solution (5.54 mL, 5.54 mmol). The resulting mixture was stirred at room temperature for 2 h. THF was removed and water (20 mL) was added to the residue. The resulting suspension was lyophilized to give sodium 4(S)-[(tert-butoxycarbonyl)amino]-2,2-difluoro-3(R)-hydroxy-5-phenylpentanoate. To a solution of the compound obtained, hydroxybenzotriazole (HOBT) (1.67 g, 12.3 mmol) and benzylamine (1.15 g, 10.7 mmol) in dichloromethane (30 mL) was added WSCI hydrochloride (1.54 g, 8.04 mmol) under ice-cooling. The resulting mixture was stirred overnight at room temperature. The solvent was evaporated and saturated aqueous sodium hydrogencarbonate solution (50 mL) was added. The mixture was extracted with ethyl acetate, and the organic layers were combined, washed successively with 10% aqueous citric acid solution, saturated aqueous sodium hydrogencarbonate solution and saturated brine, and dried over anhydrous sodium sulfate. The solvent was evaporated and the obtained residue was recrystallized from ethyl acetate-hexane (1:10) to give 1.94 g (84%) of N-[4(S)-[(tert-butoxycarbonyl)amino]-2,2-difluoro-3(R)-hydroxy-5-phenylpentanoyl]benzylamine as colorless crystals.

(5) The target compound in step (4) (1.60 g, 3.68 mmol) was dissolved in a solution (4N, 16 mL) of hydrogen chloride in 1,4-dioxane, and the resulting solution was stirred at room temperature for 1 h. After evaporation of the solvent, ether (5 mL) was added to the residue and then removed. This operation was repeated three times, and to the residue obtained was added saturated aqueous sodium hydrogencarbonate solution (50 mL) under ice-cooling. The mixture was extracted with ethyl acetate, and the organic layer was dried over anhydrous sodium sulfate. The solvent was evaporated and the obtained residue was recrystallized from ethyl acetate-hexane (1:8) to give 1.15 g (94%) of the title compound as colorless crystals.

mp 128–130° C.; $^1$H-NMR (200 MHz, CDCl$_3$) δ 7.40–7.19 (m, 10H), 6.78 (brs, 1H), 4.52 (d, J=5.8 Hz, 2H), 3.86 (dd, J=7.8, 16.5 Hz, 1H), 3.69 (dd, J=5.3, 9.7 Hz, 1H), 2.92 (dd, J=5.3, 13.7 Hz, 1H), 2.66 (dd, J=9.7, 13.7 Hz, 1H), 2.13 (brs, 3H); IR (KBr) 3400, 3320, 3020, 1665, 1615, 1540 cm$^{-1}$

REFERENCE EXAMPLE 7

Synthesis of 2-(3-benzyloxycarbonylamino-5-benzyl-2-oxo-1,2-dihydro-1-pyridyl)acetic acid.

(1) To a mixture of 3-aminopyrid-2-one (24.6 g, 0.223 mol), sodium carbonate (52.1 g, 0.492 mol), THF (250 mL) and 1,4-dioxane (50 mL) was added dropwise benzyloxycarbonyl chloride (35.1 mL, 0.246 mol). The resulting mixture was stirred at room temperature for 15 h. Ethyl acetate (1200 mL) was added and the mixture was washed with water, saturated aqueous sodium hydrogencarbonate solution and saturated brine. After filtering off insolubles, the filtrate was dried over anhydrous magnesium sulfate. The residue obtained by concentration of the extract solution was recrystallized from methanol-ethyl acetate (6:1) to give 21.5 g of 3-benzyloxycarbonylaminopyrid-2-one as colorless crystals. The insolubles obtained were dissolved in chloroformmethanol (10:1), and then washed with saturated brine. The aqueous layer was further extracted with chloroform, and combined with the organic layer obtained earlier. The combined extracts were dried over anhydrous magnesium sulfate. Evaporation of the solvent further afforded 16.7 g (total yield 70%) of the same product as a colorless solid.

(2) To a suspension of the target compound in step (1) (15.6 g, 63.9 mmol) in dichloromethane (300 mL) was added N-iodosuccinimide (15.3 g, 64.4 mmol). The resulting mixture was stirred at room temperature for 17 h, and under ice-cooling for further 2.5 h. The precipitated solid was collected by filtration to give 12.9 g (55%) of 3-benzyloxycarbonylamino-5-iodopyrid-2-one as a colorless solid.

(3) To a suspension of zinc powder (781 mg, 11.9 mmol) in THF (10 mL) was added dropwise a solution of benzyl bromide (0.95 mL, 8.0 mmol) in THF (20 mL) at 18–19° C. over 3 min. The resulting mixture was ultrasonicated at 25–35° C. for 1.5 h with occasional stirring, and then further stirred at room temperature for 1.5 h. After addition of [1,1'-bis(diphenylphosphino)ferrocene]palladium(II) chloride (172 mg, 0.211 mmol), a solution of the target compound in step (2) (737 mg, 1.99 mmol) in THF (25 ml) was added over 6 min, the mixture was stirred at 27° C. for 25 min, at 51–56° C. for 2 h, and at room temperature for 14 h. The reaction mixture was poured into 1N hydrochloric acid (150 mL), and then extracted with ethyl acetate. The extract was washed with saturated brine and dried over anhydrous magnesium sulfate. The residue obtained by concentration of the extract was separated and purified by silica gel column chromatography (dichloromethane-ethyl acetate, 4:1) to give 542 mg (81%) of 5-benzyl-3-benzyloxycarbonylaminopyrid-2-one as a brown solid.

(4) To a suspension of sodium hydride (60% in oil, 77.9 mg, 1.95 mmol) in N,N-dimethylformamide (DMF) (2.5 mL) was added dropwise a solution of the target compound in step (3) (512 mg, 1.53 mmol) in DMF (5 mL) at 21–25° C. over 6 min. The resulting mixture was stirred at the same temperature for 40 min, and ethyl iodoacetate (0.19 mL, 1.6 mmol) was added dropwise at 12° C. over 1 min. The resulting mixture was stirred at 25–26° C. for 16 h, poured into 1N hydrochloric acid (30 mL), and then extracted with ethyl acetate. The extract was washed with saturated brine and dried over anhydrous magnesium sulfate. The residue obtained by concentration of the extract was separated and purified by silica gel column chromatography (dichloromethane-ethyl acetate, 95:5) to give 460 mg (72%) of ethyl 2-(3-benzyloxycartonylamino-5-benzyl-2-oxo-1,2-dihydro-1-pyridyl)acetate as a colorless solid.

(5) To a suspension of the target compound in step (4) (438 mg, 1.04 mmol) in methanol (20 mL) was added 2N aqueous sodium hydroxide solution (2.6 mL). The resulting mixture was stirred at room temperature for 5 min. 1,4-Dioxane (6 mL) was added and the mixture was stirred at room temperature for 2.5 h. The reaction mixture was cooled with ice, acidified with 1N hydrochloric acid (20 mL), and then extracted with chloroform. The extract was washed with saturated brine and dried over anhydrous magnesium sulfate. Evaporation of the solvent afforded 401 mg (98%) of the title compound as a colorless solid.

$^1$H-NMR (200 MHz, DMSO-$d_6$) δ 8.38 (s, 1H), 7.74 (d, J=1.9 Hz, 1H), 7.45–7.10 (m, 11H), 5.13 (s, 2H), 4.64 (s, 2H), 3.70 (s, 2H); IR (KBr) 3350, 3000, 2875, 1715, 1650, 1575, 1520 cm$^{-1}$

REFERENCE EXAMPLE 8

Synthesis of N-[1-benzyl-2-(tert-butyldimethylsilyl)oxy-3,3,3-trifluoropropyl]-2-iodoacetamide.

(1) To a solution of 3-amino-1,1,1-trifluoro-4-phenyl-2-butanol (title compound in Reference Example 1: 15.0 g, 68.4 mmol) and triethylamine (10.0 mL, 71.7 mmol) in THF (340 mL) was added a solution of chloroacetyl chloride (5.5 mL, 69 mmol) in THF (30 mL). The resulting mixture was stirred at room temperature for 20 h under a nitrogen atmosphere, diluted with ethyl acetate (400 mL), and further stirred at room temperature for 1 h. Insolubles were then removed by filtration and washed with ethyl acetate. The filtrate was poured into 1N hydrochloric acid (800 mL), and then extracted with ethyl acetate. The extract was washed with water, saturated aqueous sodium hydrogencarbonate solution and saturated brine, and dried over anhydrous magnesium sulfate. The extract was concentrated to give 20.5 g of N-(1-benzyl-3,3,3-trifluoro-2-hydroxypropyl)-2-chloroacetamide as a colorless solid.

(2) To a mixture of the target compound in step (1) (crude product obtained in the above reaction, 20.5 g), 2,6-lutidine (16.0 mL, 137 mmol) and dichloromethane (150 mL) was added tert-butyldimethylsilyl triflate (23.0 mL, 100 mmol). The resulting mixture was stirred at room temperature for 16 h, poured into 1N hydrochloric acid (600 mL), and then extracted with ethyl acetate. The extract was washed with saturated aqueous sodium hydrogencarbonate solution and saturated brine, and dried over anhydrous magnesium sulfate. The residue was concentrated under reduced pressure and separated and purified by silica gel column chromatography (hexane-ethyl acetate, 89:11) to give 25.2 g of N-[1-benzyl-2-(tert-butyldimethylsilyl)oxy-3,3,3-trifluoropropyl]-2-chloroacetamide as a colorless solid.

(3) A solution of the target compound in step (2) (24.3 g, 59.3 mmol) and sodium iodide (26.6 g, 177 mmol) in acetone (180 mL) was stirred at room temperature for 18 h. After removal of acetone under reduced pressure, the concentrate was dissolved in ethyl acetate, poured into water (500 mL), and extracted with ethyl acetate. The extract was washed with saturated brine and dried over anhydrous magnesium sulfate. The residue was concentrated under reduced pressure and separated and purified by silica gel column chromatography (hexane:ethyl acetate, 83:17) to give 29.2 g (98%) of the title compound as a colorless solid.

$^1$H-NMR (500 MHz, DMSO-d$_6$) δ 8.29 (d, J=7.8 Hz, 1H), 7.28 (t, J=7.6 Hz, 2H), 7.17–7.23 (m, 3H), 4.27 (dq, J=7.2, 4.0 Hz, 1H), 4.11 (m, 1H), 3.57 (m, 2H), 2.97 (dd, J=14.5, 2.2 Hz, 1H), 2.68 (dd, J=14.5, 11.5 Hz, 1H), 0.93 (s, 9H), 0.19 (s, 3H), 0.11 (s, 3H); IR (KBr) 3280, 2920, 2890, 1650, 1550 cm$^{-1}$

REFERENCE EXAMPLE 9

Synthesis of 3-benzyloxycarbonylamino-6-phenylpyrid-2-one.

(1) A solution of acetophenone (26.3 mL, 0.225 mol) and N,N-dimethylformamide dimethyl acetal (100 mL, 0.753 mol) in acetonitrile (450 mL) was refluxed under heating for 14 h. After cooling, the reaction mixture was concentrated to give a yellow semi-solid. To a solution of the yellow semi-solid obtained in DMF (350 mL) were added cyanoacetamide (17.1 g, 0.204 mol) and sodium methoxide (23.9 g, 0.442 mol). The resulting mixture was stirred at 100–110° C. for 5 h and then cooled with ice-water. Water (1100 mL) was added and then 10% hydrochloric acid was added to adjust the mixture to pH 5. The precipitated solid was collected by filtration with suction and dried by placing same in an air stream overnight to give 11.2 g (25%) of 6-phenylpyrid-2-one-3-carbonitrile as a yellow solid.

(2) A mixture of the target compound in step (1) (11.1 g, 56.6 mmol), 47% hydrobromic acid (37 mL) and acetic acid (80 mL) was refluxed under heating for 12 h, cooled to room temperature and diluted with water (37 mL). Then the pH was adjusted to 5 with 10% aqueous sodium hydroxide solution. The precipitated solid was collected by filtration with suction and washed with 10% hydrochloric acid and water. Saturated aqueous sodium hydrogencarbonate solution (400 mL) and 1N aqueous sodium hydroxide solution (300 mL) were added and the resulting mixture was washed with chloroform. The aqueous layer was adjusted with conc. hydrochloric acid to pH 3–4 under ice-cooling, and then precipitated solid was collected by filtration. The solid was washed with water, and dried at 40° C. for 14 h under reduced pressure to give 6.91 g (57%) of 6-phenylpyrid-2-one-3-carboxylic acid as a colorless solid.

(3) 3-Benzyloxycarbonylamino-6-phenylpyrid-2-one was synthesized in the same manner as in Reference Example 2. That is, the target compound in step (2) (6.78 g, 31.5 mmol) was treated with diphenylphosphoryl azide (7.45 mL, 34.6 mmol) in the presence of triethylamine (5.29 mL, 38.0 mmol) in 1,4-dioxane (175 mL), and reacted with benzyl alcohol (6.25 mL, 63.0 mmol) to give 5.33 g (53%) of the title compound as a pale yellowish brown solid.

$^1$H-NMR (200 MHz, DMSO-d$_6$) δ 12.18 (brs, 1H), 8.45 (s, 1H), 7.93 (d, J=7.7 Hz, 1H), 7.66–7.74 (m, 2H), 7.32–7.51 (m, 8H), 6.61 (d, J=7.7 Hz, 1H), 5.19 (s, 2H); IR (KBr) 3380, 1725, 1640, 1520, 1500 cm$^{-1}$

REFERENCE EXAMPLE 10

Synthesis of (5-benzyloxycarbonylamino-6-oxo-1,6-dihydro-1-pyrimidinyl)acetic acid.

(1) To a solution of benzoyl chloride (70.3 g, 0.500 mol) in ether (330 mL) was added dropwise a solution of formamide (22.5 g, 0.500 mol) in ethanol (23.0 g, 0.499 mol) over 1 h under ice-cooling. The resulting mixture was stirred at 0° C. for 30 min, and precipitates were collected by filtration, washed with ether and dried in vacuo to give 30.1 g (55%) of ethyl formimidate hydrochloride as a colorless solid.

(2) N-(2,2-Diethoxyethyl)formamidine was synthesized in the same manner as in Reference Example 2. That is, the target compound in step (1) (30.1 g, 0.275 mol) was reacted with aminoacetaldehyde diethyl acetal (36.6 g, 0.275 mol) in ethanol (250 mL) to give 48.9 g of a colorless, transparent oil containing the target compound.

(3) Ethyl (2,2-diethoxyethyl)pyrimidin-6(1H)-one-5-carboxylate was synthesized in the same manner as in Reference Example 2. That is, the target compound in step (2) (crude product obtained in the above reaction, 48.9 g) was reacted with diethyl ethoxymethylenemalonate (55 mL, 0.27 mol) in ethanol (100 mL) to give 12.2 g of the target compound as a pale-yellow oil.

(4) 1-(2,2-Diethoxyethyl)pyrimidin-6(1H)-one-5-carboxylic acid was synthesized in the same manner as in Reference Example 3. That is, the target compound in step (3) (11.9 g, 41.9 mmol) was reacted with lithium iodide (14.0 g, 105 mmol) in pyridine (80 mL) to give 8.19 g (76%) of the target compound as a brown solid.

(5) (5-Benzyloxycarbonylamino-6-oxo-1,6-dihydro-1-pyrimidinyl)-acetaldehyde diethyl acetal was synthesized in the same manner as in Reference Example 2. That is, the target compound in step (4) (8.00 g, 31.2 mmol) was reacted with diphenylphosphoryl azide (7.7 mL, 34 mmol) in the presence of triethylamine (8.7 mL, 62 mmol) in 1,4-dioxane (100 mL), and with benzyl alcohol (4.8 mL, 46 mmol) to give 7.97 g (71%) of the target compound as a colorless solid.

(6) (5-Benzyloxycarbonylamino-6-oxo-1,6-dihydro-1-pyrimidinyl)-acetaldehyde was synthesized in the same manner as in Reference Example 2. That is, the target compound in step (5) (7.80 g, 21.6 mmol) was treated with 1N hydrochloric acid (60 mL) in THF (80 mL) to give 5.57 g of a colorless solid containing the target compound.

(7) (5-Benzyloxycarbonylamino-6-oxo-1,6-dihydro-1-pyrimidinyl)acetic acid was synthesized in the same manner as in Reference Example 2. That is, the target compound in step (6) (crude product obtained in the above reaction, 5.57 g) was treated with sodium chlorite (85%, 15.5 g, 0.146 mol) in the presence of 2-methyl-2-butene (21 mL, 0.20 mol) and sodium dihydrogenphosphate dihydrate (21.8 g, 0.140 mol) in a mixed solution of 2-methyl-2-propanol (150 mL) and water (60 mL) to give 4.82 g of the title compound as colorless crystals.

mp 216–220° C.; $^1$H-NMR (500 MHz, DMSO-d$_6$) δ 13.3 (brs, 1H), 8.88 (s, 1H), 8.36 (s, 1H), 8.22 (s, 1H), 7.42 (d, J=7.1 Hz, 2H), 7.38 (t, J=7.1 Hz, 2H), 7.33 (t, J=7.1 Hz, 1H), 5.17 (s, 2H), 4.70 (s, 2H); IR (KBr) 3400, 3250, 1720, 1650, 1605, 1525 cm$^{-1}$

REFERENCE EXAMPLE 11

Synthesis of (5-benzyloxycarbonylamino-2-methyl-6-oxo-1,6-dihydro-1-pyrimidinyl)acetic acid.

(1) N-(2,2-Diethoxyethyl)acetamidine was synthesized in the same manner as in Reference Example 2. That is, ethyl acetimidate hydrochloride (25.0 g, 0.202 mol) was reacted with aminoacetaldehyde diethyl acetal (31 mL, 0.21 mol) in ethanol (150 mL) to give 44.1 g of a pale-green oil containing the target compound.

(2) Ethyl 1-(2,2-diethoxyethyl)-2-methylpyrimidin-6 (1H)-one-5-carboxylate was synthesized in the same manner as in Reference Example 2. That is, The target compound in step (1) (crude product obtained in the above reaction, 44.1 g) was reacted with diethyl ethoxymethylenemalonate (43 mL, 0.21 mol) in ethanol (75 mL) to give 34.1 g (57% yield from ethyl acetimidate hydrochloride) of the target compound as a yellow solid.

(3) 1-(2,2-Diethoxyethyl)-2-methylpyrimidin-6(1H)-one-5-carboxylic acid was synthesized in the same manner as in Reference Example 3. That is, the target compound in step (2) (33.9 g, 114 mmol) was reacted with lithium iodide (36.6 g, 251 mmol) in pyridine (170 mL) to give 14.7 g (48%) of the target compound as a pale-brown solid.

(4) (5-Benzyloxycarbonylamino-2-methyl-6-oxo-1,6-dihydro-1-pyrimidinyl]acetaldehyde diethyl acetal was synthesized in the same manner as in Reference Example 2. That is, the target compound in step (3) (14.3 g, 52.9 mmol) was reacted with diphenylphosphoryl azide (13.5 mL, 60.2 mmol) in the presence of triethylamine (15.0 mL, 107 mmol) in 1,4-dioxane (170 mL), and then with benzyl alcohol (8.2 mL, 79 mmol) to give 14.8 g (75%) of the target compound as a colorless, transparent oil.

(5) (5-Benzyloxycarbonylamino-2-methyl-6-oxo-1,6-dihydro-1-pyrimidinyl)acetaldehyde was synthesized in the same manner as in Reference Example 2. That is, the target compound in step (4) (14.6 g, 38.9 mmol) was treated with 1N hydrochloric acid (100 mL) in THF (140 mL) to give 12.0 g of a dark brown amorphous containing the target compound.

(6) (5-Benzyloxycarbonylamino-2-methyl-6-oxo-1,6-dihydro-1-pyrimidinyl)acetic acid was synthesized in the same manner as in Reference Example 2. That is, the target compound in step (5) (crude product obtained in the above reaction, 12.0 g) was treated with sodium chlorite (85%, 30.2 g, 284 mmol) in the presence of 2-methyl-2-butene (41 mL, 0.39 mol) and sodium dihydrogenphosphate dehydrate (42.5 g, 272 mmol) in a mixed solvent of 2-methyl-2-propanol (250 mL) and water (110 mL) to give 10.8 g of the title compound as a colorless solid.

$^1$H-NMR (500 MHz, DMSO-$d_6$) δ 12.8 (brs, 1H), 8.73 (s, 1H), 8.23 (s, 1H), 7.43–7.35 (m, 4H), 7.33 (t, J=7.1 Hz, 1H), 5.15 (s, 2H), 4.78 (s , 2H), 2.41 (s, 3H); IR (KBr) 3600–2200, 1710, 1650, 1605, 1520 cm$^{-1}$

REFERENCE EXAMPLE 12

Synthesis of [5-benzyloxycarbonylamino-6-oxo-2-(o-tolyl)-1,6-dihydro-1-pyrimidinyl]acetic acid.

(1) To a solution of o-toluamide (13.5 g, 0.100 mol) in dichloromethane (150 mL) was added a solution (1.0 M, 106 mL, 0.106 mol) of triethyloxonium tetrafluoroborate in dichloromethane. The resulting mixture was stirred at room temperature for 14 h. Two-thirds of dichloromethane was evaporated under reduced pressure. After addition of ether (400 mL) to the concentrate, the mixture was stirred for 3 h under ice-cooling. Precipitates were collected by filtration, washed with ether, and dried in vacuo to give 21.7 g (86%) of ethyl 2-methylbenzimidate hydrotetrafluoroborate as a colorless solid.

(2) To a solution of the target compound in step (1) (6.25 g, 24.9 mmol) in ethanol (30 mL) was added dropwise monoethanolamine (1.80 mL, 29.8 mmol). The resulting mixture was stirred at room temperature for 15 h. Ethanol was evaporated under reduced pressure. The obtained concentrate was poured into 1N aqueous sodium hydroxide solution (150 mL) and extracted with chloroform. The extract was dried over anhydrous magnesium sulfate, and the solvent was evaporated under reduced pressure to give 5.31 g of a colorless, transparent oil containing N-(2-hydroxyethyl)-2-methylbenzamidine.

(3) Ethyl 1-(2-hydroxyethyl)-2-(o-tolyl)pyrimidin-6(1H)-one-5-carboxylate was synthesized in the same manner as in Reference Example 2. That is, the target compound in step (2) (crude product obtained in the above reaction, 5.31 g) was reacted with diethyl ethoxymethylenemalonate (6.0 mL, 30 mmol) in ethanol (14 mL) to give 4.52 g of the target compound as a colorless solid.

(4) To a solution of the target compound in step (3) (4.13 g, 13.7 mmol) and 2,6-lutidine (2.3 mL, 20 mmol) in dichloromethane (50 mL) was added tert-butyldimethylsilyl triflate (4.0 mL, 17 mmol). The resulting mixture was stirred at room temperature for 8 h, poured into 1N hydrochloric acid (150 mL), and then extracted with chloroform. The extract was washed with saturated aqueous sodium hydrogen-carbonate solution (150 mL) and saturated brine, and dried over anhydrous magnesium sulfate. The residue was concentrated under reduced pressure, and separated and purified by silica gel column chromatography (chloroform) to give 5.70 g (100%) of ethyl 1-[2-(tert-butyldimethylsilyl)oxyethyl]-2-(o-tolyl)pyrimidin-6(1H)-one-5-carboxylate as a colorless solid.

(5) 1-[2-(tert-Butyldimethylsilyl)oxyethyl]-2-(o-tolyl)pyrimidin-6(1H)-one-5-carboxylic acid was synthesized in the same manner as in Reference Example 3. That is, the target compound in step (4) (11.3 g, 27.1 mmol) was reacted with lithium iodide (11.6 g, 86.7 mmol) in pyridine (55 mL) to give 7.21 g (68%) of the target compound as a colorless solid.

(6) 1-(tert-Butyldimethylsilyl)oxy-2-[5-benzyloxycarbonylamino-6-oxo-2-(o-tolyl)-1,6-dihydro-1-pyrimidinyl]ethane was synthesized in the same manner as in Reference Example 2. That is, the target compound in step (5) (6.86 g, 17.7 mmol) was reacted with diphenylphosphoryl azide (4.8 mL, 21 mmol) in the presence of triethylamine (4.9 mL, 35 mol) in 1,4-dioxane (70 mL), and then with benzyl alcohol (2.7 mL, 26 mmol) to give 5.66 g (44%) of a mixture of the target compound and benzyl alcohol as a pale-yellow oil.

(7) To a solution of the target compound in step (6) (mixture with benzyl alcohol, 5.66 g, 7.86 mmol) in THF (40 mL) was added a solution (1.0 M, 10 mL, 10 mmol) of tetrabutylammonium fluoride in THF. The resulting mixture was stirred at room temperature for 5 h, poured into water (150 mL), and then extracted with ethyl acetate. The extract was washed with saturated brine and dried over anhydrous magnesium sulfate. The residue was concentrated under reduced pressure, and separated and purified by silica gel column chromatography (ethyl acetate-hexane, 50:50) to give 2.95 g (99%) of 2-[5-benzyloxycarbonylamino-6-oxo-2-(o-tolyl)-1,6-dihydro-1-pyrimidinyl]ethanol as a colorless amorphous.

(8) To a solution of the target compound in step (7) (2.83 g, 7.46 mmol) and triethylamine (3.1 mL, 22 mmol) in dichloromethane (25 mL) was added a solution of sulfur trioxide-pyridine complex (3.56 g, 22.4 mmol) in dimethyl sulfoxide (25 mL) under ice-cooling. The resulting mixture was stirred at 0° C. for 4 h, poured into ice-cooled saturated brine (100 mL), and then extracted with ethyl acetate. The extract was washed with 0.5N hydrochloric acid (100 mL) and saturated brine, and dried over anhydrous magnesium sulfate. Concentration under reduced pressure gave 2.72 g (97%) of [5-benzyloxycarbonylamino-6-oxo-2-(o-tolyl)-1,6-dihydro-1-pyrimidinyl]acetaldehyde as a colorless amorphous.

(9) [5-Benzyloxycarbonylamino-6-oxo-2-(o-tolyl)-1,6-dihydro-1-pyrimidinyl]acetic acid was synthesized in the same manner as in Reference Example 2. That is, the target compound in step (8) (2.60 g, 6.89 mmol) was treated with sodium chlorite (85%, 5.35 g, 50.3 mmol) in the presence of 2-methyl-2-butene (7.3 mL, 69 mmol) and sodium dihydrogenphosphate dihydrate (7.52 g, 48.2 mmol) in a mixed solvent of 2-methyl-2-propanol (45 mL) and water (20 mL) to give 2.43 g (90%) of the title compound as colorless crystals.

mp 191–193° C.; $^1$H-NMR (500 MHz, DMSO-d$_6$) δ 13.2 (brs, 1H), 9.00 (s, 1H), 8.48 (s, 1H), 7.47–7.29 (m, 8H), 7.26 (d, J=7.1 Hz, 1H), 5.20 (s, 2H), 4.55 (d, J=17.2 Hz, 1H), 4.20 (d, J=17.2 Hz, 1H), 2.15 (s, 3H); IR (KBr) 3600–2200, 1730, 1655, 1605, 1515 cm$^{-1}$

REFERENCE EXAMPLE 13

Synthesis of [5-benzyloxycarbonylamino-2-(4-chlorophenyl)-6-oxo-1,6-dihydro-1-pyrimidinyl]acetic acid.

(1) Ethyl 4-chlorobenzimidate hydrochloride was synthesized in the same manner as in Reference Example 2. That is, p-chlorobenzonitrile (25.6 g, 0.186 mol) was reacted with hydrogen chloride in ethanol (250 mL) to give 36.8 g (90%) of the target compound as colorless crystals.

(2) 4-Chloro-N-(2,2-diethoxyethyl)benzamidine was synthesized in the same manner as in Reference Example 2. That is, the target compound in step (1) (35.6 g, 0.162 mol) was reacted with aminoacetaldehyde diethyl acetal (26 mL, 0.18 mol) in ethanol (120 mL) to give 48.3 g of a pale-yellow oil containing the target compound.

(3) Ethyl 2-(4-chlorophenyl)-1-(2,2-diethoxyethyl) pyrimidin-6(1H)-one-5-carboxylate was synthesized in the same manner as in Reference Example 2. That is, the target compound in step (2) (crude product obtained in the above reaction, 48.3 g) was reacted with diethyl ethoxymethylenemalonate (36 mL, 0.18 mol) in ethanol (70 mL) to give 46.3 g of the target compound as a pale-yellow oil.

(4) 2-(4—Chlorophenyl)-1-(2,2-diethoxyethyl) pyrimidin-6(1H)-one-5-carboxylic acid was synthesized in the same manner as in Reference Example 3. That is, the target compound in step (3) (45.7 g, 116 mmol) was reacted with lithium iodide (37.2 g, 278 mmol) in pyridine (165 mL) to give 33.0 g (78%) of the target compound as pale-brown crystals.

(5) [5-Benzyloxycarbonylamino-2-(4-chlorophenyl)-6-oxo-1,6-dihydro-1-pyrimidinyl]acetaldehyde diethyl acetal was synthesized in the same manner as in Reference Example 2. That is, the target compound in step (4) (32.2 g, 87.8 mmol) was reacted with diphenylphosphoryl azide (21.5 mL, 95.9 mmol) in the presence of triethylamine (24.5 mL, 176 mmol), and then with benzyl alcohol (12 mL, 0.16 mol) to give 39.3 g (85%) of a mixture of the target compound and benzyl alcohol as a colorless solid.

(6) [5-Benzyloxycarbonylamino-2-(4-chlorophenyl)-6-oxo-1,6-dihydro-1-pyrimidinyl]acetaldehyde was synthesized in the same manner as in Reference Example 2. That is, the target compound in step (5) (mixture with benzyl alcohol, 38.7 g, 73.9 mmol) was treated with 1N hydrochloric acid (190 mL) in THF (250 mL) to give 36.8 g of a mixture containing the target compound as a colorless solid.

(7) [5-Benzyloxycarbonylamino-2-(4-chlorophenyl)-6-oxo-1,6-dihydro-1-pyrimidinyl]acetic acid was synthesized in the same manner as in Reference Example 2. That is, the target compound in step (6) (crude product obtained in the above reaction, 36.8 g) was treated with sodium chlorite (80%, 58.5 g, 517 mmol) in the presence of 2-methyl-2-butene (78 mL, 0.74 mol) and sodium dihydrogenphosphate dihydrate (84.2 g, 540 mmol) in a mixed solvent of 2-methyl-2-propanol (460 mL) and water (190 mL) to give 26.6 g of the title compound as colorless crystals.

mp 220–224° C.; $^1$H-NMR (500 MHz, DMSO-d$_6$) δ 13.29 (brs, 1H), 9.01 (s, 1H), 8.47 (s, 1H), 7.60 (d, J=8.5 Hz, 2H), 7.53 (d, J=8.5 Hz, 2H), 7.44 (d, J=7.1 Hz, 2H), 7.39 (t, J=7.1 Hz, 2H), 7.34 (t, J=7.1 Hz, 1H), 5.19 (s, 2H), 4.53 (s, 2H); IR (KBr) 3320, 1725, 1665, 1610, 1515 cm$^{-1}$

REFERENCE EXAMPLE 14

Synthesis of [5-benzyloxycarbonylamino-2-(4-methoxyphenyl)-6-oxo-1,6-dihydro-1-pyrimidinyl]acetic acid.

(1) Ethyl 4-methoxybenzimidate hydrochloride was synthesized in the same manner as in Reference Example 2. That is, anisonitrile (25.6 g, 0.199 mol) was treated with hydrogen chloride in ethanol (250 mL) to give 40.5 g (94%) of the target compound as pale-red crystals.

(2) N-(2,2-Diethoxyethyl)-4-methoxybenzamidine was synthesized in the same manner as in Reference Example 2. That is, the target compound in step (1) (38.8 g, 0.180 mol) was treated with aminoacetaldehyde diethyl acetal (29 mL, 0.20 mol) in ethanol (130 mL) to give 60.2 g of a colorless, transparent oil containing the target compound.

(3) Ethyl 1-(2,2-diethoxyethyl)-2-(4-methoxyphenyl) pyrimidin-6(1H)-one-5-carboxylate was synthesized in the same manner as in Reference Example 2. That is, the target compound in step (2) (crude product obtained in the above reaction, 60.2 g) was reacted with diethyl ethoxymethylenemalonate (40.5 mL, 0.200 mol) in ethanol (70 mL) to give 33.6 g of the target compound as a pale-yellow oil.

(4) 1-(2,2-Diethoxyethyl)-2-(4-methoxyphenyl) pyrimidin-6(1H)-one-5-carboxylic acid was synthesized in the same manner as in Reference Example 3. That is, the target compound in step (3) (33.0 g, 84.5 mmol) was reacted with lithium iodide (27.1 g, 202 mmol) in pyridine (120 mL) to give 25.1 g (82%) of the target compound as colorless crystals.

(5) [5-Benzyloxycarbonylamino-2-(4-methoxyphenyl)-6-oxo-1,6-dihydro-1-pyrimidinyl]acetaldehyde diethyl acetal was synthesized in the same manner as in Reference Example 2. That is, the target compound in step (4) (24.6 g, 67.9 mmol) was reacted with diphenylphosphoryl azide (16.8 mL, 74.9 mmol) in the presence of triethylamine (19 mL, 0.14 mol) in 1,4-dioxane (200 mL), and then with benzyl alcohol (9.1 mL, 88 mmol) to give 18.8 g (59%) of the target compound as colorless crystals.

(6) [5-Benzyloxycarbonylamino-2-(4-methoxyphenyl)-6-oxo-1,6-dihydro-1-pyrimidinyl]acetaldehyde was synthesized in the same manner as in Reference Example 2. That is, the target compound in step (5) (18.1 g, 38.7 mol) was treated with 1N hydrochloric acid (100 mL) in THF (130 mL) to give 16.5 g of a mixture containing the target compound, as a colorless solid.

(7) [5-Benzyloxycarbonylamino-2-(4-methoxyphenyl)-6-oxo-1,6-dihydro-1-pyrimidinyl]acetic acid was synthesized in the same manner as in Reference Example 2. That is, the target compound in step (6) (crude product obtained in the above reaction, 16.5 g) was treated with sodium chlorite (85%, 28.8 g, 271 mmol) in the presence of 2-methyl-2-butene (41 mL, 0.39 mol) and sodium dihydrogenphosphate dihydrate (44.1 g, 283 mmol) in a mixed solvent of 2-methyl-2-propanol (240 mL) and water (100 mL) to give 14.4 g of the title compound as colorless crystals.

mp 195–200° C.; $^1$H-NMR (500 MHz, DMSO-$d_6$) δ 13.2 (brs, 1H), 8.93 (s, 1H), 8.44 (s, 1H), 7.47–7.42 (m, 4H), 7.39 (t, J=7.1 Hz, 2H), 7.34 (t, J=7.1 Hz, 1H), 7.07 (d, J=8.8 Hz, 2H), 5.19 (s, 2H), 4.54 (s, 2H), 3.82 (s, 3H); IR (KBr) 3300, 1725, 1660, 1600 cm$^{-1}$

REFERENCE EXAMPLE 15

Synthesis of [5-benzyloxycarbonylamino-2-(4-nitrophenyl)-6-oxo-1,6-dihydro-1-pyrimidinyl]acetic acid.

(1) Ethyl 4-nitrobenzimidate hydrochloride was synthesized in the same manner as in Reference Example 2. That is, 4-nitrobenzonitrile (26.5 g, 0.179 mol) was reacted with hydrogen chloride in ethanol (250 mL) to give 35.7 g (86%) of the target compound as colorless crystals.

(2) N-(2,2-Diethoxyethyl)-4-nitrobenzamidine was synthesized in the same manner as in Reference Example 2. That is, the target compound in step (1) (34.7 g, 0.150 mol) was reacted with aminoacetaldehyde diethyl acetal (24 mL, 0.17 mol) in ethanol (120 mL) to give 42.4 g of a pale-yellow solid containing the target compound.

(3) Ethyl 1-(2,2-diethoxyethyl)-2-(4-nitrophenyl)pyrimidin-6(1H)-one-5-carboxylate was synthesized in the same manner as in Reference Example 2. That is, the target compound in step (2) (crude product obtained in the above reaction, 42.4 g) was reacted with diethyl ethoxymethylenemalonate (34 mL, 0.17 mol) in ethanol (65 mL) to give 49.0 g of the target compound as pale-yellow crystals.

(4) 1-(2,2-Diethoxyethyl)-2-(4-nitrophenyl)pyrimidin-6(1H)-one-5-carboxylic acid was synthesized in the same manner as in Reference Example 3. That is, the target compound in step (3) (48.1 g, 0.119 mol) was reacted with lithium iodide (38.1 g, 0.285 mol) in pyridine (160 mL) to give 26.7 g (59%) of the target compound as colorless crystals.

(5) [5-Benzyloxycarbonylamino-2-(4-nitrophenyl)-6-oxo-1,6-dihydro-1-pyrimidinyl]acetaldehyde diethyl acetal was synthesized in the same manner as in Reference Example 2. That is, the target compound in step (4) (26.2 g, 69.4 mmol) was reacted with diphenylphosphoryl azide (17.9 mL, 79.8 mmol) in the presence of triethylamine (19 mL, 0.14 mol) in 1,4-dioxane (220 mL), and then with benzyl alcohol (10.5 mL, 0.101 mol) to give 24.5 g (73%) of the target compound as pale-yellow crystals.

(6) [5-Benzyloxycarbonylamino-2-(4-nitrophenyl)-6-oxo-1,6-dihydro-1-pyrimidinyl]acetaldehyde was synthesized in the same manner as in Reference Example 2. That is, the target compound in step (5) (24.0 g, 49.7 mmol) was treated with 1N hydrochloric acid (140 mL) in THF (185 mL) to give 20.4 g (100%) of the target compound as pale-yellow crystals.

(7) [5-Benzyloxycarbonylamino-2-(4-nitrophenyl)-6-oxo-1,6-dihydro-1-pyrimidinyl]acetic acid was synthesized in the same manner as in Reference Example 2. That is, the target compound in step (6) (20.2 g, 49.5 mmol) was treated with sodium chlorite (85%, 36.9 g, 347 mmol) in the presence of 2-methyl-2-butene (52 mL, 0.49 mol) and sodium dihydrogenphosphate dihydrate (56.4 g, 362 mmol) in a mixed solvent of 2-methyl-2-propanol (310 mL) and water (130 mL) to give 20.3 g (97%) of the title compound as colorless crystals.

mp 240–243° C.; $^1$H-NMR (500 MHz, DMSO-$d_6$) δ 13.3 (brs, 1H), 9.10 (s, 1H), 8.51 (s, 1H), 8.37 (d, J=8.8 Hz, 2H), 7.79 (d, J=8.8 Hz, 2H), 7.45 (d, J=7.1 Hz, 2H), 7.40 (t, J=7.1 Hz, 2H), 7.34 (t, J=7.1 Hz, 1H), 5.20 (s, 2H), 4.53 (s, 2H); IR (KBr) 3650–2800, 1720, 1670, 1610, 1530, 1505 cm$^{-1}$

REFERENCE EXAMPLE 16

Synthesis of [5-benzyloxycarbonylamino-2-(3,5-dinitrophenyl)-6-oxo-1,6-dihydro-1-pyrimidinyl]acetic acid.

(1) Ethyl 3,5-dinitrobenzimidate hydrochloride was synthesized in the same manner as in Reference Example 2. That is, 3,5-dinitrobenzonitrile (25.2 g, 0.130 mol) was treated with hydrogen chloride in ethanol (250 mL) to give 34.5 g (96%) of the target compound as pale-brown crystals.

(2) N-(2,2-Diethoxyethyl)-3,5-dinitrobenzamidine was synthesized in the same manner as in Reference Example 2. That is, the target compound in step (1) (34.4 g, 0.125 mol) was reacted with aminoacetaldehyde diethyl acetal (24 mL, 0.17 mol) in ethanol (130 mL) to give 46.8 g of a reddish brown solid containing the target compound.

(3) Ethyl 1-(2,2-diethoxyethyl)-2-(3,5-dinitrophenyl)pyrimidin-6(1H)-one-5-carboxylate was synthesized in the same manner as in Reference Example 2. That is, the target compound in step (2) (crude product obtained in the above reaction, 46.8 g) was reacted with diethyl ethoxymethylenemalonate (34 mL, 0.17 mol) in ethanol (65 mL) to give 37.3 g of the target compound as colorless crystals.

(4) 1-(2,2-Diethoxyethyl)-2-(3,5-dinitrophenyl)pyrimidin-6(1H)-one-5-carboxylic acid was synthesized in the same manner as in Reference Example 3. That is, the target compound in step (3) (36.7 g, 81.5 mmol) was reacted with lithium iodide (26.2 g, 0.196 mol) in pyridine (120 mL) to give 22.6 g (66%) of the target compound as brown crystals.

(5) [5-Benzyloxycarbonylamino-2-(3,5-dinitrophenyl)-6-oxo-1,6-dihydro-1-pyrimidinyl]acetaldehyde diethyl acetal was synthesized in the same manner as in Reference Example 2. That is, the target compound in step (4) (22.2 g, 52.6 mol) was reacted with diphenylphosphoryl azide (14.2 mL, 63.3 mmol) in the presence of triethylamine (14.5 mL, 0.104 mol) in 1,4-dioxane (200 mL), and then with benzyl alcohol (8.2 mL, 79 mmol) to give 5.38 g (17%) of a mixture of the target compound and benzyl alcohol as a brown oil.

(6) [5-Benzyloxycarbonylamino-2-(3,5-dinitrophenyl)-6-oxo-1,6-dihydro-1-pyrimidinyl]acetaldehyde was synthesized in the same manner as in Reference Example 2. That is, the target compound in step (5) (mixture with benzyl alcohol, 5.37 g, 8.86 mmol) was treated with 2N hydrochloric acid (80 mL) in THF (110 mL) to give 5.55 g of a black oil containing the target compound.

(7) [5-Benzyloxycarbonylamino-2-(3,5-dinitrophenyl)-6-oxo-1,6-dihydro-1-pyrimidinyl]acetic acid was synthesized in the same manner as in Reference Example 2. That is, the target compound in step (6) (crude product obtained in the above reaction, 5.55 g) was treated with sodium chlorite (85%, 6.88 g, 64.7 mmol) in the presence of 2-methyl-2-butene (9.4 mL, 89 mmol) and sodium dihydrogenphosphate dihydrate (9.68 g, 62.0 mmol) in a mixed solvent of 2-methyl-2-propanol (60 mL) and water (25 mL) to give 3.94 g of a mixture of the title compound and diethyl ether as a dark brown solid.

$^1$H-NMR (500 MHz, DMSO-$d_6$) δ 13.5 (brs, 1H), 9.17 (s, 1H), 8.95 (t, J=2.1 Hz, 1H), 8.74 (d, J=2.1 Hz, 2H), 8.55 (s, 1H), 7.45 (d, J=7.1 Hz, 2H), 7.40 (t, J=7.1 Hz, 2H), 7.34 (t, J=7.1 Hz, 1H), 5.21 (s, 2H), 4.59 (s, 2H); IR (KBr) 3320, 3070, 1715, 1660, 1505 cm$^{-1}$

REFERENCE EXAMPLE 17

Synthesis of [5-benzyloxycarbonylamino-6-oxo-2-(3-pyridyl)-1,6-dihydro-1-pyrimidinyl]acetic acid.

(1) To a mixture of chloroform (100 mL) and ethanol (200 mL) was added dropwise acetyl chloride (190 mL, 2.67 mol) under ice-cooling over 1 h. The resulting solution was stirred at oec for 30 min, whereafter a solution of 3-cyanopyridine (25.5 g, 245 mmol) in chloroform (300 mL) was added dropwise over 1.5 h. After stirring at room temperature for 17 h, precipitates were collected by filtration, washed with chloroform, and dried in vacuo to give 50.5 g (92%) of ethyl 3-pyridinecarboximidate dihydrochloride as colorless crystals.

(2) To a solution of the target compound in step (1) (50.0 g, 0.224 mol) in ethanol (200 mL) were added aminoacetaldehyde diethyl acetal (37 mL, 0.25 mol) and triethylamine (35 mL, 0.25 mol) under ice-cooling. The resulting mixture was stirred at room temperature for 5 h. Ethanol was evaporated under reduced pressure and the obtained concentrate was poured into 1N aqueous sodium hydroxide solution (600 mL) and then extracted with chloroform. The extract was dried over anhydrous magnesium sulfate. Evaporation of the solvent under reduced pressure gave 55.0 g of a yellow oil containing N-(2,2-diethoxyethyl)-3-pyridinecarboxamidine.

(3) Ethyl 1-(2,2-diethoxyethyl)-2-(3-pyridyl)pyrimidin-6(1H)-one-5-carboxylate was synthesized in the same manner as in Reference Example 2. That is, the target compound in step (2) (crude product obtained in the above reaction, 55.0 g) was reacted with diethyl ethoxymethylenemalonate (51 mL, 0.25 mol) in ethanol (100 mL) to give 53.0 g of the target compound as colorless crystals.

(4) 1-(2,2-Diethoxyethyl)-2-(3-pyridyl)pyrimidin-6(1H)-one-5-carboxylic acid was synthesized in the same manner as in Reference Example 3. That is, the target compound in step (3) (50.2 g, 139 mmol) was reacted with lithium iodide (43.1 g, 322 mmol) in pyridine (200 mL) to give 33.0 g (66%) of the target compound as a dark brown solid.

(5) [5-Benzyloxycarbonylamino-6-oxo-2-(3-pyridyl)-1,6-dihydro-1-pyrimidinyl]acetaldehyde diethyl acetal was synthesized in the same manner as in Reference Example 2. That is, the target compound in step (4) (32.5 g, 97.5 mmol) was reacted with diphenylphosphoryl azide (26 mL, 0.12 mol) in the presence of triethylamine (27 mL, 0.19 mol) in 1,4-dioxane (250 mL), and then with benzyl alcohol (15 mL, 0.14 mol) to give 30.8 g (72%) of the target compound as colorless crystals.

(6) [5-Benzyloxycarbonylamino-6-oxo-2-(3-pyridyl)-1,6-dihydro-1-pyrimidinyl]acetaldehyde was synthesized in the same manner as in Reference Example 2. That is, the target compound in step (5) (29.9 g, 68.2 mmol) was treated with 1N hydrochloric acid (180 mL) in THF (250 mL) to give 25.4 g of a brown solid containing the target compound.

(7) [5-Benzyloxycarbonylamino-6-oxo-2-(3-pyridyl)-1,6-dihydro-1-pyrimidinyl]acetic acid was synthesized in the same manner as in Reference Example 2. That is, the target compound in step (6) (crude product obtained in the above reaction, 25.4 g) was treated with sodium chlorite (85%, 53.0 g, 498 mmol) in the presence of 2-methyl-2-butene (72 mL, 0.68 mol) and sodium dihydrogenphosphate dihydrate (74.5 g, 478 mmol) in a mixed solvent of 2-methyl-2-propanol (430 mL) and water (180 mL) to give 17.4 g of the title compound as colorless crystals.

mp 189–190° C.; $^1$H-NMR (500 MHz, DMSO-$d_6$) δ 13.3 (brs, 1H), 9.06 (s, 1H), 8.74 (dd, J=4.9, 1.6 Hz, 1H), 8.70 (d, J=1.8 Hz, 1H), 8.50 (s, 1H), 7.94 (m, 1H), 7.56 (dd, J=7.9, 4.9 Hz, 1H), 7.45 (d, J=7.1 Hz, 2H), 7.40 (t, J=7.1 Hz, 2H), 7.34 (t, J=7.1 Hz, 1H), 5.20 (s, 2H), 4.57 (s, 2H); IR (KBr) 3380, 1720, 1660, 1600, 1510 cm$^{-1}$

REFERENCE EXAMPLE 18

Synthesis of [5-benzyloxycarbonylamino-6-oxo-2-(4-pyridyl)-1,6-dihydro-1-pyrimidinyl]acetic acid.

(1) To a solution of 4-cyanopyridine (23.9 g, 0.230 mol) in methanol (200 mL) was added a solution (5.0 M, 5.0 mL, 25 mmol) of sodium methoxide in methanol. The resulting mixture was stirred at room temperature for 7 h. Acetic acid (1.5 mL, 26 mmol) was added to stop the reaction. Then, aminoacetaldehyde diethyl acetal (38 mL, 0.26 mol) was added under ice-cooling, and the resulting mixture was stirred at room temperature for 14 h. Methanol was evaporated under reduced pressure, and the concentrate obtained was poured into 0.5N sodium hydroxide (500 mL) and then extracted with chloroform. The extract was dried over anhydrous magnesium sulfate. Evaporation of the solvent under reduced pressure gave 80.6 g of a colorless solid containing N-(2,2-diethoxyethyl)-4-pyridinecarboxamidine.

(2) Ethyl 1-(2,2-diethoxyethyl)-2-(4-pyridyl)-pyrimidin-6(1H)-one-5-carboxylate was synthesized in the same manner as in Reference Example 2. That is, the target compound in step (1) (crude product obtained in the above reaction, 80.6 g) was reacted with diethyl ethoxymethylenemalonate (52 mL, 0.26 mol) in ethanol (100 mL) to give 54.9 g of the target compound as colorless crystals.

(3) 1-(2,2-Diethoxyethyl)-2-(4-pyridyl)-pyrimidin-6(1H)-one-5-carboxylic acid was synthesized in the same manner as in Reference Example 3. That is, the target compound in step (2) (56.7 g, 179 mmol) was reacted with lithium iodide (57.5 g, 430 mmol) in pyridine (220 mL) to give 32.1 g (54%) of the target compound as pale-reddish brown crystals.

(4) [5-Benzyloxycarbonylamino-6-oxo-2-(4-pyridyl)-1,6-dihydro-1-pyrimidinyl]acetaldehyde diethyl acetal was synthesized in the same manner as in Reference Example 2. That is, the target compound in step (3) (30.8 g, 92.4 mmol) was reacted with diphenylphosphoryl azide (24 mL, 0.11 mol) in the presence of triethylamine (26 mL, 0.19 mol) in 1,4-dioxane (230 mL), and then with benzyl alcohol (14 mL, 0.14 mol) to give 28.4 g (70%) of the target compound as colorless crystals.

(5) [5-Benzyloxycarbonylamino-6-oxo-2-(4-pyridyl)-1,6-dihydro-1-pyrimidinyl]acetaldehyde was synthesized in the same manner as in Reference Example 2. That is, the target compound in step (4) (27.7 g, 63.2 mmol) was treated with 1N hydrochloric acid (180 mL) in THF (250 mL) to give 24.7 g of a colorless solid containing the target compound.

(6) [5-Benzyloxycarbonylamino-6-oxo-2-(4-pyridyl)-1,6-dihydro-1-pyrimidinyl]acetic acid was synthesized in the same manner as in Reference Example 2. That is, the target compound in step (5) (crude product obtained in the above reaction, 24.7 g) was treated with sodium chlorite (85%, 49.1 g, 461 mmol) in the presence of 2-methyl-2-butene (67 mL, 0.63 mol) and sodium dihydrogenphosphate dihydrate (69.0 g, 442 mmol) in a mixed solvent of 2-methyl-2-propanol (400 mL) and water (170 mL) to give 21.7 g of the title compound as yellow crystals.

mp 216–219° C.; $^1$H-NMR (500 MHz, DMSO-$d_6$) δ 13.3 (brs, 1H), 9.09 (s, 1H), 8.76 (d, J=6.0 Hz, 2H), 8.50 (s, 1H), 7.51 (d, J=6.0 Hz, 2H), 7.45 (d, J=7.1 Hz, 2H), 7.40 (t, J=7.1 Hz, 2H), 7.34 (t, J=7.1 Hz, 1H), 5.20 (s, 2H), 4.55 (s, 2H); IR (KBr) 3370, 3260, 1725, 1665, 1595, 1525 cm$^{-1}$ REFERENCE EXAMPLE 19
Synthesis of [5-benzyloxycarbonylamino-6-oxo-2-(2-thienyl)-1,6-dihydro-1-pyrimidinyl]acetic acid.

(1) Ethyl 2-thiophenecarboximidate hydrochloride was synthesized in the same manner as in Reference Example 2. That is, 2-thiophenecarbonitrile (25.2 g, 0.231 mol) was treated with hydrogen chloride in ethanol (250 mL) to give 16.3 g (37%) of the target compound as colorless crystals.

(2) N-(2,2-Diethoxyethyl)-2-thiophenecarboxamidine was synthesized in the same manner as in Reference Example 2. That is, the target compound in step (1) (16.1 g, 84.0 mmol) was reacted with aminoacetaldehyde diethyl acetal (13.5 mL, 92.8 mmol) in ethanol (65 mL) to give 30.4 g of a colorless, transparent oil containing the target compound.

(3) Ethyl 1-(2,2-diethoxyethyl)-2-(2-thienyl)pyrimidin-6 (1H)-one-5-carboxylate was synthesized in the same manner as in Reference Example 2. That is, the target compound in step (2) (crude product obtained in the above reaction, 30.4 g) was reacted with diethyl ethoxymethylenemalonate (19 mL, 94 mmol) in ethanol (40 mL) to give 18.1 g of the target compound as a pale-yellow solid.

(4) 1-(2,2-Diethoxyethyl)-2-(2-thienyl)pyrimidin-6(1H)-one-5-carboxylic acid was synthesized in the same manner as in Reference Example 3. That is, the target compound in step (3) (17.7 g, 48.3 mmol) was treated with lithium iodide (15.5 g, 116 mmol) in pyridine (65 mL) to give 12.2 g (75%) of the target compound as pale-brown crystals.

(5) [5-Benzyloxycarbonylamino-6-oxo-2-(2-thienyl)-1,6-dihydro-1-pyrimidinyl]acetaldehyde diethyl acetal was synthesized in the same manner as in Reference Example 2. That is, the target compound in step (4) (11.7 g, 34.6 mmol) was reacted with diphenylphosphoryl azide (8.5 mL, 38 mmol) in the presence of triethylamine (9.5 mL, 68 mmol) in 1,4-dioxane (100 mL), and then with benzyl alcohol (4.5 mL, 43 mmol) to give 13.9 g (83%) of a mixture of the target compound and benzyl alcohol as a pale-yellow oil.

(6) [5-Benzyloxycarbonylamino-6-oxo-2-(2-thienyl)-1,6-dihydro-1-pyrimidinyl]acetaldehyde was synthesized in the same manner as in Reference Example 2. That is, the target compound in step (5) (mixture with benzyl alcohol, 13.7 g, 28.3 mmol) was treated with 1N hydrochloric acid (75 mL) in THF (100 mL) to give 11.8 g of a pale-yellow oil containing the target compound.

(7) [5-Benzyloxycarbonylamino-6-oxo-2-(2-thienyl)-1,6-dihydro-1-pyrimidinyl]acetic acid was synthesized in the same manner as in Reference Example 2. That is, the target compound in step (6) (crude product obtained in the above reaction, 11.8 g) was treated with sodium chlorite (80%, 22.4 g, 198 mmol) in the presence of 2-methyl-2-butene (30 mL, 0.28 mol) and sodium dihydrogenphosphate dihydrate (32.2 g, 206 mmol) in a mixed solvent of 2-methyl-2-propanol (175 mL) and water (75 mL) to give 10.4 g of the title compound as pale-yellow crystals.

mp 151–152° C.; $^1$H-NMR (500 MHz, DMSO-$d_6$) δ 13.44 (brs, 1H), 9.00 (s, 1H), 8.44 (s, 1H), 7.85 (dd, J=5.1, 1.0 Hz, 1H), 7.45–7.41 (m, 3H), 7.39 (t, J=7.1 Hz, 2H), 7.34 (t, J=7.1 Hz, 1H), 7.20 (dd, J=5.1, 3.8 Hz, 1H), 5.19 (S, 2H), 4.86 (s, 2H); IR (KBr) 3600–2200, 1730, 1650, 1600, 1530, 1500 cm$^{-1}$ EXAMPLE 1
Synthesis of 2-(5-benzyloxycarbonylamino-6-oxo-2-phenyl-1,6-dihydro-1-pyrimidyl)-N-(1-benzyl-3,3,3-trifluoro-2-oxopropyl)acetamide.

(1) To a solution of (5-benzyloxycarbonylamino-6-oxo-2-phenyl-1,6-dihydro-1-pyrimidinyl)acetic acid (title compound in Reference Example 2, 8.57 g, 22.6 mmol) and 3-amino-1,1,1-trifluoro-4-phenyl-2-butanol (title compound in Reference Example 1, 5.91 g, 27.2 mmol) in DMF (75 mL) were added WSCI hydrochloride (5.20 g, 27.2 mmol) and HOBT (6.10 g, 45.1 mmol). The resulting mixture was stirred at room temperature for 16 h, poured into 0.5N hydrochloric acid (500 mL), and then extracted with ethyl acetate. The extract was washed with saturated aqueous sodium hydrogencarbonate solution and saturated brine, and dried over anhydrous magnesium sulfate. The residue obtained by concentration of the extract was separated and purified by silica gel column chromatography (chloroform-ethyl acetate, 83:17) to give 11.4 g (87%) of 2-(5-benzyloxycarbonylamino-6-oxo-2-phenyl-1,6-dihydro-1-pyrimidyl)-N-(1-benzyl-3,3,3-trifluoro-2-hydroxypropyl)-acetamide as colorless crystals.

mp 198–202° C.; $^1$H-NMR (500 MHz, DMSO-$d_6$) δ 8.85 (s, 1H), 8.43 (s, 1H), 8.32 (d, J=8.9 Hz, 1H), 7.08–7.54 (m, 15H), 6.70 (d, J=7.1 Hz, 2H), 5.19 (s, 2H), 4.41 (d, J=16.3 Hz, 1H), 4.25 (d, J=16.3 Hz, 1H), 4.07 (m, 1H), 3.90(m, 1H), 2.92 (dd, J=14.1, 2.6 Hz, 1H), 2.75 (dd, J=14.1, 10.4 Hz, 1H); IR (KBr) 3430, 3370, 3260, 3080, 1705, 1660, 1600, 1520 cm$^{-1}$ (2) To a solution of the hydroxy compound obtained above (2.00 g, 3.44 mmol) in dimethylsulfoxide (DMSO) (15 mL) and toluene (15 mL) were added WSCI hydrochloride (6.60 g, 34.4 mmol) and dichloroacetic acid (1.1 mL, 13 mmol). The resulting mixture was stirred at room temperature for 2.5 h, poured into 1N hydrochloric acid (150 mL), and then extracted with ethyl acetate. The extract was washed with saturated aqueous sodium hydrogencarbonate solution and saturated brine, and dried over anhydrous magnesium sulfate. The residue obtained by concentration of the extract was separated and purified by silica gel column chromatography (chloroform-ethyl acetate, 83:17) to give 1.29 g (65%) of the title compound as colorless crystals. Recrystallization thereof from chloroform-hexane (1:1) afforded 858 mg of colorless crystals.

mp 186–188° C.; $^1$H-NMR (500 MHz, DMSO-d$_6$+D$_2$O) δ 8.40 (s, 1H), 7.50 (t, J=7.3 Hz, 1H), 7.44 (d, J=7.1 Hz, 2H), 7.30–7.42 (m, 7 H), 7.10–7.22 (m, 5H), 5.18 (s, 2H), 4.21–4.43 (m, 3H), 3.12 (dd, J=14.1, 2.1 Hz, 1H), 2.60 (dd, J=14.1, 11.4 Hz, 1H); IR (KBr) 3280, 1725, 1650, 1600, 1515 cm$^{-1}$ MS (CI, positive) m/z 579 (MR$^+$)

EXAMPLE 2

Synthesis of 2-(5-amino-6-oxo-2-phenyl-1,6-dihydro-1-pyrimidyl)-N-(1-benzyl-3,3,3-trifluoro-2-oxopropyl) acetamide.

To a mixed solution of the title compound in Example 1 (734 mg, 1.27 mmol) in ethanol (20 mL) and THF (20 mL) was added 1N hydrochloric acid (0.2 mL), and 10% palladium carbon (270 mg) was added under a nitrogen atmosphere. The resulting mixture was stirred at room temperature for 6 h under a hydrogen atmosphere. Palladium carbon was removed by filtration and washed with ethanol. The filtrate was concentrated, and the residue obtained was separated and purified by silica gel column chromatography (chloroform-methanol, 91:9) to give 466 mg (83%) of the title compound as pale-yellow crystals. Recrystallization thereof from chloroform-hexane (3:1) afforded 343 mg of colorless crystals.

mp 208–211° C.; $^1$H-NMR (500 MHz, DMSO-d$_6$+D$_2$O) δ 7.45 (t, J=7.3 Hz, 1H), 7.09–7.35 (m, 10H), 4.18–4.36 (m, 3H), 3.12 (dd, J=14.1, 2.2 Hz, 1H), 2.61 (dd, J=14.1, 11.5 Hz, 1H); IR (KBr) 3420, 3260, 3050, 1645, 1610, 1540, 1515 cm$^{-1}$ MS (CI, positive) m/z 445 (MH$^+$)

EXAMPLE 3

Synthesis of 2-[5-benzyloxycarbonylamino-2-(4-fluorophenyl)-6-oxo-1,6-dihydro-1-pyrimidyl]-N-(1-benzyl-3,3,3-trifluoro-2-oxopropyl)acetamide.

(1) 2-[5-Benzyloxycarbonylamino-2-(4-fluorophenyl)-6-oxo-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-2-(4-fluorophenyl)-6-oxo-1,6-dihydro-1-pyrimidinyl]acetic acid (title compound in Reference Example 3, mixture with benzyl alcohol, 1.90 g, 4.48 mmol) was treated with 3-amino-1,1,1-trifluoro-4-phenyl-2-butanol (title compound in Reference Example 1, 1.00 g, 4.56 mmol), WSCI hydrochloride (1.03 g, 5.37 mmol) and HOBT (1.21 g, 8.95 mmol) in DMF (15 mL) to give 2.49 g (93%) of the target compound as colorless crystals.

mp 242–245° C.; $^1$H-NMR (500 MHz, DMSO-$_6$+D$_2$O) δ 8.86 (s, 1H), 8.41 (s, 1H), 8.33 (d, J=8.6 Hz, 1H), 7.42–7.46 (m, 4H), 7.39 (t, J=7.6 Hz, 2H), 7.34 (t, J=7.2Hz, 1H), 7.16–7.24 (m, 5H), 7.10 (d, J=8.0 Hz, 2H), 6.71 (d, J=6.7 Hz, 1H), 5.18 (s, 2H), 4.43 (d, J=16.6 Hz, 1H), 4.22 (d, J=16.6 Hz, 1H), 4.07 (m, 1H), 3.90 (m, 1H), 2.92 (dd, J=14.2, 2.8 Hz, 1H), 2.72 (dd, J=14.2, 10.4 Hz, 1H); IR (KBr) 3410, 3250, 1705, 1660, 1600, 1525 cm$^{-1}$ (2) The hydroxy compound obtained above (2.08 g, 3.48 mmol) was treated with WSCI hydrochloride (6.67 g, 34.8 mmol) and dichloroacetic acid (1.1 mL, 13 mmol) in a mixed solution of DMSO (15 mL) and toluene (15 mL) to give 1.26 g (61%) of the title compound as colorless crystals.

mp 103–107° C.; $^1$H-NMR (500 MHz, DMSO-d$_6$+D$_2$O) δ 8.39 (s, 1H), 7.32–7.46 (m, 7H), 7.08–7.21 (m, 7H), 5.18 (s, 2H), 4.20–4.45 (m, 3H), 3.11 (dd, J=14.1, 2.2 Hz, 1H), 2.59 (dd, J=14.1, 11.5 Hz, 1H); IR (KBr) 3370, 1730, 1640, 1600, 1520 cm$^{-1}$ MS (CI, positive) m/z 597 (MH$^+$)

EXAMPLE 4

Synthesis of 2-[5-amino-2-(4-fluorophenyl)-6-oxo-1,6-dihydro-1-pyrimidyl]-N-(1-benzyl-3,3,3-trifluoro-2-oxopropyl)acetamide.

The title compound was synthesized in the same manner as in Example 2. That is, the title compound in Example 3 (705 mg, 1.18 mmol) was reacted under a hydrogen atmosphere in the presence of 10% palladium carbon in a mixed solvent of ethanol (20 mL), THF (20 mL) and 1N hydrochloric acid (0.2 mL) to give 217 mg (40%) of the title compound as pale-yellow crystals.

mp 133–135° C.; $^1$H-NMR (500 MHz, DMSO-d$^6$+D$_2$O) δ 7.30 (dd, J=8.7, 5.5 Hz, 2H), 7.28 (s, 1H), 7.13–7.22 (m, 5H), 7.09 (t, J=8.8 Hz, 2H), 4.35 (d, J=16.4 Hz, 1H), 4.20–4.28 (m, 2H), 3.11 (dd, J=14.1, 2.4 Hz, 1H), 2.60 (dd, J=14.1, 11.5 Hz, 1H); IR (KBr) 3420, 3270, 1645, 1615, 1545, 1500 cm$^{-1}$ MS (CI, positive) m/z 463 (MH$^+$)

EXAMPLE 5

Synthesis of 2-[5-benzyloxycarbonylamino-6-oxo-2-(p-tolyl)-1,6-dihydro-1-pyrimidyl]-N-(1-benzyl-3,3,3-trifluoro-2-oxopropyl)-acetamide.

(1) 2-[5-Benzyloxycarbonylamino-6-oxo-2-(p-tolyl)-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-6-oxo-2-(p-tolyl)-1,6-dihydro-1-pyrimidinyl]acetic acid (title compound in Reference Example 4, 3.00 g, 7.63 mmol) was treated with 3-amino-1,1,1-trifluoro-4-phenyl-2-butanol (title compound in Reference Example 1, 1.76 g, 8.03 mmol), WSCI hydrochloride (1.76 g, 9.18 mmol) and HOBT (2.06 g, 15.2 mmol) in DMF (25 mL) to give 4.23 g (93%) of the target compound as colorless crystals.

mp 232–234° C.; $^1$H-NMR (500 MHz, DMSO-d$_6$) δ 8.82 (s, 1H), 8.41 (s, 1H), 8.33 (d, J=8.6 Hz, 1H), 7.44 (d, J=7.2 Hz, 2H), 7.39 (t, J=7.2 Hz, 2H), 7.33 (t, J=7.2 Hz, 1H), 7.26 (d, J=8.1 Hz, 2H), 7.17–7.24 (m, 5H), 7.11 (dd, J=7.7, 2.2 Hz, 2H), 6.71 (d, J=6.8 Hz, 1H), 5.18 (s, 2H), 4.43 (d, J=16.4 Hz, 1H), 4.23 (d, J=16.4 Hz, 1H), 4.09 (m, 1H), 3.91 (m, 1H), 2.93 (dd, J=14.2, 2.8 Hz, 1H), 2.75 (dd, J=14.2, 10.4 Hz, 1H), 2.37 (s, 3H); IR (KBr) 3370, 3260, 1705, 1660, 1600, 1525, 1500 cm$^{-1}$ (2) The hydroxy compound obtained above (3.00 g, 5.05 mmol) was treated with WSCI hydrochloride (9.67 g, 50.4 mmol) and dichloroacetic acid (1.6 mL, 19 mmol) in a mixed solution of DMSO (25 mL) and toluene (25 mL) to give 2.34 g (78%) of the title compound as colorless crystals.

mp 173–175° C.; $^1$H-NMR (500 MHz, DMSO-d$_6$+D$_2$O) δ 8.38 (s, 1H), 7.44 (d, J=7.1 Hz, 2H), 7.40 (t, J=7.1 Hz, 2H), 7.34 (t, J=7.1 Hz, 1H), 7.13–7.22 (m, 9H), 5.18 (s, 2H), 4.40 (d, J=16.4 Hz, 1H), 4.22–4.33 (m, 2H), 3.13 (dd, J=14.2, 2.2 Hz, 1H), 2.60 (dd, J=14.2, 11.4 Hz, 1H), 2.38 (s, 3H); IR (KBr) 3300, 1725, 1655, 1605, 1520, 1500 cm$^{-1}$ MS (CI, positive) m/z 593 (MH$^+$)

EXAMPLE 6

Synthesis of 2-[5-amino-6-oxo-2-(p-tolyl)-1,6-dihydro-1-pyrimidyl]-N-(1-benzyl-3,3,3-trifluoro-2-oxopropyl) acetamide.

To a mixed solution of the title compound in Example 5 (500 mg, 0.844 mmol) in methanol (20 mL) and formic acid (1.0 mL) was added 10% palladium carbon (199 mg) under a nitrogen atmosphere. The resulting mixture was stirred at room temperature for 14 h. Palladium carbon was removed by filtration and washed with ethanol. The filtrate was concentrated, added to saturated aqueous sodium hydrogencarbonate solution (50 mL), and then extracted with ethyl acetate. The extract was washed with saturated brine and the solvent was evaporated under reduced pressure. The residue obtained was separated and purified by silica gel column chromatography (chloroform-methanol, 95:5) to give 235 mg (61%) of the title compound as colorless crystals. Recrystallization thereof from chloroform afforded 152 mg of colorless crystals.

mp 200–203° C.; $^1$H-NMR (500 MHz, DMSO-d$_6$+D$_2$O) δ 7.31 (s, 1H), 7.09–7.22 (m, 9H), 4.36 (d, J=16.3 Hz, 1H), 4.20–4.28 (m, 2H), 3.13 (dd, J=14.2, 2.4 Hz, 1H), 2.62 (dd, J=14.2, 11.4 Hz, 1H), 2.36 (s, 3H); IR (KBr) 3410, 3290, 1640, 1620, 1550 cm$^{-1}$ MS (CI, positive) m/z 459 (MH$^+$)

EXAMPLE 7

Synthesis of 2-[5-benzyloxycarbonylamino-6-oxo-2-(m-tolyl)-1,6-dihydro-1-pyrimidyl]-N-(1-benzyl-3,3,3-trifluoro-2-oxopropyl)-acetamide.

(1) 2-[5-Benzyloxycarbonylamino-6-oxo-2-(m-tolyl)-1,6-dihydro-1-pyrimidyl]-N-(1-benzyl-3,3,3-trifluoro-2-hydroxypropyl)acetamide was synthesized in the same manner as in Example 1. That is, 2-[5-benzyloxycarbonylamino-6-oxo-2-(m-tolyl)-1,6-dihydro-1-pyrimidinyl]acetic acid (title compound in Reference Example 5, 3.00 g, 7.63 mmol) was treated with 3-amino-1,1,1-trifluoro-2-phenyl-2-butanol (title compound in Reference Example 1, 1.76 g, 8.03 mmol), WSCI hydrochloride (1.76 g, 9.18 mmol) and HOBT (2.06 g, 15.2 mmol) in DMF (25 mL) to give 4.54 g (100%) of the target compound as colorless crystals.

mp 235–237° C.; $^1$H-NMR (500 MHz, DMSO-d$_6$) δ 8.84 (s, 1H), 8.42 (s, 1H), 8.37 (d, J=8.5 Hz, 1H), 7.44 (d, J=7.2 Hz, 2H), 7.39 (t, J=7.2 Hz, 2H), 7.32–7.36 (m, 2H), 7.24–7.28 (m, 2H), 7.14–7.23 (m, 4H), 7.11 (d, J=6.4 Hz, 2H), 6.74 (s, 1H), 5.19 (s, 2H), 4.40 (d, J=16.4 Hz, 1H), 4.30 (d, J=16.4 Hz, 1H), 4.04 (m, 1H), 3.90 (m, 1H), 2.91 (dd, J=14.2, 2.9 Hz, 1H), 2.77 (dd, J=14.2, 10.1 Hz, 1H), 2.30 (s, 3H); IR (KBr) 3450, 3360, 3280, 3090, 2950, 1705, 1660, 1600, 1555, 1520 cm$^{-1}$ (2) The hydroxy compound obtained above (3.00 g, 5.05 mmol) was treated with WSCI hydrochloride (9.67 g, 50.4 mmol) and dichloroacetic acid (1.6 mL, 19 mmol) in a mixed solution of DMSO (25 mL) and toluene (25 mL) to give 2.24 g (75%) of the title compound as colorless crystals.

mp 128–132° C.; $^1$H-NMR (500 MHz, DMSO-d$_6$+D$_2$O) δ 8.39 (s, 1H), 7.44 (d, J=7.1 Hz, 2H), 7.40 (t, J=7.1 Hz, 2H), 7.31–7.37 (m, 2 H), 7.23 (t, J=7.6 Hz, 1H), 7.13–7.21 (m, 6H), 7.08 (d, J=7.6 Hz, 2H), 5.19 (s, 2H), 4.40 (d, J=16.2 Hz, 1H), 4.33 (d, J=16.2 Hz, 1H), 4.20 (dd, J=11.2, 2.2 Hz, 1H), 3.11 (dd, J=14.2, 2.2 Hz, 1H), 2.60 (dd, J=14.2, 11.2 Hz, 1H), 2.30 (s, 3H); IR (KBr) 3300, 2960, 1690, 1660, 1615, 1515 cm$^{-1}$ MS (CI, positive) m/z 593 (MH$^+$)

EXAMPLE 8

Synthesis of 2-[5-amino-6-oxo-2-(m-tolyl)-1,6-dihydro-1-pyrimidyl]-N-(1-benzyl-3,3,3-trifluoro-2-oxopropyl) acetamide.

The title compound was synthesized in the same manner as in Example 2. That is, the title compound in Example 7 (1.28 g, 2.16 mmol) was reacted under a hydrogen atmosphere in the presence of 10% palladium carbon (460 mg) in a mixed solution of ethanol (20 mL), THF (20 mL) and 1N hydrochloric acid (0.4 mL) to give 330 mg (33%) of the title compound as pale-yellow crystals.

mp 177–181° C.; $^1$H-NMR (500 MHz, DMSO-d$_6$+D$_2$O) δ 7.34 (s, 1H), 7.30 (d, J=7.7 Hz, 1H), 7.22 (t, J=7.7 Hz, 1H), 7.10–7.21 (m, 6H), 7.02 (d, J=7.7 Hz, 1H), 4.39 (d, J=16.2 Hz, 1H), 4.31 (d, J=16.2 Hz, 1H), 4.21 ((dd, J=11.3, 2.3 Hz, 1H), 3.12 (dd, J=14.1, 2.3 Hz, 1H), 2.61 (dd, J=14.1, 11.3 Hz, 1H), 2.29 (s, 3H); IR (KBr) 3410, 3360, 1650, 1615, 1540, 1520 cm$^{-1}$ MS (CI, positive) m/z 459 (MH$^+$)

EXAMPLE 9

Synthesis of 2-[5-benzyloxycarbonylamino-2-(4-fluorophenyl)-6-oxo-1,6-dihydro-1-pyrimidinyl]-N-[1(S)-benzyl-3,3-difluoro-2-oxo-3-[N-(benzyl)carbamoyl]propyl] acetamide.

(1) 2-[5-Benzyloxycarbonylamino-2-(4-fluorophenyl)-6-oxo-1,6-dihydro-1-pyrimidinyl]-N-[1(S)-benzyl-3,3-difluoro-2(R)-hydroxy-3-[N-(benzyl)caramoyl]propyl] acetamide was synthesized in the same manner as in Example 1. That is, 2-[5-benzyloxycarbonylamino-2-(4-fluorophenyl)-6-oxo-1,6-dihydro-1-pyrimidinyl]acetic acid (title compound in Reference Example 3, mixture with benzyl alcohol, 380 mg, 0.897 mmol) was treated with N-[4(S)-amino-2,2-difluoro-3(R)-hydroxy-5-phenylpentanoyl]benzylamine (title compound in Reference Example 6: 300 mg, 0.897 mmol), HOBT (242 mg, 1.79 mmol) and WSCI hydrochloride (206 mg, 1.08 mmol) in dichloromethane (30 mL) to give 590 mg (92%) of the target compound as colorless crystals.

mp 223–224° C.; $^1$H-NMR (200 MHz, DMSO-d$_6$) δ 9.01 (m, 1H), 8.83 (s, 1H), 8.44 (s, 1H), 8.17 (d, J=8.9 Hz, 1H), 7.55–7.17 (m, 19H), 6.40 (d, J=7.1 Hz, 1H), 5.18 (s, 2H), 4.50–3.80 (m, 6H), 2.82–2.49 (m, 2H); IR (KBr) 3400, 3280, 1720, 1650, 1605, 1525, 1500 cm$^{-1}$ (2) The hydroxy compound obtained above (390 mg, 0.550 mmol) was treated with WSCI hydrochloride (1.09 g, 5.69 mmol) and dichloroacetic acid (0.176 mL, 2.13 mmol) in a mixed solution of DMSO (3 mL) and toluene (3 mL) to give 262 mg (67%) of the title compound as a colorless solid.

mp 185–186° C.; $^1$H-NMR (200 MHz, DMSO-d$_6$+D$_2$O) δ 8.43 (s, 1H), 7.47–7.12 (m, 19 H), 5.18 (s, 2H), 4.52–4.24 (m, 6H), 3.14 (dd, J=14.3, 3.9 Hz, 1H), 2.59 (dd, J=14.3, 9.7 Hz, 1H); IR (KBr) 3370, 1730, 1640, 1600, 1520 cm$^{-1}$ MS (CI, positive) m/z 712 (MH$^+$)

EXAMPLE 10

Synthesis of 2-[5-amino-2-(4-fluorophenyl)-6-oxo-1,6-dihydro-1-pyrimidinyl]-N-[1(S)-benzyl-3,3-difluoro-2-oxo-3-[N-(benzyl)-carbamoyl]propyl]acetamide.

To a mixed solution of the title compound in Example 9 (150 mg, 0.210 mmol) in THF (5 ml) and methanol (3 ml)

was added 10% palladium carbon (60 mg) and formic acid (0.3 mL) under a nitrogen atmosphere. The resulting mixture was stirred for 48 h. The catalyst was removed by filtration and washed with THF. The residue obtained by concentration of the filtrate was separated and purified by silica gel column chromatography (chloroform-methanol, 90:10), and further by preparative TLC (chloroform-methanol, 90:10) to give 20.0 mg (16%) of the title compound as a pale-yellow solid.

mp 90–91° C.; $^1$H-NMR (200 MHz, CDCl$_3$) δ 7.47 (s, 1H), 7.38–6.96 (m, 14H), 5.24 (m, 1H), 4.57–4.22 (m, 4H), 3.50–3.23 (m, 1H), 3.00–2.77 (m, 1H), 1.59 (brs, 2H); IR (KBr) 3300, 3050, 2920, 1750, 1650, 1605, 1540, 1510 cm$^{-1}$ MS (CI, positive) m/z 578 (MH$^+$)

EXAMPLE 11

Synthesis of 2-(3-benzyloxycarbonylamino-5-benzyl-2-oxo-1,2-dihydro-1-pyridyl)-N-(1-benzyl-3,3,3-trifluoro-2-oxopropyl)acetamide.

(1) 2-(3-Benzyloxycarbonylamino-5-benzyl-2-oxo-1,2-dihydro-1-pyridyl)-N-(1-benzyl-3,3,3-trifluoro-2-hydroxypropyl)acetamide was synthesized in the same manner as in Example 1. That is, 2-(3-benzyloxycarbonylamino-5-benzyl-2-oxo-1,2-dihydro-1-pyridyl)acetic acid (title compound in Reference Example 7, 380 mg, 0.968 mmol) was treated with 3-amino-1,1,1-trifluoro-4-phenyl-2-butanol (title compound in Reference Example 1, 249 mg, 1.14 mmol), WSCI hydrochloride (277 mg, 1.45 mmol) and HOBT (158 mg, 1.17 mmol) in DMF (10 mL) to give 428 mg (74%) of the target compound as a slightly yellow solid.

$^1$H-NMR (200 MHz, DMSO-d$_6$) δ 8.38 (d, J=8.5 Hz, 1H), 8.29 (s, 1H), 7.68 (d, J=2.1 Hz, 1H), 7.45–7.08 (m, 15H), 7.00 (d, J=2.0 Hz, 1H), 6.70 (d, J=4.8 Hz, 1H), 5.12 (s, 2H), 4.56, 4.39 (AB-q, J=15.7 Hz, 2H), 4.11 (m, 1H), 3.98 (m, 1H), 3.66 (s, 2H), 2.97 (m, 1H), 2.76 (dd, J=14. 0, 10.3 Hz, 1H); IR (KBr) 3300, 1720, 1650, 1590, 1510 cm$^{-1}$ (2) The hydroxy compound obtained above (407 mg, 0.686 mmol) was treated with WSCI hydrochloride (1.31 g, 6.83 mmol) and dichloroacetic acid (0.23 mL, 2.8 mmol) in a mixed solution of DMSO (5.2 mL) and toluene (10 mL) to give 118 mg (29%) of the title compound as a colorless solid.

mp 127–130° C.; $^1$H-NMR (500 MHz, DMSO-d$_6$+D$_2$O) δ 7.65 (d, J=2.0 Hz, IH), 7.41–7.08 (m, 15H), 6.75 (d, J=2.1 Hz, 1H), 5.12 (s, 2H), 4.59, 4.38 (AB-q, J=15.7 Hz, 2H), 4.26 (m, 1H), 3.63 (s, 2H), 3.11 (dd, J=13.8, 2.5 Hz, 1H), 2.65 (dd, J=13.7, 11.5 Hz, 1H); IR (KBr) 3300, 1720, 1655, 1595, 1510 cm$^{-1}$ MS (CI, positive) m/z 592 (MH$^+$)

EXAMPLE 12

Synthesis of 2-(3-amino-5-benzyl-2-oxo-1,2-dihydro-1-pyridyl)-N-(1-benzyl-3,3,3-trifluoro-2-oxopropyl) acetamide.

The title compound was synthesized in the same manner as in Example 2. That is, the title compound in Example 11 (78.6 mg, 0.133 mmol) was reacted under a hydrogen atmosphere in the presence of 10% palladium carbon (22.9 mg) in a mixed solution of 1,4-dioxane (2 mL) and 1N hydrochloric acid (0.4 mL) to give 39.0 mg (64%) of the title compound as a pale-yellow solid.

mp 77–81° C.; $^1$H-NMR (500 MHz, DMSO-d$_6$+D$_2$O) δ 7.35–7.07 (m, 12H), 4.52, 4.27 (AB-q, J=15.4 Hz, 2H), 4.31–4.21 (m, 1H), 3.50 (s, 2H), 3.11 (dd, J=13.8, 2.5 Hz, 1H), 2.64 (dd, J=13.8, 11.6 Hz, 1H); IR (KBr) 3250, 1650, 1580, 1530 cm$^{-1}$ MS (CI, positive) m/z 458 (MH$^+$)

EXAMPLE 13

Synthesis of 2-(3-benzyloxycarbonylamino-2-oxo-6-phenyl-1,2-dihydro-1-pyridyl)-N-(1-benzyl-3,3,3-trifluoro-2-oxopropyl)acetamide.

(1) To a suspension of 3-benzyloxycarbonylamino-6-phenylpyrid-2-one (title compound in Reference Example 9, 3.20 g, 10.0 mmol) in DMF (90 mL) was added sodium hydride (60% in oil, 462 mg, 11.6 mmol). The resulting mixture was stirred at room temperature for 20 min. N-[1-Benzyl-2-(tert-butyldimethylsilyl)oxy-3,3,3-trifluoropropyl]-2-iodoacetamide (title compound in Reference Example 8, 5.77 g, 11.5 mmol) was added, and the mixture was stirred at room temperature for 13 h. 2N Hydrochloric acid (100 mL) was added and the resulting mixture was poured into 2N hydrochloric acid (200 mL), and then extracted with ethyl acetate. The extract was washed with water and saturated brine, dried over anhydrous magnesium sulfate, and concentrated under reduced pressure. The residue was separated and purified by silica gel column chromatography (dichloromethane-ethyl acetate, 99:1) to give 2.49 g (36%) of 2-(3-benzyloxycarbonylamino- 2-oxo-6-phenyl-1,2-dihydro-1-pyridyl)-N-[1-benzyl-2-(tert-butyldimethylsilyl)oxy-3,3,3-trifluoropropyl]acetamide as a colorless amorphous.

$^1$H-NMR (500 MHz, DMSO-d$_6$) δ 8.42 (s, 1H), 8.18 (d, J=7.4 Hz, 1H), 7.88 (d, J=7.6 Hz, 1H), 7.43–7.48 (m, 3H), 7.32–7.41 (m, 5H), 7.30 (d, J=7.1 Hz, 2H), 7.25 (t, J=6.8 Hz, 2H), 7.21 (t, J=6.8 Hz, 1H), 7.13 (d, J=6.8 Hz, 2H), 6.18 (d, J=7.6 Hz, 1H), 5.19 (s, 2H), 4.38 (d, J=16.3 Hz, 1H), 4.32 (d, J=16.3 Hz, 1H), 4.22 (m, 1H), 4.08 (m, 1H), 2.92 (dd, J=14.9, 2.4 Hz, 1H), 2.70 (dd, J=14.9, 11.2 Hz, 1H), 0.90 (s, 9H), 0.07 (s, 6H); IR (KBr) 3400, 2920, 1720, 1670, 1640, 1600, 1510 cm$^{-1}$ (2) To a solution of the target compound in step (1) (2.00 g, 2.88 mmol) in THF (15 mL) was added a solution (1.0 M, 3.5 mL, 3.5 mmol) of tetrabutylammonium fluoride in THF. The resulting mixture was stirred at room temperature for 5 h, poured into water (100 mL), and then extracted with ethyl acetate. The extract was washed with saturated brine, dried over anhydrous magnesium sulfate, and concentrated under reduced pressure. The residue was separated and purified by silica gel column chromatography (chloroform-methanol, 98:2) to give 1.30 g (78%) of 2-(3-benzyloxycarbonylamino-2-oxo-6-phenyl-1,2-dihydro-1-pyridyl)-N-[1-benzyl-3,3,3-trifluoro-2-hydroxypropyl] acetamide as a colorless solid.

$^1$H-NMR (500 MHz, DMSO-d$_6$) δ 8.43 (s, 1H), 8.22 (d, J=8.6 Hz, 1H), 7.88 (d, J=7.6 Hz, 1H), 7.43–7.48 (m, 3H), 7.32–7.42 (m, 5H), 7.29 (d, J=7.1 Hz, 2H), 7.17–7.23 (m, 3H), 7.11 (dd, J=7.3, 1.8 Hz, 2H), 6.67 (d, J=7.0 Hz, 1H), 6.17 (d, J=7.6 Hz, 1H), 5.19 (s, 2H), 4.38 (d, J=16.2 Hz, 1H), 4.20 (d, J=16.2 Hz, 1H), 4.06 (m, 1H), 3.91 (m, 1H), 2.90 (dd, J=14.2, 2.9 Hz, 1H), 2.76 (dd, J=14.2, 10.5 Hz, 1H); IR (KBr) 3350, 3270, 1720, 1660, 1640, 1590, 1555, 1515 cm$^{-1}$ (3) The hydroxy compound obtained above (1.20 g, 2.07 mmol) was treated with WSCI hydrochloride (3.97 g, 20.7 mmol) and dichloroacetic acid (0.65 mL, 7.9 mmol) in a mixed solution of DMSO (10 mL) and toluene (10 mL) to give 290 mg (24%) of the title compound as colorless crystals.

mp 178–181° C.; $^1$H-NMR (500 MHz, DMSO-d$_6$+D$_2$O) δ 7.89 (d, J=7.7 Hz, 1H), 7.47 (t, J=7.5 Hz, 1H), 7.33–7.45 (m, 7H), 7.13–7.23 (m, 7H), 6.19 (d, J=7.7 Hz, 1H), 5.20 (s, 2H), 4.32 (s, 2H), 4.23 (dd, J=11.5, 2.3 Hz, 1H), 3.11 (dd, J=14.1, 2.3 Hz, 1H), 2.60 (dd, J=14.1, 11.5 Hz, 1H); IR (KBr) 3380, 3270, 1720, 1665, 1640, 1600, 1515 cm$^{-1}$ MS (CI, positive) m/z 578 (MH$^+$)

EXAMPLE 14

Synthesis of 2-(3-amino-2-oxo-6-phenyl-1,2-dihydro-1-pyridyl)-N-(1-benzyl-3,3,3-trifluoro-2-oxopropyl) acetamide.

The title compound was synthesized in the same manner as in Example 2. That is, the title compound in Example 13 (79.5 mg, 0.138 mmol) was reacted under a hydrogen atmosphere in the presence of 10% palladium carbon (20 mg) in ethanol (5 mL) to give 40 mg (65%) of the title compound as pale-brown crystals.

mp 197–200° C.; $^1$H-NMR (500 MHz, DMSO-d$_6$+D$_2$O+TFA-d$_4$) δ 7.64 (d, J=7.5 Hz, 1H), 7.53 (t, J=7.5 Hz, 1H), 7.40 (t, J=7.5 Hz, 2H), 7.17–7.27 (m, 7H), 6.25(d, J=7.5 Hz, 1H), 4.39 (AB-q, J=16.7 Hz, 2H), 4.27 (m, 1H), 3.17 (dd, J=13.9, 2.5 Hz, 1H), 2.64 (dd, J=13.9, 11.5 Hz, 1H); IR (KBr) 3300, 1655, 1625, 1585, 1510 cm$^{-1}$ MS (CI, positive) m/z 444 (MH$^+$)

EXAMPLE 15

Synthesis of 2-(3-benzyloxycarbonylamino-2-oxo-5-phenyl-1,2-dihydro-1-pyridyl)-N-(1-benzyl-3,3,3-trifluoro-2-oxopropyl)acetamide.

(1) 2-(3-Benzyloxycarbonylamino-5-iodo-2-oxo-1,2-dihydro-1-pyridyl)-N-[1-benzyl-2-(tert-butyldimethylsilyl) oxy-3,3,3-trifluoropropyl]-acetamide was synthesized in the same manner as in Example 13. That is, 3-benzyloxycarbonylamino-5-iodopyrid-2-one (an intermediate in Reference Example 7, 7.40 g, 20.0 mmol) was treated with sodium hydride (60% in oil, 924 mg, 23.1 mmol) in DMF (170 mL), and then with N-[1-benzyl-2-(tert-butyldimethylsilyl)oxy-3,3,3-trifluoropropyl]-2-iodoacetamide (title compound in Reference Example 8, 11.0 g, 21.9 mmol) to give 13.2 g (88%) of the target compound as a pale-brown amorphous.

$^1$H-NMR (500 MHz, DMSO-d$_6$) δ 8.51 (s, 1H), 8.34 (d, J=7.7 Hz, 1H), 7.98 (d, J=2.2 Hz, 1H), 7.48 (d, J=2.2 Hz, 1H), 7.43 (d, J=7.1 Hz, 2H), 7.38 (t, J=7.1 Hz, 2H), 7.33 (t, J=7.1 Hz, 1H), 7.30 (t, J=7.4 Hz, 2H), 7.18–7.25 (m, 3H), 5.17 (s, 2H), 4.53 (AB-q, J=15.8 Hz, 2H), 4.29 (m, 1H), 4.11 (m, 1H), 2.97 (dd, J=14.5, 2.1 Hz, 1H), 2.73 (dd, J=14.5, 11.2 Hz, 1H), 0.93 (s, 9H), 0.22 (s, 3H), 0.12 (s, 3H); IR (KBr) 3350, 2920, 1720, 1665, 1630, 1585, 1505 cm$^{-1}$ (2) A mixture of the target compound in step (1) (5.22 g, 7.02 mmol), THF (15 mL), tetrakis(triphenylphosphine) palladium (1.62 g, 1.40 mmol), a solution of phenylboric acid (1.71 g, 14.0 mmol) in ethanol (40 mL) and 2 M aqueous sodium carbonate solution (40 mL) was stirred at 90° C. for 4 h. The resulting mixture was poured into water (100 mL), and then extracted with ethyl acetate. The extract was washed with saturated brine, dried over anhydrous magnesium sulfate, and concentrated under reduced pressure. The residue was separated and purified by silica gel column chromatography (hexane-ethyl acetate, 75:25) to give 4.62 g (95%) of 2-(3-benzyloxycarbonylamino-2-oxo-5-phenyl-1,2-dihydro-1-pyridyl)-N-[1-benzyl-2-(tert-butyldimethylsilyl)oxy-3,3,3-trifluoropropyl)acetamide as a pale-brown amorphous.

$^1$H-NMR (500 MHz, DMSO-d$_6$) δ 8.46 (s, 1H), 8.36 (d, J=7.8 Hz, 1H), 8.21 (d, J=2.4 Hz, 1H), 7.55 (d, J=2.4 Hz, 1H), 7.42–7.48 (m, 6H), 7.39 (t, J=7.1 Hz, 2H), 7.31–7.36 (m, 2H), 7.22–7.30 (m, 4H), 7.18 (t, J=7.1 Hz, 1H), 5.20 (s, 2H), 4.69 (d, J=15.8 Hz, 1H), 4.61 (d, J=15.8 Hz, 1H), 4.32 (m, 1H), 4.14 (m, 1H), 2.98 (dd, J=14.5, 2.3 Hz, 1H), 2.74 (dd, J=14.5, 11.2 Hz, 1H), 0.93 (s, 9H), 0.23 (s, 3H), 0.12 (s, 3H); IR (KBr) 3400, 2900, 1720, 1640, 1585, 1510 cm$^{-1}$ (3) 2-(3-Benzyloxycarbonylamino-2-oxo-5-phenyl-1,2-dihydro-1-pyridyl)-N-(1-benzyl-3,3,3-trifluoro-2-hydroxypropyl)acetamide was synthesized in the same manner as in Example 13. That is, the target compound in step (2) (4.18 g, 6.02 mmol) was treated with tetrabutylammonium fluoride (7.3 mmol) in THF (30 mL) to give 3.37 g (97%) of the target compound as a pale-brown solid.

$^1$H-NMR (500 MHz, DMSO-d$_6$) δ 8.49 (s, 1H), 8.44 (d, J=8.7 Hz, 1H), 8.21 (d, J=2.4 Hz, 1H), 7.50 (d, J=2.4 Hz, 1H), 7.42–7.48 (m, 6H), 7.39 (t, J=7.1 Hz, 2H), 7.31–7.36 (m, 2H), 7.22–7.28 (m, 4H), 7.16 (m, 1H), 6.70 (d, J=7.1 Hz, 1H), 5.20 (s, 2H), 4.68 (d, J=15.7 Hz, 1H), 4.54 (d, J=15.7 Hz, 1H), 4.13 (m, 1H), 4.00 (m, 1H), 2.97 (dd, J=13.9, 2.6 Hz, 1H), 2.79 (dd, J=13.9, 10.5 Hz, 1H); IR (KBr) 3370, 3280, 3050, 2910, 1720, 1650, 1590, 1560, 1515 cm$^{-1}$ (4) The hydroxy compound obtained above (2.65 g, 4.57 mmol) was treated with WSCI hydrochloride (4.38 g, 22.8 mmol) and dichloroacetic acid (0.19 mL, 2.3 mmol) in a mixed solution of DMSO (25 mL) and toluene (25 mL) to give 2.08 g (79%) of the title compound as pale-brown crystals.

mp 147–151° C.; $^1$H-NMR (500 MHz, DMSO-d$_6$+D$_2$O) δ 8.17 (s, 1H), 7.34–7.50 (m, 10H), 7.18–7.24 (m, 4H), 7.17 (d, J=2.4 Hz, 1H), 7.07 (t, J=6.9 Hz, 1H), 5.20 (s, 2H), 4.72 (d, J=15.7 Hz, 1H), 4.51 (d, J=15.7 Hz, 1H), 4.27 (dd, J=11.6, 2.6 Hz, 1H), 3.13 (dd, J=13.6, 2.6 Hz, 1H), 2.65 (dd, J=13.6, 11.6 Hz, 1H); IR (KBr) 3440, 3370, 3300, 1725, 1660, 1650, 1605, 1550, 1510 cm$^{-1}$ MS (CI, positive) m/z 578 (MH$^+$)

EXAMPLE 16

Synthesis of 2-(3-amino-2-oxo-5-phenyl-1,2-dihydro-1-pyridyl)-N-(1-benzyl-3,3,3-trifluoro-2-oxopropyl) acetamide.

The title compound was synthesized in the same manner as in Reference Example 2. That is, the title compound in Example 15 (878 mg, 1.52 mmol) was reacted under a hydrogen atmosphere in the presence of 10% palladium carbon (323 mg) in a mixed solution of ethanol (25 mL) and 1N hydrochloric acid (0.2 mL) to give 451 mg (67%) of the title compound as colorless crystals.

mp 211–213° C.; $^1$H-NMR (500 MHz, DMSO-d$_6$+D$_2$O) δ 7.38–7.47 (m, 4H), 7.32 (t, J=7.2 Hz, 1H), 7.17–7.27 (m, 4H), 7.09 (m, 1H), 6.84 (d, J=2.2 Hz, 1H), 6.72 (d, J=2.2 Hz, 1H), 4.66 (d, J=15.6 Hz, 1H), 4.42 (d, J=15.6 Hz, 1H), 4.26 (dd, J=11.5, 2.5 Hz, 1H), 3.12 (dd, J=13.6, 2.5 Hz, 1H), 2.64 (dd, J=13.6, 11.5 Hz, 1H); IR (KBr) 3300, 1665, 1635, 1580, 1535 cm$^{-1}$ MS (CI, positive) m/z 444 (MH$^+$)

EXAMPLE 17

Synthesis of 2-(3-benzyloxycarbonylamino-2-oxo-1,2-dihydro-1-pyridyl)-N-(1-benzyl-3,3,3-trifluoro-2-oxopropyl)acetamide.

(1) 2-(3-Benzyloxycarbonylamino-2-oxo-1,2-dihydro-1-pyridyl)-N-[1-benzyl-2-(tert-butyldimethysilyl)oxy-3,3,3-trifluoropropyl]acetamide was synthesized in the same manner as in Example 13. That is, 3-benzyloxycarbonylaminopyrid-2-one (an intermediate in Reference Example 7: 2.00 g, 8.19 mmol) was treated with sodium hydride (60% in oil, 365 mg, 9.13 mmol) in DMF (75 mL), and then with N-[1-benzyl-2-(tert-butyldimethylsilyl)oxy-3,3,3-trifluoropropyl]-2-iodoacetamide (title compound in Reference Example 8, 4.50 g, 8.97 mmol) to give 4.84 g (96%) of the target compound as a colorless amorphous.

$^1$H-NMR (500 MHz, DMSO-d$_6$) δ 8.31 (d, J=7.8 Hz, 1H), 8.29 (s, 1H), 7.82 (dd, J=7.1, 1.7 Hz, 1H), 7.42 (d, J=7.1 Hz, 2H), 7.38 (t, J=7.1 Hz, 2H), 7.33 (t, J=7.1 Hz, 1H), 7.29 (t, J=7.4 Hz, 2H), 7.18–7.25 (m, 3H), 7.11 (dd, J=7.1, 1.7 Hz, 1H), 6.22 (t, J=7.1 Hz, 1H), 5.17 (s, 2H), 4.54 (AB-q, J=15.7 Hz, 2H), 4.30 (m, 1H), 4.13 (m, 1H), 2.98 (dd, J=14.5, 2.3 Hz, 1H), 2.73 (dd, J=14.5, 11.3 Hz, 1H), 0.93 (s, 9H), 0.22 (s, 3H), 0.12 (s, 3H); IR (KBr) 3370, 2920, 2850, 1720, 1670, 1645, 1590, 1510 cm$^{-1}$ (2) 2-(3-Benzyloxycarbonylamino-2-oxo-1,2-dihydro-1-pyridyl)-N-(1-benzyl-3,3,3-trifluoro-2-hydroxypropyl)acetamide was synthesized in the same manner as in Example 13. That is, the target compound in step (1) (4.46 g, 7.22 mmol) was treated with tetrabutylammonium fluoride (8.7 mmol) in THF (35 mL) to give 3.55 g (98%) of the target compound as a colorless solid.

$^1$H-NMR (500 MHz, DMSO-d$_6$) δ 8.39 (d, J=8.7 Hz, 1H), 8.33 (s, 1H), 7.81 (dd, J=6.9, 1.7 Hz, 1H), 7.42 (d, J=7.1 Hz, 2H), 7.38 (d, J=7.1 Hz, 2H), 7.33 (t, J=7.1 Hz, 1H), 7.27 (t, J=7.1 Hz, 2H), 7.22 (d, J=7.1 Hz, 2H), 7.19 (t, J=7.1 Hz, 1H), 7.05 (dd, J=6.9, 1.7 Hz, 1H), 6.68 (d, J=7.1 Hz, 1H), 6.21 (t, J=6.9 Hz, 1H), 5.17 (s, 2H), 4.56 (d, J=15.7 Hz, 1H), 4.43 (d, J=15.7 Hz, 1H), 4.11 (m, 1H), 3.98 (m, 1H), 2.96 (dd, J=14.1, 2.8 Hz, 1H), 2.77 (dd, J=14.1, 10.5 Hz, 1H); IR (KBr) 3360, 3280, 1720, 1665, 1645, 1595, 1555, 1510 cm$^{-1}$ (3) The hydroxy compound obtained above (1.53 g, 3.04 mmol) was treated with WSCI hydrochloride (3.50 g, 18.3 mmol) and dichloroacetic acid (0.15 mL, 1.8 mmol) in a mixed solution of DMSO (15 mL) and toluene (15 mL) to give 1.21 g (79%) of the title compound as colorless crystals.

mp 113–117° C.; $^1$H-NMR (500 MHz, DMSO-d$_6$+D$_2$O) δ 7.80 (dd, J=7.1, 1.7 Hz, 1H), 7.37–7.43 (m, 4H), 7.34 (t, J=6.9 Hz, 1H), 7.20–7.26 (m, 4H), 7.16 (t, J=6.8 Hz, 1H), 6.81 (dd, J=7.1, 1.7 Hz, 1H), 6.21 (d, J=7.1 Hz, 1H), 5.17 (s, 2H), 4.59 (d, J=15.7 Hz, 1H), 4.40 (d, J=15.7 Hz, 1H), 4.25 (dd, J=11.5, 2.5 Hz, 1H), 3.12 (dd, J=13.7, 2.5 Hz, 1H), 2.65 (dd, J=13.7, 11.5 Hz, 1H); IR (KBr) 3400, 3290, 1720, 1660, 1645, 1600, 1505 cm$^{-1}$ MS (CI, positive) m/z 502 (MH$^+$)

EXAMPLE 18

Synthesis of 2-(3-amino-2-oxo-1,2-dihydro-1-pyridyl)-N-(1-benzyl-3,3,3-trifluoro-2-oxopropyl)acetamide.

The title compound was synthesized in the same manner as in Example 2. That is, the title compound in Example 17 (620 mg, 1.24 mmol) was reacted under a hydrogen atmosphere in the presence of 10% palladium carbon (386 mg) in a mixed solvent of ethanol (25 mL) and 1N hydrochloric acid (0.2 mL) to give 181 mg (40%) of the title compound as colorless crystals.

mp 106–112° C.; $^1$H-NMR (500 MHz, DMSO-d$_6$+D$_2$O) δ 7.26 (t, J=7.2 Hz, 2H), 7.17–7.24 (m, 3H), 6.52 (dd, J=7.0, 1.5 Hz, 1H), 6.37 (dd, J=7.0, 1.5 Hz, 1H), 6.04 (t, J=7.0 Hz, 1H), 4.53 (d, J=15.5 Hz, 1H), 4.32 (d, J=15.5 Hz, 1H), 4.26 (dd, J=11.6, 2.5 Hz, 1H), 3.12 (dd, J=13.7, 2.5 Hz, 1H), 2.64 (dd, J=13.7, 11.6 Hz, 1H); IR (KBr) 3300, 1655, 1630, 1565 cm$^{-1}$ MS (CI, positive) m/z 368 (MH$^+$)

EXAMPLE 19

Synthesis of 2-(5-benzyloxycarbonylamino-6-oxo-1,6-dihydro-1-pyrimidyl)-N-(1-benzyl-3,3,3-trifluoro-2-oxopropyl)acetamide.

(1) 2-(5-Benzyloxycarbonylamino-6-oxo-1,6-dihydro-1-pyrimidyl)-N-(1-benzyl-3,3,3-trifluoro-2-hydroxypropyl)acetamide was synthesized in the same manner as in Example 1. That is, (5-benzyloxycarbonylamino-6-oxo-1,6-dihydro-1-pyrimidinyl)acetic acid (title compound in Reference Example 10, 1.20 g, 3.96 mmol) was treated with 3-amino-1,1,1-trifluoro-4-phenyl-2-butanol (title compound in Reference Example 1, 911 mg, 4.16 mmol), WSCI hydrochloride (912 mg, 4.76 mmol) and HOBT (1.07 g, 7.92 mmol) in DMF (15 mL) to give 1.85 g (93%) of the target compound as colorless crystals.

mp 200–203° C. $^1$H-NMR (500 MHz, DMSO-d$_6$) δ 8.77 (s, 1H), 8.52 (d, J=8.7 Hz, 1H), 8.31 (s, 1H), 7.96 (s, 1H), 7.42 (d, J=7.1 Hz, 2H), 7.38 (t, J=7.1 Hz, 2H), 7.33 (t, J=7.1 Hz, 1H), 7.28 (t, J=7.4 Hz, 2H), 7.24–7.17 (m, 3H), 6.71 (d, J=7.1 Hz, 1H), 5.16 (s, 2H), 4.56 (d, J=15.9 Hz, 1H), 4.48 (d, J=15.9 Hz, 1H), 4.10 (m, 1H), 3.97 (m, 1H), 2.96 (dd, J=14.1, 2.6 Hz, 1H), 2.78 (dd, J=14.1, 10.4 Hz, 1H); IR (KBr) 3300, 1720, 1660, 1610, 1520 cm$^{-1}$ (2) The hydroxy compound obtained above (1.30 g, 2.58 mmol) was treated with WSCI hydrochloride (2.46 g, 12.8 mmol) and dichloroacetic acid (0.43 mL, 5.2 mmol) in a mixed solution of DMSO (12 mL) and toluene (12 mL) to give 722 mg (56%) of the title compound as colorless crystals.

mp 132–134° C.; $^1$H-NMR (500 MHz, DMSO-d$_6$+D$_2$O) δ 8.28 (s, 1H), 7.73 (s, 1H), 7.43–7.37 (m, 4H), 7.34 (t, J=7.0 Hz, 1H), 7.27–7.20 (m, 4H), 7.16 (t, J=6.8 Hz, 1H), 5.16 (s, 2H), 4.59 (d, J=16.0 Hz, 1H), 4.46 (d, J=16.0 Hz, 1H), 4.23 (dd, J=11.4, 2.5 Hz, 1H), 3.13 (dd, J=13.8, 2.5 Hz, 1H), 2.65 (dd, J=13.8, 11.4 Hz, 1H); IR (KBr) 3360, 1655, 1615, 1520 cm$^{-1}$ MS (CI, positive) m/z 503 (MH$^+$)

EXAMPLE 20

Synthesis of 2-(5-amino-6-oxo-1,6-dihydro-1-pyrimidyl)-N-(1-benzyl-3,3,3-trifluoro-2-oxopropyl)acetamide.

The title compound was synthesized in the same manner as in Example 6. That is, the title compound in Example 19 (385 mg, 0.766 mmol) was treated with formic acid (0.3 mL) and 10% palladium carbon (165 mg) in methanol (6 mL) to give 100 mg (35%) of the title compound as colorless crystals.

mp 129–131° C.; $^1$H-NMR (500 MHz, DMSO-d$_6$+D$_2$O) δ 7.28 (s, 1H), 7.27–7.21 (m, 4H), 7.18–7.14 (m, 2H), 4.53 (d, J=15.9 Hz, 1H), 4.37 (d, J=15.9 Hz, 1H), 4.23 (dd, J=11.5, 2.4 Hz, 1H), 3.12 (dd, J=13.7, 2.4 Hz, 1H), 2.65 (dd, J=13.7, 11.5 Hz, 1H); IR (KBr) 3430, 3270, 3060, 1680, 1650, 1610, 1550 cm$^{-1}$ MS (CI, positive) m/z 369 (MH$^+$)

EXAMPLE 21

Synthesis of 2-(5-benzyloxycarbonylamino-2-methyl-6-oxo-1,6-dihydro-1-pyrimidinyl)-N-(1-benzyl-3,3,3-trifluoro-2-oxopropyl)acetamide.

(1) 2-(5-Benzyloxycarbomylamino-2-methyl-6-oxo-1,6-dihydro-1-pyrimidyl)-N-(1-benzyl-3,3,3-trifluoro-2-hydroxypropyl)acetamide was synthesized in the same manner as in Example 1. That is, (5-benzyloxycarbonylamino-2-methyl-6-oxo-1,6-dihydro-1-pyrimidinyl)-acetic acid (title compound in Reference Example 11, 3.00 g, 9.45 mmol) was treated with 3-amino-1,1,1-trifluoro-4-phenyl-2-butanol (title compound in Reference Example 1, 2.17 g, 9.90 mmol), WSCI hydrochloride (2.17 g, 11.3 mmol) and HOBT (2.56 g, 18.9 mmol) in DMF (30 mL) to give 4.44 g (91%) of the target compound as a colorless solid.

$^1$H-NMR (500 MHz, DMSO-d$_6$) δ 8.63 (s, 1H), 8.46 (d, J=9.1 Hz, 1H), 8.17 (s, 1H), 7.43–7.35 (m, 4H), 7.32 (t, J=7.0 Hz, 1H), 7.27 (t, J=7.4 Hz, 2H), 7.23–7.17 (m, 3H), 6.72 (d, J=7.3 Hz, 1H), 5.14 (s, 2H), 4.73(d, J=16.9 Hz, 1H), 4.39 (d, J=16.9 Hz, 1H), 4.19 (m, 1H), 3.98 (m, 1H), 3.04 (dd, J=13.8, 2.7 Hz, 1H), 2.70 (dd, J=13.8, 11.2 Hz, 1H), 1.99 (s, 3H); IR (KBr) 3380, 3280, 1725, 1665, 1615, 1515 cm$^{-1}$ (2) The hydroxy compound obtained above (3.00 g, 5.79 mmol) was treated with WSCI hydrochloride (5.55 g, 28.9 mmol) and dichloroacetic acid (1.0 mL, 12 mmol) in a mixed solution of DMSO (25 mL) and toluene (25 mL) to give 2.45 g (82%) of the title compound as colorless crystals.

mp 115–118° C.; $^1$H-NMR (500 MHz, DMSO-d$_6$+D$_2$O) δ 8.14 (s, 1H), 7.42–7.36 (m, 4H), 7.33 (t, J=6.8 Hz, 1H), 7.27–7.21 (m, 4H), 7.16 (m, 1H), 5.14 (s, 2H), 4.79 (d, J=16.9 Hz, 1H), 4.40–4.30 (m, 2H), 3.15 (dd, J=13.5, 2.5 Hz, 1H), 2.64 (dd, J=13.5, 12.1 Hz, 1H), 1.87 (s, 3H); IR (KBr) 3300, 1690, 1645, 1610, 1525 cm$^{-1}$ MS (CI, positive) m/z 517 (MH$^+$)

EXAMPLE 22

Synthesis of 2-(5-amino-2-methyl-6-oxo-1,6-dihydro-1-pyrimidyl)-N-(1-benzyl-3,3,3-trifluoro-2-oxopropyl)acetamide.

The title compound was synthesized in the same manner as in Example 6. That is, the title compound in Example 21 (1.42 g, 2.75 mmol) was treated with formic acid (1.0 mL) and 10% palladium carbon (583 mg) in methanol (20 mL) to give 435 mg (41%) of the title compound as colorless crystals.

mp 117–120° C.; $^1$H-NMR (500 MHz, DMSO-d$_6$+D$_2$O) δ 7.27–7.21 (m, 4H), 7.17 (m, 1H), 7.10 (s, 1H), 4.77 (d, J=16.8 Hz, 1H), 4.36–4.28 (m, 2H), 3.15 (dd, J=13.6, 2.7 Hz, 1H), 2.64 (dd, J=13.6, 12.1 Hz, 1H), 1.78 (s, 3H); IR (KBr) 3420, 3270, 1685, 1635, 1615, 1540 cm$^{-1}$ MS (CI, positive) m/z 383 (MH$^+$)

EXAMPLE 23

Synthesis of 2-[5-benzyloxycarbonylamino-6-oxo-2-(o-tolyl)-1,6-dihydro-1-pyrimidinyl]-N-(1-benzyl-3,3,3-trifluoro-2-oxopropyl)-acetamide.

(1) 2-[5-Benzyloxycarbonylamino-6-oxo-2-(o-tolyl)-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-6-oxo-2-(o-tolyl)-1,6-dihydro-1-pyrimidinyl]acetic acid (title compound in Reference Example 12, 1.20 g, 3.05 mmol) was treated with 3-amino-1,1,1-trifluoro-4-phenyl-2-butanol (title compound in Reference Example 1, 709 mg, 3.23 mmol), WSCI hydrochloride (701 mg, 3.66 mmol) and HOBT (824 mg, 6.10 mmol) in DMF (15 mL) to give 1.66 g (92%) of the target compound as colorless crystals.

mp 217–221° C.; $^1$H-NMR (500 MHz, DMSO-d$_6$) δ 8.87 (s, 0.5H), 8.86 (s, 0.5H), 8.43 (s, 1H), 8.18 (d, J=8.4 Hz, 0.5H), 8.14 (d, J=8.6 Hz, 0.5H), 7.46–7.10 (m, 12H), 7.01 (m, 2H), 6.60 (m, 1H), 5.19 (s, 2H), 4.46 (d, J=16.4 Hz, 0.5H), 4.26 (d, J=16.2 Hz, 0.5H), 4.15 (d, J=16.2 Hz, 0.5H), 3.96 (m, 1.5H), 3.85 (m, 1H), 2.87 (m, 1H), 2.70 (m, 1H), 2.12 (s, 1.5H), 2.02 (s, 1.5H); IR (KBr) 3370, 3270, 1700, 1660, 1605, 1515 cm$^{-1}$ (2) The hydroxy compound obtained above (1.30 g, 2.19 mmol) was treated with WSCI hydrochloride (2.09 g, 10.9 mmol) and dichloroacetic acid (0.36 mL, 4.4 mmol) in a mixed solution of DMSO (10 mL) and toluene (10 mL) to give 1.30 g (100%) of the title compound as colorless crystals.

mp 127–129° C.; $^1$H-NMR (500 MHz, DMSO-d$_6$+D$_2$O) δ 8.40 (s, 1H), 7.45–7.38 (m, 5 H), 7.35 (t, J=7.1 Hz, 1H), 7.30 (d, J=7.6 Hz, 1H), 7.26–7.00 (m, 7H), 5.19 (s, 2H), 4.43 (d, J=16.5 Hz, 0.5H), 4.33 (d, J=16.0 Hz, 0.5H), 4.18–4.03 (m, 2H), 3.07 (m, 1H), 2.54 (m, 1H), 2.07 (s, 1.5H), 1.95 (s, 1.5H); IR (KBr) 3380, 3250, 3040, 1725, 1680, 1640, 1605, 1510 cm$^{-1}$ MS (CI, positive) m/z 593 (MH$^+$)

EXAMPLE 24

Synthesis of 2-[5-amino-6-oxo-2-(o-tolyl)-1,6-dihydro-1-pyrimidyl]-N-(1-benzyl-3,3,3-trifluoro-2-oxopropyl)acetamide.

The title compound was synthesized in the same manner as in Example 6. That is, the title compound in Example 23 (742 mg, 1.25 mmol) was treated with formic acid (0.4 mL) and 10% palladium carbon (271 mg) in methanol (8 mL) to give 410 mg (72%) of the title compound as a colorless amorphous.

$^1$H-NMR (500 MHz, DMSO-d$_6$+D$_2$O) δ 7.40–6.95 (m, 10H), 4.40 (d, J=16.5 Hz, 0.5H), 4.32 (d, J=16.2 Hz, 0.5H), 4.15–3.95 (m, 2H), 3.07 (m, 1H), 2.54 (m, 1H), 2.04 (s, 1.5H), 1.95 (s, 1.5H); IR (KBr) 3400, 1655, 1605 cm$^{-1}$ MS (CI, positive) m/z 459 (MH$^+$)

EXAMPLE 25

Synthesis of 2-[5-benzyloxycarbonylamino-2-(4-chlorophenyl)-6-oxo-1,6-dihydro-1-pyrimidyl]-N-(1-benzyl-3,3,3-trifluoro-2-oxopropyl)acetamide.

(1) 2-[5-Benzyloxycartonylamino-2-(4-chlorophenyl)-6-oxo-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-2-(4-chlorophenyl)-6-oxo-1,6-dihydro-1-pyrimidinyl]acetic acid (title compound in Reference Example 13, 2.50 g, 6.04 mmol) was treated with 3-amino-1,1,1-trifluoro-4-phenyl-2-butanol (title compound in Reference Example 1, 1.39 g, 6.34 mmol), WSCI hydrochloride (1.39 g, 7.25 mmol) and HOBT (1.63 g, 1.21 mmol) in DMF (20 mL) to give 3.72 g (100%) of the target compound as colorless crystals.

mp 257–262° C.; $^1$H-NMR (500 MHz, DMSO-d$_6$) δ 8.88 (s, 1H), 8.42 (s, 1H), 8.33 (d, J=8.6 Hz, 1H), 7.45–7.37 (m, 8H), 7.34 (t, J=7.1 Hz, 1H), 7.23–7.18 (m, 3H), 7.09 (m, 2H), 6.71 (brs, 1H), 5.18 (s, 2H), 4.44 (d, J=16.6 Hz, 1H), 4.19 (d, J=16.6 Hz, 1H), 4.07 (m, 1H), 3.90 (m, 1H), 2.93 (dd, J=14.1, 2.7 Hz, 1H), 2.72 (dd, J=14.1, 10.5 Hz, 1H); IR (KBr) 3420, 3260, 1705, 1660, 1600, 1520 cm$^{-1}$ (2) The hydroxy compound obtained above (2.71 g, 4.41 mmol) was treated with WSCI hydrochloride (4.23 g, 22.1 mmol) and dichloroacetic acid (0.75 mL, 9.1 mmol) in a mixed solution of DMSO (25 mL) and toluene (25 mL) to give 2.53 g (94%) of the title compound as colorless crystals.

mp 199–201° C.; $^1$H-NMR (500 MHz, DMSO-d$_6$+D$_2$O) δ 8.39 (s, 1H), 7.44 (d, J=7.1 Hz, 2H), 7.42–7.30 (m, 7H), 7.20–7.12 (m, 5 H), 5.18 (s, 2H), 4.41 (d, J=16.8 Hz, 1H), 4.30–4.20 (m, 2H), 3.11 (dd, J=14.1, 2.4 Hz, 1H), 2.59 (dd, J=14.1, 11.6 Hz, 1H); IR (KBr) 3370, 1730, 1640, 1600, 1515 cm$^{-1}$ MS (CI, positive) m/z 613, 615 (MH$^+$)

EXAMPLE 26

Synthesis of 2-[5-amino-2-(4-chlorophenyl)-6-oxo-1,6-dihydro-1-pyrimidyl]-N-(1-benzyl-3,3,3-trifluoro-2-oxopropyl)acetamide.

To a solution of the title compound in Example 25 (561 mg, 0.915 mmol) and anisole (0.32 mL, 2.9 mmol) in dichloromethane (12 mL) was added trifluoromethanesulfonic acid (0.50 mL, 5.7 mmol) under ice-cooling. The resulting mixture was stirred at 0° C.-room temperature for 1 h. Saturated aqueous sodium hydrogencarbonate solution (12 mL) was added under ice-cooling. After stirring for 30 min, the reaction mixture was poured into saturated aqueous sodium hydrogencarbonate solution (50 mL), and then extracted with ethyl acetate. The extract was washed with saturated brine and concentrated under reduced pressure to give crystals, which were washed with ethyl acetate and dried in vacuo to afford 372 mg (85%) of the title compound as colorless crystals.

mp 197–200° C.; $^1$H-NMR (500 MHz, DMSO-d$_6$+D$_2$O) δ 7.33 (d, J=8.5 Hz, 2H), 7.29 (s, 1H), 7.26 (d, J=8.5 Hz, 2H), 7.20–7.13 (m, 5H), 4.38 (d, J=16.4 Hz, 1H), 4.27–4.17 (m, 2H), 3.11 (dd, J=14.0, 2.4 Hz, 1H), 2.60 (dd, J=14.0, 11.6 Hz, 1H); IR (KBr) 3400, 3250, 1640, 1615, 1545 cm$^{-1}$ MS (CI, positive) m/z 479, 481 (MH$^+$)

EXAMPLE 27

Synthesis of 2-[5-benzyloxycarbonylamino-2-(4-methoxyphenyl)-6-oxo-1,6-dihydro-1-pyrimidyl]-N-(1-benzyl-3,3,3-trifluoro-2-oxopropyl)-acetamide.

(1) 2-[5-Benzyloxycarbonylamino-2-(4-methoxyphenyl)-6-oxo-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-2-(4-methoxyphenyl)-6-oxo-1,6-dihydro-1-pyrimidinyl]acetic acid (title compound in Reference Example 14, 5.00 g, 12.2 mmol) was treated with 3-amino-1,1,1-trifluoro-4-phenyl-2-butanol (title compound in Reference Example 1, 2.94 g, 13.4 mmol), WSCI hydrochloride (2.81 g, 14.7 mmol) and HOBT (3.29 g, 24.3 mmol) in DMF (40 mL) to give 7.23 g (97%) of the target compound as colorless crystals.

mp 217–221° C.; $^1$H-NMR (500 MHz, DMSO-d$_6$) δ 8.80 (s, 1H), 8.40 (s, 1H), 8.34 (d, J=8.7 Hz, 1H), 7.44 (d, J=7.1 Hz, 2H), 7.39 (t, J=7.1 Hz, 2H), 7.36–7.30 (m, 3H), 7.25–7.17 (m, 3H), 7.13 (d, J=6.7 Hz, 2H), 6.91 (d, J=8.8 Hz, 2H), 6.71 (d, J=7.1 Hz, 1H), 5.18 (s, 2H), 4.44 (d, J=16.5 Hz, 1H), 4.27 (d, J=16.5 Hz, 1H), 4.11 (m, 1H), 3.92 (m, 1H), 3.82 (s, 3H), 2.94 (dd, J=14.4, 2.9 Hz, 1H), 2.76 (dd, J=14.4, 10.4 Hz, 1H); IR (KBr) 3360, 3270, 3060, 2930, 1700, 1655, 1605, 1525 cm$^{-1}$ (2) The hydroxy compound obtained above (4.00 g, 6.55 mmol) was treated with WSCI hydrochloride (6.12 g, 31.9 mmol) and dichloroacetic acid (1.05 mL, 12.7 mmol) in a mixed solution of DMSO (30 mL) and toluene (30 mL) to give 3.27 g (82%) of the title compound as colorless crystals.

mp 172–174° C.; $^1$H-NMR (500 MHz, DMSO-d$_6$+D$_2$O) δ 8.38 (s, 1H), 7.44 (d, J=7.1 Hz, 2H), 7.40 (t, J=7.1 Hz, 2H), 7.35 (t, J=7.1 Hz, 1H), 7.26 (d, J=8.8 Hz, 2H), 7.24–7.16 (m, 5 H), 6.86 (d, J=8.8 Hz, 2H), 5.18 (s, 2H), 4.42 (d, J=16.4 Hz, 1H), 4.36–4.27 (m, 2H), 3.82 (s, 3H), 3.14 (d, J=14.2 Hz, 1H), 2.62 (dd, J=14.2, 11.5 Hz, 1H); IR (KBr) 3300, 1725, 1650, 1605 cm$^{-1}$ MS (CI, positive) m/z 609 (MH$^+$)

EXAMPLE 28

Synthesis of 2-[5-amino-2-(4-methoxyphenyl)-6-oxo-1,6-dihydro-1-pyrimidyl]-N-(1-benzyl-3,3,3-trifluoro-2-oxopropyl)acetamide.

The title compound was synthesized in the same manner as in Example 26. That is, the title compound in Example 27 (497 mg, 0.817 mmol) was treated with anisole (0.28 mL, 2.6 mmol) and trifluoromethanesulfonic acid (0.43 mL, 4.9 mmol) in dichloromethane (10 mL) to give 377 mg (97%) of the title compound as colorless crystals.

mp 137–140° C.; $^1$H-NMR (500 MHz, DMSO-d$_6$+D$_2$O) δ 7.30 (s, 1H), 7.24–7.15 (m, 7H), 6.82 (d, J=8.8 Hz, 2H), 4.37 (d, J=16.3 Hz, 1H), 4.31–4.23 (m, 2H), 3.81 (s, 3H), 3.13 (dd, J=14.2, 2.2 Hz, 1H), 2.63 (dd, J=14.2, 11.5 Hz, 1H); IR (KBr) 3400, 3260, 3050, 1635, 1605, 1540 cm$^{-1}$ MS (CI, positive) m/z 475 (MH$^+$)

EXAMPLE 29

Synthesis of 2-[5-amino-2-(4-hydroxyphenyl)-6-oxo-1,6-dihydro-1-pyrimidyl]-N-(1-benzyl-3,3,3-trifluoro-2-oxopropyl)acetamide.

To a solution of the title compound in Example 28 (375 mg, 0.790 mmol) in dichloromethane (10 mL) was added a solution of boron tribromide in dichloromethane (1.0 M, 16 mL, 16 mmol). The resulting mixture was stirred at room temperature for 24 h, and methanol (3 mL) was added. After stirring for 10 min, the reaction mixture was poured into saturated aqueous sodium hydrogencarbonate solution (50 mL), and then extracted with ethyl acetate. The extract was washed with saturated brine, dried over anhydrous magnesium sulfate, and concentrated under reduced pressure. The residue was separated and purified by silica gel column chromatography (chloroform-methanol, 91:9) and further purified by reversed phase column chromatography (water-acetonitrile, 67:33) to give 168 mg (46%) of the title compound as a pale-brown solid.

p$^1$H-NMR (500 MHz, DMSO-d$_6$+D$_2$O) δ 7.31 (s, 1H), 7.25–7.12 (m, 5H), 7.08 (d, J=8.6 Hz, 2H), 6.72 (d, J=8.6 Hz, 2H), 4.38 (d, J=16.2 Hz, 1H), 4.31 (d, J=16.2 Hz, 1H), 4.25 (dd, J=11.3, 2.1 Hz, 1H), 3.13 (dd, J=13.8, 2.1 Hz, 1H), 2.62 (dd, J=13.8, 11.3 Hz, 1H); IR (KBr) 3300, 1650, 1605, 1510 cm$^{-1}$ MS (CI, positive) m/z 461 (MH$^+$)

EXAMPLE 30

Synthesis of 2-[5-benzyloxycarbonylamino-2-(4-nitrophenyl)-6-oxo-1,6-dihydro-1-pyrimidinyl]-N-(1-benzyl-3,3,3-trifluoro-2-oxopropyl)-acetamide.

(1) 2-[5-Benzyloxycarbonylamino-2-(4-nitrophenyl)-6-oxo-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-2-(4-nitrophenyl)-6-oxo-1,6-dihydro-1-pyrimidinyl]acetic acid (title compound in Reference Example 15, 14.2 g, 33.5 mmol) was treated with 3-amino-1,1,1-trifluoro-4-phenyl-2-butanol (title compound in Reference Example 1, 8.08 g, 36.9 mmol), WSCI hydrochloride (7.71 g, 40.2 mmol) and HOBT (9.05 g, 67.0 mmol) in DMF (120 mL) to give 19.4 g (93%) of the target compound as colorless crystals.

mp 238–242° C.; $^1$H-NMR (500 MHz, DMSO-d$_6$) δ 8.97 (s, 1H), 8.46 (s, 1H), 8.36 (d, J=8.8 Hz, 1H), 8.21 (d, J=8.7 Hz, 2H), 7.65 (d, J=8.7 Hz, 2H), 7.44 (d, J=7.1 Hz, 2H), 7.39 (t, J=7.1 Hz, 2H), 7.34 (t, J=7.1 Hz, 1H), 7.17 (t, J=7.1 Hz, 2H), 7.13–7.06 (m, 3H), 6.71 (d, J=7.1 Hz, 1H), 5.19 (s, 2H), 4.48 (d, J=16.8 Hz, 1H), 4.19 (d, J=16.8 Hz, 1H), 4.06 (m, 1H), 3.88 (m, 1H), 2.92 (dd, J=14.1, 2.7 Hz, 1H), 2.68 (dd, J=14.1, 10.9 Hz, 1H); IR (KBr) 3360, 3270, 1720, 1660, 1590, 1510 cm$^{-1}$ (2) The hydroxy compound obtained above (9.85 g, 15.7 mmol) was treated with WSCI hydrochloride (12.9 g, 67.3 mmol) and dichloroacetic acid (2.6 mL, 32 mmol) in DMSO (75 mL) and toluene (75 mL) to give 8.94 g (91%) of the title compound as pale-yellow crystals.

mp 117–121° C.; $^1$H-NMR (500 MHz, DMSO-d$_6$+D$_2$O) δ 8.44 (s, 1H), 8.17 (d, J=8.8 Hz, 2H), 7.58 (d, J=8.8 Hz, 2H), 7.44 (d, J=7.1 Hz, 2H), 7.40 (t, J=7.1 Hz, 2H), 7.35 (t, J=7.1 Hz, 1H), 7.17–7.07 (m, 5 H), 5.19 (s, 2H), 4.47 (d, J=15.3 Hz, 1H), 4.32–4.19 (m, 2H), 3.10 (dd, J=14.1, 2.3 Hz, 1H), 2.56 (dd, J=14.1, 11.7 Hz, 1H); IR (KBr) 3290, 3050, 1725, 1640, 1595, 1515 cm$^{-1}$ MS (CI, positive) m/z 624 (MH$^+$)

EXAMPLE 31

Synthesis of 2-[5-amino-2-(4-nitrophenyl)-6-oxo-1,6-dihydro-1-pyrimidyl]-N-(1-benzyl-3,3,3-trifluoro-2-oxopropyl)acetamide.

The title compound was synthesized in the same manner as in Example 26. That is, the title compound in Example 30 (587 mg, 0.941 mmol) was treated with anisole (0.33 mL, 3.0 mmol) and trifluoromethanesulfonic acid (0.55 mL, 6.2 mmol) in dichloromethane (10 mL) to give 287 mg (62%) of the title compound as pale-brown crystals.

mp 130–134° C.; $^1$H-NMR (500 MHz, DMSO-d$_6$+D$_2$O) δ 8.12 (d, J=8.8 Hz, 2H), 7.52 (d, J=8.8 Hz, 2H), 7.33 (s, 1H), 7.18–7.08 (m, 5H), 4.45 (d, J=16.4 Hz, 1H), 4.27–4.18 (m, 2H), 3.10 (dd, J=14.1, 2.5 Hz, 1H), 2.57 (dd, J=14.1, 11.7 Hz, 1H); MS (CI, positive) m/z 490 (MH$^+$)

EXAMPLE 32

Synthesis of 2-[2-(4-aminophenyl)-5-benzyloxycarbonylamino-6-oxo-1,6-dihydro-1-pyrimidyl]-N-(1-benzyl-3,3,3-trifluoro-2-oxopropyl)-acetamide.

To a mixture of the title compound in Example 30 (2.00 g, 3.21 mmol), THF (30 mL) and water (13 mL) were added iron powder (2.15 g, 38.5 mmol) and 1N hydrochloric acid (1.7 mL). The resulting mixture was stirred at room temperature for 18 h. The reaction mixture was filtrated through Celite and insolubles were washed with ethyl acetate. The filtrate was poured into saturated aqueous sodium hydrogencarbonate solution (150 mL), and then extracted with ethyl acetate. The extract was washed with saturated brine and dried over anhydrous magnesium sulfate. The extract was concentrated and the residue was separated and purified by silica gel column chromatography (dichloromethane-ethyl acetate, 50:50) to give 1.59 g (83%) of the title compound as colorless crystals.

mp 98–101° C.; $^1$H-NMR (300 MHz, DMSO-d$_6$) δ 8.66 (s, 1H), 8.32 (s, 1H), 8.22 (d, J=9.7 Hz, 1H), 7.48–7.16 (m, 10H), 7.14 (s, 1H), 7.11 (s, 1H), 7.03 (d, J=8.6 Hz, 2H), 6.49 (d, J=8.6 Hz, 2H), 5.95–5.55 (br, 2H), 5.16 (s, 2H), 4.44 (d, J=16.6 Hz, 1H), 4.38 (d, J=16.6 Hz, 1H), 4.26 (brt, J=9.6 Hz, 1H), 3.15 (m, 1H), 2.64 (dd, J=14.0 Hz, 1H); IR (KBr) 3350, 1645, 1605 cm$^{-1}$ MS (SIMS, positive) m/z 594 (MH$^+$)

EXAMPLE 33

Synthesis of 2-[5-amino-2-(4-aminophenyl)-6-oxo-1,6-dihydro-1-pyrimidyl]-N-(1-benzyl-3,3,3-trifluoro-2-oxopropyl)acetamide.

The title compound was synthesized in the same manner as in Example 2. The title compound in Example 30 (196 mg, 0.314 mmol) was reacted under a hydrogen atmosphere in the presence of 10% palladium carbon (100 mg) in a mixed solution of acetic acid (3 mL) and perchloric acid (70%, 3 drops) to give 68 mg (44%) of the title compound as pale-yellow powdery crystals. mp >210° C. (decomposition) $^1$H-NMR (300 MHz, DMSO-d$_6$) δ 8.17 (d, J=9.6 Hz, 1H), 7.35–7.15 (m, 6H), 7.15 (s, 1H), 7.11 (s, 1H), 6.94 (d, J=8.5 Hz, 2H), 6.46 (d, J=8.5 Hz, 1H), 5.46 (s, 2H), 4.92 (s, 2H), 4.38 (d, J=16.1 Hz, 1H), 4.31 (d, J=16.1 Hz, 1H), 4.23 (brt, J=9.7 Hz, 1H), 3.14 (dd, J=14.1, 2.0 Hz, 1H), 2.65 (dd, J=14.1, 11.2 Hz, 1H); IR (KBr) 3275, 1650, 1605, 1505 cm$^{-1}$ MS (SIMS, positive) m/z 460 (MH$^+$)

EXAMPLE 34

Synthesis of 2-[5-benzyloxycarbonylamino-2-(4-dimethylaminophenyl)-6-oxo-1,6-dihydro-1-pyrimidyl]-N-(1-benzyl-3,3,3-trifluoro-2-oxopropyl)acetamide.

To a mixed solution of the title compound in Example 32 (235 mg, 0.396 mmol) in methanol (10 mL) and formalin (2 mL) was added 10% palladium carbon (89 mg) under a nitrogen atmosphere. The resulting mixture was stirred at room temperature for 1.5 h under a hydrogen atmosphere. Palladium carbon was removed by filtration and washed with methanol. The filtrate was concentrated and the residue was separated and purified by silica gel column chromatography (dichloromethane-ethyl acetate, 75:25) to give 135 mg (55%) of the title compound as colorless crystals. Recrystallization thereof from chloroform-hexane (50:50) gave 56 mg of colorless crystals. mp 220–222° C.;

$^1$H-NMR (500 MHz, DMSO-d$_6$+D$_2$O) δ 8.35 (s, 1H), 7.43 (d, J=7.1 Hz, 2H), 7.40 (t, J=7.1 Hz, 2H), 7.35 (t, J=7.1 Hz, 1H), 7.26–7.17 (m, 5H), 7.15 (d, J=8.9 Hz, 2H), 6.56 (d, J=8.9 Hz, 2H), 5.17 (s, 2H), 4.47 (d, J=16.6 Hz, 1H), 4.38–4.32 (m, 2H), 3.16 (dd, J=14.3, 2.2 Hz, 1H), 2.98 (s, 6H), 2.65 (dd, J=14.3, 11.5 Hz, 1H); IR (KBr) 3390, 3280, 1715, 1650, 1605 cm$^{-1}$ MS (CI, positive) m/z 622 (MH$^+$)

EXAMPLE 35

Synthesis of 2-[5-amino-2-(4-dimethylaminophenyl)-6-oxo-1,6-dihydro-1-pyrimidyl]-N-(1-benzyl-3,3,3-trifluoro-2-oxopropyl)acetamide.

The title compound was synthesized in the same manner as in Example 26. The title compound in Example 34 (53 mg, 0.085 mmol) was treated with anisole (0.03 mL, 0.3 mmol) and trifluoromethanesulfonic acid (0.05 mL, 0.6 mmol) in dichloromethane (3 mL) to give 36 mg (87%) of the title compound as colorless crystals.

mp 219–223° C.; $^1$H-NMR (500 MHz, DMSO-d$_6$+D$_2$O) δ 7.31 (s, 1H), 7.27–7.17 (m, 5H), 7.07 (d, J=8.8 Hz, 2H), 6.55 (d, J=8.8 Hz, 2H), 4.41 (d, J=16.2 Hz, 1H), 4.35–4.27 (m, 2H), 3.15 (dd, J=14.3, 2.2 Hz, 1H), 2.95 (s, 6H), 2.66 (dd, J=14.3, 11.4 Hz, 1H); IR (KBr) 3280, 1635, 1605 cm$^{-1}$ MS (SIMS, positive) m/z 488 (MH$^+$)

EXAMPLE 36

Synthesis of 2-[5-methylamino-2-(4-dimethylaminophenyl)-6-oxo-1,6-dihydro-1-pyrimidyl]-N-(1-benzyl-3,3,3-trifluoro-2-oxopropyl)-acetamide.

To a solution of the title compound in Example 34 (90 mg, 0.148 mmol) in a mixed solution of methanol (4 mL) and formic acid (0.2 mL) was added 10% palladium carton (31 mg) under a nitrogen atmosphere. The resulting mixture was stirred for 16 h under a hydrogen atmosphere. Palladium carbon was removed by filtration and washed with methanol. The filtrate was concentrated, poured into saturated aqueous sodium hydrncarbonate solution (50 mL), and then extracted with ethyl acetate. The extract was washed with saturated brine and the solvent was evaporated under reduced pressure. The residue was separated and purified by silica gel column chromatography (chloroform-methanol, 97:3) gave 46 mg (62%) of the title compound as pale-yellow crystals. Recrystallization thereof from chloroform-hexane (50:50) afforded 23 mg of pale-yellow crystals.

mp 270–275° C.; $^1$H-NMR (500 MHz, DMSO-d$_6$+D$_2$O) δ 7.27–7.17 (m, 5H), 7.07 (d, J=8.9 Hz, 2H), 7.00 (s, 1H), 6.55 (d, J=8.9 Hz, 2H), 4.42 (d, J=16.3 Hz, 1H), 4.34–4.27 (m, 2H), 3.15 (dd, J=14.3, 2.2 Hz, 1H), 2.95 (s, 6H), 2.70 (s, 3H), 2.65 (dd, J=14.3, 11.4 Hz, 1H); IR (KBr) 3360, 1635, 1605 cm$^{-1}$ MS (SIMS, positive) m/z 502 (MH$^+$)

EXAMPLE 37

Synthesis of 2-[2-(4-acetylaminophenyl)-5-benzyloxycarbonylamino-6-oxo-1,6-dihydro-1-pyrimidyl]-N-(1-benzyl-3,3,3-trifluoro-2-oxopropyl)acetamide.

To a solution of the title compound in Example 32 (310 mg, 0.522 mmol) in THF (8 mL) was added sodium carbonate (220 mg, 2.08 mmol), and after cooling with ice, acetyl chloride (0.07 mL, 1 mmol) was added. The resulting mixture was stirred at 0° C. for 1 h, poured into 1N hydrochloric acid (40 L), and then extracted with ethyl acetate. The extract was washed with saturated aqueous sodium hydrogencarbonate solution (40 mL) and saturated brine, and dried over anhydrous maanesium sulfate. The extract was concentrated and the residue was separated and purified by silica gel column chromatography (chloroform-methanol, 95:5) to give 330 mg (99%) of the title compound as colorless crystals.

mp 235–240° C. $^1$H-NMR (500 MHz, DMSO-d$_6$+D$_2$O) δ 8.38 (s, 1H), 7.59 (d, J=8.6 Hz, 2H), 7.45–7.35 (m, 5H), 7.25–7.13 (m, 7H), 5.19 (s, 2H), 4.44 (d, J=16.4 Hz, 1H), 4.34 (d, J=16.4 Hz, 1H), 4.26 (m, 1H), 3.14 (dd, J=14.0, 2.2 Hz, 1H), 2.60 (dd, J=14.0, 11.7 Hz, 1H), 2.14 (s, 3H); IR (KBr) 3250, 1720, 1650, 1595 cm$^{-1}$ MS (SIMS, positive) m/z 636 (MH$^+$)

EXAMPLE 38

Synthesis of 2-[5-amino-2-(4-acetylaminophenyl)-6-oxo-1,6-dihydro-1-pyrimidyl]-N-(1-benzy1–3,3,3-trifluoro-2-oxopropyl)acetamide.

The title compound was synthesized in the same manner as in Example 6. That is, the title compound in Example 37 (107 mg, 0.168 mmol) was treated with formic acid (0.25 mL) and 10% palladium carbon (38 mg) in methanol (5 mL) to give 39 mg (46%) of the title compound as a pale-yellow solid.

$^1$H-NMR (500 MHz, DMSO-d$_6$+D$_2$O) δ 7.55 (d, J=8.6 Hz, 2H), 7.31 (s, 1H), 7.25–7.14 (m, 7H), 4.38 (d, J=16.5 Hz, 1H), 4.28 (d, J=16.5 Hz, 1H), 4.23 (dd, J=11.5, 2.2 Hz, 1H), 3.13 (dd, J=13.9, 2.2 Hz, 1H), 2.61 (dd, J=13.9, 11.5 Hz, 1H), 2.11 (s, 3H); IR (KBr) 3280, 1650, 1595, 1530, 1505 cm$^{-1}$ MS (CI, positive) m/z 502 (MH$^+$)

EXAMPLE 39

Synthesis of 2-[5-benzyloxycartonylamino-2-(4-trifluoromethanesulfonylaminophenyl)-6-oxo-1,6-dihydro-1-pyrimidyl]-N-(1-benzyl-3,3,3-trifluoro-2-oxopropyl) acetamide.

To a solution of the title compound in Example 32 (300 mg, 0.505 mmol) and triethylamine (0.09 mL, 0.6 mmol) in THF (10 mL) was added trifluoromethanesulfonyl anhydride (0.10 mL, 0.59 mmol) at −78° C. The resulting mixture was stirred at −78° C. for 1.5 h, and water (2 mL) was added. After stirring at room temperature for 30 min, the reaction mixture was poured into water (50 mL), and then extracted with ethyl acetate. The extract was dried over anhydrous magnesium sulfate and the solvent was evaporated under reduced pressure. The residue was separated and purified by silica gel column chromatography (dichloromethane-ethyl acetate, 75:25) to give 312 mg (85%) of the title compound as colorless crystals. Recrystallization thereof from chloroform-hexane (50:50) afforded 223 mg of colorless crystals.

mp 135–138° C.; $^1$H-NMR (500 MHz, DMSO-d$_6$+D$_2$O) δ 8.39 (s, 1H), 7.45–7.33 (m, 7H), 7.27 (d, J=8.7 Hz, 2H), 7.21–7.14 (m, 5H), 5.19 (s, 2H), 4.36 (brs, 2H), 4.25 (dd, J=11.4, 2.4 Hz, 1H), 3.13 (dd, J=14.0, 2.4 Hz, 1H), 2.59 (dd, J=14.0, 11.4 Hz, 1H); IR (KBr) 3300, 1725, 1650, 1515 cm$^{-1}$ MS (SIMS, positive) m/z 726 (MH$^+$)

EXAMPLE 40

Synthesis of 2-[5-amino-2-(4-trifluoromethanesulfonylaminophenyl)-6-oxo-1,6-dihydro-1-pyrimidyl]-N-(1-benzyl-3,3,3-trifluoro-2-oxopropyl) acetamide.

The title compound was synthesized in the same manner as in Example 26. The title compound in Example 39 (100 mg, 0.138 mmol) was treated with anisole (0.05 mL, 0.5 mmol) and trifluoromethanesulfonic acid (0.075 mL, 0.85 mmol) in dichloromethane (8 mL) to give 77 mg (94%) of the title compound as colorless crystals.

mp 188–191° C.; $^1$H-NMR (500 MHz, DMSO-$_6$+D$_2$O) δ 7.36 (d, J=8.7 Hz, 2H), 7.32 (s, 1H), 7.30 (d, J=8.7 Hz, 2H), 7.21–7.14 (m, 5H), 4.42–4.30 (m, 2H), 4.26 (dd, J=11.5, 2.4 Hz, 1H), 3.14 (dd, J=13.9, 2.4 Hz, 1H), 2.59 (dd, J=13.9, 11.5 Hz, 1H); IR (KBr) 3400, 3250, 3050, 1645, 1615, 1555 cm$^{-1}$ MS (SIMS, positive) m/z 592 (MH$^+$)

EXAMPLE 41

Synthesis of 2-[5-benzyloxycarbonylamino-2-(4-isopropoxycarbonylaminophenyl)-6-oxo-1,6-dihydro-1-pyrimidyl]-N-(1-benzyl-3,3,3-trifluoro-2-oxopropyl) acetamide.

The title compound was synthesized in the same manner as in Example 37. The title compound in Example 32 (300 mg, 0.505 mmol) was reacted with isopropyl chloroformate (0.12 mL, 1.1 mmol) in the presence of sodium carbonate (106 mg, 1.00 mmol) in THF (8 mL) to give 320 mg (93%) of the title compound as colorless crystals.

mp 219–221° C.; $^1$H-NMR (500 MHz, DMSO-d$_6$+D$_2$O) δ 8.38 (s, 1H), 7.48 (d, J=8.7 Hz, 2H), 7.45–7.38 (m, 4H), 7.35 (t, J=7.0 Hz, 1H), 7.23–7.13 (m, 7H), 5.18 (s, 2H), 4.95 (sept, J=6.2 Hz, 1H), 4.44 (d, J=16.4 Hz, 1H), 4.33 (d, J=16.4 Hz, 1H), 4.24 (dd, J=11.4, 2.2 Hz, 1H), 3.13 (dd, J=13.9, 2.2 Hz, 1H), 2.60 (dd, J=13.9, 11.4 Hz, 1H), 1.29 (d, J=6.2 Hz, 6H); IR (KBr) 3250, 1720, 1690, 1655, 1605, 1500 cm$^{-1}$ MS (CI, positive) m/z 680 (MH$^+$)

EXAMPLE 42

Synthesis of 2-[5-amino-2-(4-isopropoxycarbonylaminophenyl)-6-oxo-1,6-dihydro-1-pyrimidyl]-N-(1-benzyl-3,3,3-trifluoro-2-oxopropyl)acetamide.

The title compound was synthesized in the same manner as in Example 2. That is, the title compound in Example 41 (88 mg, 0.13 mmol) was reacted under a hydrogen atmosphere in the presence of 10% palladium carbon (29 mg) in methanol (5 mL) to give 52 mg (73%) of the title compound as pale-yellow crystals.

mp 131–135° C.; $^1$H-NMR (500 MHz, DMSO-d$_6$+D$_2$O) δ 7.44 (d, J=8.7 Hz, 2H), 7.31 (s, 1H), 7.23–7.12 (m, 7H), 4.94 (sept, J=6.2 Hz, 1H), 4.39 (d, J=16.3 Hz, 1H), 4.28 (d, J=16.3 Hz, 1H), 4.23 (dd, J=11.3, 2.1 Hz, 1H), 3.13 (dd, J=14.0, 2.1 Hz, 1H), 2.61 (dd, J=14.0, 11.3 Hz, 1H), 1.29 (d, J=6.2 Hz, 6H); IR (KBr) 3380, 1690, 1660, 1610, 1510 cm$^{-1}$ MS (CI, positive) m/z 546 (MH$^+$)

EXAMPLE 43

Synthesis of 2-[5-benzyloxycarbonylamino-2-(3,5-dinitrophenyl)-6-oxo-1,6-dihydro-1-pyrimidyl]-N-(1-benzyl-3,3,3-trifluoro-2-oxopropyl)-acetamide.

(1) 2-[5-Benzyloxycarbonylamino-2-(3,5-dinitrophenyl)-6-oxo-1,6-dihydro-1-pyrimidyl]-N-(1-benzyl-3,3,3-trifluoro-2-hydroxypropyl)-acetamide was synthesized in the same manner as in Example 1. That is, [5-benzyloxycarbonylamino-2-(3,5-dinitrophenyl)-6-oxo-1,6-dihydro-1-pyrimidinyl]acetic acid (title compound in Reference Example 16, mixture with diethyl ether, 3.74 g, 7.08 mmol) was treated with 3-amino-1,1,1-trifluoro-4-phenyl-2-butanol (title compound in Reference Example 1, 1.78 g, 8.12 mmol), WSCI hydrochloride (1.63 g, 8.50 mmol) and HOBT (1.91 g, 14.1 mmol) in DMF (25 mL) to give 4.06 g (86%) of the target compound as a dark-brown solid.

$^1$H-NMR (500 MHz, DMSO-d$_6$) δ 9.06 (s, 1H), 8.94 (t, J=2.1 Hz, 1H), 8.71 (d, J=2.1 Hz, 2H), 8.49 (s, 1H), 8.40 (d, J=8.7 Hz, 1H), 7.45 (d, J=7.1 Hz, 2H), 7.40 (t, J=7.1 Hz, 2H), 7.34 (t, J=7.1 Hz, 1H), 7.14–7.05 (m, 5H), 6.62 (d, J=7.3 Hz, 1H), 5.20 (s, 2H), 4.51 (d, J=16.8 Hz, 1H), 4.36 (d, J=16.8 Hz, 1H), 3.98 (m, 1H), 3.85 (m, 1H), 2.89 (dd, J=14.1, 2.9 Hz, 1H), 2.65 (dd, J=14.1, 10.6 Hz, 1H); IR (KBr) 3280, 3090, 1720, 1665, 1510 cm$^{-1}$ (2) The hydroxy compound obtained above (3.22 g, 4.80 mmol) was treated with WSCI hydrochloride (4.60 g, 24.0 mmol) and dichloroacetic acid (0.80 mL, 9.7 mmol) in a mixed solution of DMSO (20 mL) and toluene (20 mL) to give 2.70 g (84%) of the title compound as pale-brown crystals.

mp 154–157° C.; $^1$H-NMR (500 MHz, DMSO-d$_6$+D$_2$O) δ 8.97 (t, J=2.0 Hz, 1H), 8.63 (d, J=2.0 Hz, 2H), 8.45 (s, 1H), 7.45 (d, J=7.1 Hz, 2H), 7.41 (t, J=7.1 Hz, 2H), 7.36 (t, J=7.1 Hz, 1H), 7.09–7.00 (m, 5 H), 5.20 (s, 2H), 4.48 (brs, 2H), 4.09 (dd, J=11.7, 2.5 Hz, 1H), 3.03 (dd, J=13.7, 2.5 Hz, 1H), 2.49 (dd, J=13.7, 11.7 Hz, 1H); IR (KBr) 3300, 3070, 1725, 1655, 1540, 1515 cm$^{-1}$ MS (SIMS, positive) m/z 687 (M+H$_2$O+H$^+$)

EXAMPLE 44

Synthesis of 2-[5-amino-2-(3,5-dinitrophenyl)-6-oxo-1,6-dihydro-1-pyrimidyl]-N-(1-benzyl-3,3,3-trifluoro-2-oxopropyl)acetamide.

The title compound was synthesized in the same manner as in Example 26. The title compound in Example 43 (405 mg, 0.606 mmol) was treated with anisole (0.21 mL, 1.9 mmol) and trifluoromethanesulfonic acid (0.29 mL, 3.3 mmol) in dichloromethane (7 mL) to give 305 mg (94%) of the title compound as yellow crystals.

mp 206–209° C.; $^1$H-NMR (500 MHz, DMSO-d$_6$+D$_2$O) δ 8.91 (t, J=2.1 Hz, 1H), 8.56 (d, J=2.1 Hz, 2H), 7.34 (s, 1H), 7.10–7.01 (m, 5H), 4.45 (brs, 2H), 4.10 (dd, J=11.4, 2.6 Hz, 1H), 3.03 (dd, J=13.7, 2.6 Hz, 1H), 2.50 (dd, J=13.7, 11.4 Hz, 1H); IR (KBr) 3280, 3070, 1660, 1605, 1540 cm$^{-1}$ MS (CI, positive) m/z 535 (MH$^+$)

EXAMPLE 45

Synthesis of 2-[2-(3,5-diaminophenyl)-5-benzyloxycarbonylamino-6-oxo-1,6-dihydro-1-pyrimidyl]-N-(1-benzyl-3,3,3-trifluoro-2-oxopropyl)-acetamide.

The title compound was synthesized in the same manner as in Example 32. That is, the title compound in Example 43 (887 mg, 1.33 mmol) was treated with iron powder (890 mg, 15.9 mmol) and 1N hydrochloric acid (0.7 mL) in a mixed solution of THF (13 mL) and water (6 mL) to give 788 mg (97%) of the title compound as pale-yellow crystals.

mp 178–181° C.; $^1$H-NMR (500 MHz, DMSO-d$_6$+D$_2$O) δ 8.34 (s, 1H), 7.45–7.38 (m, 4H), 7.36 (t, J=6.9 Hz, 1H), 7.20 (t, J=7.0 Hz, 2H), 7.17–7.11 (m, 3H), 6.00 (t, J=2.0 Hz, 1H), 5.82 (d, J=2.0 Hz, 2H), 5.18 (s, 1H), 4.51 (d, J=16.0 Hz, 1H), 4.44 (d, J=16.0 Hz, 1H), 4.10 (dd, J=11.4, 2.4 Hz, 1H), 3.09 (dd, J=14.2, 2.4 Hz, 1H), 2.66 (dd, J=14.2, 11.4 Hz, 1H); IR (KBr) 3420, 3330, 1680, 1645, 1600, 1520 cm$^{-1}$ MS (CI, positive) m/z 609 (MH$^+$)

EXAMPLE 46

Synthesis of 2-[5-amino-2-(3,5-diaminophenyl)-6-oxo-1,6-dihydro-1-pyrimidyl]-N-(1-benzyl-3,3,3-trifluoro-2-oxopropyl)acetamide.

The title compound was synthesized in the same manner as in Example 2. The title compound in Example 45 (150 mg, 0.246 mmol) was reacted under a hydrogen atmosphere in the presence of 10% palladium carbon (56 mg) in a mixed solution of methanol (5 mL) and THF (3 mL) to give 104 mg (89%) of the title compound as pale-brown crystals.

mp 127–130° C.; $^1$H-NMR (500 MHz, DMSO-d$_6$+D$_2$O) δ 7.26 (s, 1H), 7.21 (t, J=7.0 Hz, 2H), 7.16–7.12 (m, 3H), 5.93 (t, J=2.0 Hz, 1H), 5.77 (d, J=2.0 Hz, 2H), 4.45 (d, J=15.9 Hz, 1H), 4.39 (d, J=15.9 Hz, 1H), 4.05 (m, 1H), 3.08 (dd, J=14.0, 2.4 Hz, 1H), 2.69 (dd, J=14.0, 11.2 Hz, 11H); IR (KBr) 3320, 1650, 1600, 1520 cm$^{-1}$ MS (CI, positive) m/z 475 (MH$^+$)

EXAMPLE 47

Synthesis of 2-[5-benzyloxycarbonylamino-6-oxo-2-(3-pyridyl)-1,6-dihydro-1-pyrimidyl]-N-(1-benzyl-3,3,3-trifluoro-2-oxopropyl)-acetamide.

(1) 2-[5-Benzyloxycarbonylamino-6-oxo-2-(3-pyridyl)-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-6-oxo-2-(3-pyridyl)-1,6-dihydro-1-pyrimidinyl]acetic acid (title compound in Reference Example 17, 2.50 g, 6.57 mmol) was treated with 3-amino-1,1,1-trifluoro-4-phenyl-2-butanol (title compound in Reference Example 1, 1.51 g, 6.89 mmol), WSCI hydrochloride (1.51 g, 7.88 mmol) and HOBT (1.77 g, 13.1 mmol) in DMF (25 mL) to give 3.58 g (94%) of the target compound as colorless crystals.

mp 205–209° C.; $^1$H-NMR (500 MHz, DMSO-d$_6$) δ 8.92 (s, 1H), 8.70 (dd, J=4.9, 1.6 Hz, 1H), 8.64 (d, J=2.1 Hz, 1H), 8.45 (s, 1H), 8.35 (d, J=8.7 Hz, 1H), 7.76 (m, 1H), 7.44 (d, J=7.1 Hz, 2H), 7.42–7.37 (m, 3H), 7.34 (t, J=7.1 Hz, 1H), 7.23–7.16 (m, 3H), 7.08 (d, J=7.2 Hz, 2H), 6.69 (d, J=7.1 Hz, 1H), 5.19 (s, 2H), 4.45 (d, J=16.8 Hz, 1H), 4.29 (d, J=16.8 Hz, 1H), 4.03 (m, 1H), 3.88 (sext, J=7.1 Hz, 1H), 2.92 (dd, J=14.2, 2.9 Hz, 1H), 2.71 (dd, J=14.2, 10.4 Hz, 1H); IR (KBr) 3370, 3280, 3050, 1720, 1665, 1600, 1515 cm$^{-1}$ (2) The hydroxy compound obtained above (2.76 g, 4.75 mmol) was treated with WSCI hydrochloride (4.55 g, 23.7 mmol) and dichloroacetic acid (0.80 mL, 9.7 mmol) in a mixed solution of DMSO (20 mL) and toluene (20 mL) to give 2.39 g (87%) of the title compound as colorless crystals.

mp 88–91° C.; $^1$H-NMR (500 MHz, DMSO-d$_6$+D$_2$O) δ 8.69 (dd, J=4.9, 1.6 Hz, 1H), 8.56 (d, J=2.2 Hz, 1H), 8.43 (s, 1H), 7.68 (m, 1H), 7.46–7.33 (m, 6H), 7.20–7.10 (m, 5H), 5.19 (s, 2H), 4.41 (m, 2H), 4.20 (dd, J=11.4, 2.5 Hz, 1H), 3.10 (dd, J=14.0, 2.5 Hz, 1H), 2.57 (dd, J=14.0, 11.4 Hz, 1H); IR (KBr) 3300, 1720, 1655, 1595, 1510 cm$^{-1}$ MS (CI, positive) m/z 580 (MH$^+$)

EXAMPLE 48

Synthesis of 2-[5-amino-6-oxo-2-(3-pyridyl)-1,6-dihydro-1-pyrimidyl]-N-(1-benzyl-3,3,3-trifluoro-2-oxopropyl)acetamide.

The title compound was synthesized in the same manner as in Example 2. That is, the title compound in Example 47 (200 mg, 0.345 mmol) was reacted under a hydrogen atmosphere in the presence of 10% palladium carbon (144 mg) in a mixed solution of methanol (6 mL) and THF (4 mL) to give 111 mg (72%) of the title compound as a colorless solid.

$^1$H-NMR (500 MHz, DMSO-d$_6$+D$_2$O) δ 8.63 (dd, J=4.8, 1.5 Hz, 1H), 8.50 (d, J=1.8 Hz, 1H), 7.61 (m, 1H), 7.33 (s, 1H), 7.32 (dd, J=7.9, 4.8 Hz, 1H), 7.20–7.11 (m, 5H), 4.35 (AB-q, J=16.9 Hz, 2H), 4.20 (dd, J=11.3, 2.3 Hz, 1H), 3.10 (dd, J=14.0, 2.3 Hz, 1H), 2.58 (dd, J=14.0, 11.3 Hz, 1H); IR (KBr) 3410, 3270, 1690, 1650, 1605, 1535 cm$^{-1}$ MS (CI, positive) m/z 446 (MH$^+$)

EXAMPLE 49

Synthesis of 2-[5-benzyloxycarbonylamino-6-oxo-2-(4-pyridyl)-1,6-dihydro-1-pyrimidyl]-N-(1-benzyl-3,3,3-trifluoro-2-oxopropyl)-acetamide.

(1) 2-[5-Benzyloxycarbonylamino-6-oxo-2-(4-pyridyl)-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-6-oxo-2-(4-pyridyl)-1,6-dihydro-1-pyrimidinyl]acetic acid (title compound in Reference Example 18, 2.66 g, 6.57 mmol) was treated with 3-amino-1,1,1-trifluoro-4-phenyl-2-butanol (title compound in Reference Example 1, 1.51 g, 6.89 mmol), WSCI hydrochloride (1.51 g, 7.88 mmol) and HOBT (1.77 g, 13.1 mmol) in DMF (25 mL) to give 3.59 g (94%) of the target compound as pale-yellow crystals.

mp 213–217° C.; $^1$H-NMR (500 MHz, DMSO-d$_6$) δ 8.96 (s, 1H), 8.62 (d, J=5.9 Hz, 2H), 8.45 (s, 1H), 8.36 (d, J=8.7 Hz, 2H), 7.44 (d, J=7.1 Hz, 2H), 7.42–7.32 (m, 5H), 7.23–7.16 (m, 3H), 7.09 (d, J=7.0 Hz, 2H), 6.71 (d, J=7.1 Hz, 1H), 5.19 (s, 2H), 4.42 (d, J=16.7 Hz, 1H), 4.23 (d, J=16.7 Hz, 1H), 4.07 (m, 1H), 3.89 (sext, J=7.1 Hz, 1H), 2.94 (dd, J=14.2, 2.8 Hz, 1H), 2.71 (dd, J=14.2, 10.6 Hz, 1H); IR (KBr) 3380, 3270, 1725, 1660, 1595, 1515 cm$^{-1}$ (2) The hydroxy compound obtained above (2.79 g, 4.80 mmol) was treated with WSCI hydrochloride (4.60 g, 24.0 mmol) and dichloroacetic acid (0.80 mL, 9.7 mmol) in a mixed solution of DMSO (20 mL) and toluene (20 mL) to give 2.24 g (81%) of the title compound as pale-yellow crystals.

mp 182–185° C. $^1$H-NMR (500 MHz, DMSO-d$_6$+D$_2$O) δ 8.58 (d, J=6.0 Hz, 2H), 8.43 (s, 1H), 7.44 (d, J=7.1 Hz, 2H), 7.40 (t, J=7.1 Hz, 2H), 7.36 (t, J=7.1 Hz, 1H), 7.30 (d, J=6.0 Hz, 2H), 7.20–7.12 (m, 5H), 5.19 (s, 2H), 4.40 (d, J=16.5 Hz, 1H), 4.32 (m, 1H), 4.25 (dd, J=11.5, 2.5 Hz, 1H), 3.11 (dd, J=14.0, 2.5 Hz, 1H), 2.58 (dd, J=14.0, 11.5 Hz, 1H); IR (KBr) 3380, 3290, 3030, 1725, 1660, 1595, 1515 cm$^{-1}$ MS (CI, positive) m/z 580 (MH$^+$)

EXAMPLE 50

Synthesis of 2-[5-amino-6-oxo-2-(4-pyridyl)-1,6-dihydro-1-pyrimidyl]-N-(1-benzyl-3,3,3-trifluoro-2-oxopropyl)acetamide.

The title compound was synthesized in the same manner as in Example 2. The title compound in Example 49 (250 mg, 0.431 mmol) was treated under a hydrogen atmosphere in the presence of 10% palladium carbon (114 mg) in a mixed solution of methanol (6 mL) and THF (4 mL) to give 161 mg (84%) of the title compound as a pale-yellow solid.

$^1$H-NMR (500 MHz, DMSO-d$_6$+D$_2$O) δ 8.52 (d, J=6.0 Hz, 2H), 7.32 (s, 1H), 7.24 (d, J=6.0 Hz, 2H), 7.19–7.13 (m, 5H), 4.38 (d, J=16.1 Hz, 1H), 4.29 (m, 1H), 4.25 (dd, J=11.5, 2.5 Hz, 1H), 3.11 (dd, J=14.1, 2.5 Hz, 1H), 2.59 (dd, J=14.1, 11.5 Hz, 1H); IR (KBr) 3420, 3360, 3050, 1650, 1615, 1595, 1540 cm$^{-1}$ MS (CI, positive) m/z 446 (MH$^+$)

EXAMPLE 51

Synthesis of 2-[5-benzyloxycarbonylamino-6-oxo-2-(2-thienyl)-1,6-dihydro-1-pyrimidyl]-N-(1-benzyl-3,3,3-trifluoro-2-oxopropyl)-acetamide.

(1) 2-[5-Benzyloxycarbonylamino-6-oxo-2-(2-thienyl)-1,6-dihydro-1-pyrimidyl]-N-(1-benzyl-3,3,3-trifluoro-2-hydroxypropyl)acetamide was synthesized in the same manner as in Example 1. That is, [5-benzyloxycarbonylamino-6-oxo-2-(2-thienyl)-1,6-dihydro-1-pyrimidinyl]acetic acid (title compound in Reference Example 19, 2.00 g, 4.84 mmol) was treated with 3-amino-1,1,1-trifluoro-4-phenyl-2-butanol (title compound in Reference Example 1, 1.11 g, 5.06 mmol), WSCI hydrochloride (1.11 g, 5.79 mmol) and HOBT (1.31 g, 9.69 mmol) in DMF (20 mL) to give 2.66 g (94%) of the target compound as pale-yellow crystals.

mp 228–230° C.; $^1$H-NMR (500 MHz, DMSO-d$_6$) δ 8.87 (s, 1H), 8.54 (d, J=8.9 Hz, 1H), 8.39 (s, 1H), 7.77 (dd, J=5.1, 1.0 Hz, 1H), 7.43 (d, J=7.1 Hz, 2H), 7.39 (t, J=7.1 Hz, 2H), 7.36–7.19 (m, 6H), 6.98 (dd, J=5.1, 3.8 Hz, 1H), 6.89 (m, 1H), 6.76 (d, J=7.1 Hz, 1H), 5.18 (s, 2H), 4.72 (d, J=16.8 Hz, 1H), 4.50 (d, J=16.8 Hz, 1H), 4.23 (m, 1H), 3.95 (m, 1H), 3.02 (dd, J=14.1, 2.8 Hz, 1H), 2.75 (dd, J=14.1, 11.0 Hz, 1H); IR (KBr) 3380, 3260, 1705, 1660, 1595, 1525 cm$^{-1}$ (2) The hydroxy compound obtained above (1.80 g, 3.07 mmol) was treated with WSCI hydrochloride (2.94 g, 15.3 mmol) and dichloroacetic acid (0.50 mL, 6.1 mmol) in a mixed solution of DMSO (15 mL) and toluene (15 mL) to give 1.47 g (82%) of the title compound as pale-yellow crystals.

mp 108–111° C.; $^1$H-NMR (500 MHz, DMSO-d$_6$+D$_2$O) δ 8.36 (s, 1H), 7.75 (d, J=59.1 Hz, 1H), 7.43 (d, J=7.1 Hz, 2H), 7.39 (t, J=7.1 Hz, 2H), 7.34 (t, J=7.1 Hz, 1H), 7.29–7.22 (m, 5 H), 6.97 (dd, J=5.1, 3.8 Hz, 1H), 6.77 (brs, 1H), 5.18 (s, 2H), 4.73 (d, J=16.7 Hz, 1H), 4.50 (d, J=16.7 Hz, 1H), 4.39 (dd, J=11.8, 2.3 Hz, 1H), 3.19 (dd, J=13.8, 2.3 Hz, 1H), 2.66 (dd, J=13.8, 11.8 Hz, 1H); IR (KBr) 3280, 1720, 1640, 1595, 1530 cm$^{-1}$ MS (CI, positive) m/z 585 (MH$^+$)

EXAMPLE 52
Synthesis of 2-[5-amino-6-oxo-2-(2-thienyl)-1,6-dihydro-1-pyrimidyl]-N-(1-benzyl-3,3,3-trifluoro-2-oxopropyl) acetamide.

The title compound was synthesized in the same manner as in Example 26. That is, the title compound in Example 51 (760 mg, 1.30 mmol) was treated with anisole (0.45 mL, 4.1 mmol) and trifluoromethanesulfonic acid (0.70 mL, 7.9 mmol) in dichloromethane (15 mL) to give 415 mg (71%) of the title compound as pale-yellow crystals.

mp 198–201° C.; $^1$H-NMR (500 MHz, DMSO-d$_6$+D$_2$O) δ 7.60 (d, J=5.1 Hz, 1H), 7.28–7.22 (m, 6H), 6.91 (dd, J=5.1, 3.7 Hz, 1H), 6.64 (brs, 1H), 4.68 (d, J=16.5 Hz, 1H), 4.43 (d, J=16.5 Hz, 1H), 4.37 (dd, J=11.6, 2.4 Hz, 1H), 3.18 (dd, J=13.9, 2.4 Hz, 1H), 2.65 (dd, J=13.9, 11.6 Hz, 1H); IR (KBr) 3400, 3250, 1640, 1605, 1530 cm$^{-1}$ MS (CI, positive) m/z 481 (MH$^+$)

EXAMPLE 53
Synthesis of 2-[5-[4-(carboxy)benzyloxycarbonyl]amino-6-oxo-2-phenyl-1,6-dihydro-1-pyrimidyl]-N-(1-benzyl-3,3,3-trifluoro-2-oxopropyl)-acetamide.

(1) 2-(5-Benzyloxycarbonylamino-6-oxo-2-phenyl-1,6-dihydro-1-pyrimidyl)-N-[1-benzyl-2-(tert-butyldimethylsilyl)oxy-3,3,3-trifluoropropyl]acetamide was synthesized in the same manner as in the synthesis of N-[1-benzyl-2-(tert-butyldimethylsilyl)oxy-3,3,3-trifluoropropyl]-2-chloroacetamide which was an intermediate in Reference Example 8. That is, the target compound in Example 1-(1) (3.50 g, 6.03 mmol) was treated with 2,6-lutidine (1.05 mL, 9.04 mmol) and tert-butyldimethylsilyl triflate (2.92 mL, 12.7 mmol) in dichloromethane (60 mL) to give 3.94 g (94%) of the target compound as a slightly red powder.

mp 131.0–139.0° C.; $^1$H-NMR (300 MHz, DMSO-d$_6$) δ 8.84 (s, 1H), 8.42 (s, 1H), 8.27 (d, J=7.5 Hz, 1H), 7.52–7.11 (m, 15H), 5.19 (s, 2H), 4.39 (d, J=2.2 Hz, 2H), 4.25–4.21 (m, 1H), 4.21–4.00 (m, 1H), 2.96–2.92 (m, 1H), 2.74–2.69 (m, 1H), 0.89 (s, 9H), 0.08 (s, 6H); IR (KBr) 3330, 3190, 3050, 3000, 2950, 2920, 2880, 2850, 1730, 1720, 1715, 1695, 1680, 1665, 1650, 1640, 1635, 1605, 1560, 1540, 1535, 1520 cm$^{-1}$ (2) 2-(5-Amino-6-oxo-2-phenyl-1,6-dihydro-1-pyrimidyl)-N-[1-benzyl-2-(tert-butyldimethylsilyl)oxy-3,3,3-trifluoropropyl]acetamide was synthesized in the same manner as in Example 2. That is, the target compound in step (1) (3.50 g, 5.04 mmol) was treated under a hydrogen atmosphere in the presence of 10% palladium carbon (350 mg) in a mixed solution of ethanol (50 mL) and THF (15 mL) to give 2.22 g (79%) of the target compound as a pale-yellow solid.

mp 142–153° C.; $^1$H-NMR (300 MHz, DMSO-d$_6$) δ 8.21 (d, J=7.5 Hz, 1H), 7.46–7.12 (m, 11H), 5.11 (s, 2H), 4.26–4.21 (m, 1H), 4.13–4.08 (m, 1H), 2.94 (dd, J=14.8, 2.4 Hz, 2H), 2.71 (dd, J=14.8, 11.1 Hz, 2H), 0.89 (s, 9H), 0.10 (s, 3H), 0.09 (s, 3H); IR (KBr) 3420, 3290, 3050, 3020, 2950, 2920, 2890, 2850, 1720, 1700, 1680, 1675, 1665, 1660, 1640, 1605, 1575, 1540, 1535, 1520, 1505 cm$^{-1}$ (3) To an alkoxide solution prepared from sodium hydride (60% in oil, 1.60 g, 40.0 mmol) and allyl alcohol (100 mL) was added methyl 4-hydroxymethylbenzoate (3.32 g, 20.0 mmol) under ice-cooling. The resulting mixture was stirred at room temperature for 6 h, adjusted with 1N hydrochloric acid to pH 3, and then concentrated under reduced pressure. To the residue was added ethyl acetate (150 mL), and the mixture was washed successively with 1N hydrochloric acid, saturated aqueous sodium hydrogencarbonate solution and saturated brine, and dried over anhydrous magnesium sulfate. The solvent was evaporated under reduced pressure and the residue was separated and purified by silica gel column chromatography (hexane-ethyl acetate, 5:2) to give 3.59 g (93%) of allyl 4-hydroxymethylbenzoate as a pale-yellow oil.

$^1$H-NMR (300 MHz, CDCl$_3$) δ 8.05 (d, J=8.0 Hz, 2H), 7.43 (d, J=8.0 Hz, 2H), 6.11–5.97 (m, 1H), 5.45–5.37 (m, 1H), 5.31–5.27 (m, 1H), 4.83–4.80 (m, 2H), 4.76 (d, J=4.7 Hz, 2H); IR (neat) 3400, 3080, 2920, 2870, 1930, 1715, 1705, 1700, 1690, 1645, 1635, 1610, 1575, 1505 cm$^{-1}$ (4) To a solution of the target compound in step (2) (500 mg, 2.07 mmol) in dichloromethane (10 mL) were added triethylamine (2.30 mL, 0.892 mmol) and triphosgene (150 mg, 0.505 mmol) under ice-cooling. The resulting mixture was stirred for 30 min, and allyl 4-hydroxymethylbenzoate (1.04 g, 6.28 mmol) was added under ice-cooling. The resulting mixture was stirred at room temperature overnight. Ethyl acetate (120 mL) was added, and then the mixture was washed with saturated aqueous ammonium chloride solution and saturated brine, dried over anhydrous magnesium sulfate, and concentrated under reduced pressure. To a solution of the residue in THF (5 mL) was added a solution (1.0 M, 1.07 mL, 1.07 mmol) of tetrabutylammonium fluoride in THF. The resulting mixture was stirred at room temperature for 2 days. Ethyl acetate (150 mL) was added, and then the mixture was washed with water and saturated brine, dried over anhydrous magnesium sulfate, and concentrated under reduced pressure. The residue was separated and purified by silica gel column chromatography (dichloromethane-ethyl acetate, 9:1) to give a colorless solid, which was recrystallized from ethyl acetate-hexane (1:20) to give 453 mg (76%) of 2-[5-[4-(allyloxycarbonyl)-benzyloxycarbonyl]amino-6-oxo-2-phenyl-1,6-dihydro-1-pyrimidyl]-N-(1-benzyl-2-hydroxy-3,3,3-trifluoropropyl) acetamide as colorless crystals.

mp 126.0–135.0° C.; $^1$H-NMR (300 MHz, DMSO-d$_6$) δ 9.01 (s, 1H), 8.44 (s, 1H), 8.34 (d, J=8.6 Hz, 0.8H), 8.27 (d,

J=9.2 Hz, 0.2H), 8.01 (d, J=8.3 Hz, 2H), 7.60 (d, J=8.3 Hz, 2H), 7.55–7.09 (m, 10H), 6.79 (d, J=6.6 Hz, 0.2H), 6.72 (d, J=7.0 Hz, 0.8H), 6.12–5.99 (m, 1H), 5.45–5.42, 5.39–5.36 (m, 1H), 5.22–5.03 (m, 1H), 5.28 (s, 2H), 4.83–4.78 (m, 2H), 4.42 (d, J=16.5 Hz, 1H), 4.26 (d, J=16.5 Hz, 1H), 4.09–4.02 (m, 1H), 3.94–3.87 (m, 1H), 2.92 (dd, J=14.2, 2.8 Hz, 0.8H), 2.82 (dd, J=13.9, 7.2 Hz, 0.2H), 2.74 (dd, J=14.2, 10.2 Hz, 0.8H), 2.65 (dd, J=13.9, 7.9 Hz, 0.2H); IR (KBr) 3280, 3050, 3020, 2920, 1735, 1715, 1700, 1695, 1660, 1650, 1645, 1635, 1605, 1560, 1545, 1525, 1520, 1515, 1505 cm$^{-1}$ (5) To a solution of the target compound in step (4) (400 mg, 0.602 mmol) in dichloromethane (25 mL) was added Dess-Martin periodinane (510 mg, 1.20 mmol). The resulting mixture was stirred at room temperature overnight, and then diluted with ether (20 mL). Saturated aqueous sodium hydrogencarbonate solution (20 mL) containing sodium thiosulfate (25 g/100 mL) was added and the mixture was stirred at room temperature for 2 h. The organic layer was separated, washed with saturated aqueous sodium hydrogencarbonate solution and saturated brine, dried over anhydrous magnesium sulfate, and concentrated under reduced pressure. The residue was separated and purified by silica gel column chromatography (dichloromethane-ethyl acetate, 4:1) to give 287 mg (72%) of 2-[5-[4-(allyloxycarbonyl)-benzyloxycarbonyl]amino-6-oxo-2-phenyl-1,6-dihydro-1-pyrimidinyl]-N-(1-benzyl-3,3,3-trifluoro-2-oxopropyl) acetamide as a pale-brown oil.

$^1$H-NMR (500 MHz, DMSO-d$_6$+D$_2$O) δ 8.40 (s, 1H), 8.02 (d, J=8.2 Hz, 2H), 7.59 (d, J=8.2 Hz, 2H), 7.53 (t, J=7.4 Hz, 1H), 7.39 (t, J=7.9 Hz, 2H), 7.30 (d, J=7.3 Hz, 2H), 7.22–7.14 (m, 5H), 6.11–6.00 (m, 1H), 5.45–5.35 (m, 1H), 5.33–5.28 (m, 1H), 5.28 (s, 2H), 4.83–4.81 (m, 2H), 4.40 (d, J=16.4 Hz, 1H), 4.35 (d, J=16.4 Hz, 1H), 4.27 (dd, J=11.3, 2.2 Hz, 1H), 3.14 (dd, J=13.9, 2.2 Hz, 1H), 2.66 (dd, J=13.9, 11.3 Hz, 1H); IR (KBr) 3320, 3290, 3050, 2920, 1715, 1705, 1695, 1665, 1660, 1650, 1635, 1625, 1620, 1615, 1600, 1570, 1565, 1560, 1540, 1520, 1510 cm$^{-1}$ (6) To a solution of the target compound in step (5) (200 mg, 0.302 mmol) in dichloromethane (10 mL) were added triphenylphosphine (31.7 mg, 0.121 mmol) and tetrakis (triphenylphosphine)palladium (69.8 mg, 0.0604 mmol). After cooling on an ice bath, pyrrolidine (26.6 μL, 0.320 mmol) was added and the mixture was stirred for 2 h. The reaction mixture was diluted with ethyl acetate (20 mL), and then extracted with 15% aqueous sodium hydrogencarbonate solution. The aqueous layer was adjusted with 1N hydrochloric acid to pH 2 and extracted with dichloromethane. The extract was dried over anhydrous magnesium sulfate and concentrated under reduced pressure. The residue was separated and purified by silica gel column chromatography (dichloromethane-methanol, 19:1–9:1–4:1) to give a colorless oil. The oil was dissolved in ethyl acetate (100 mL), washed with water and dried over anhydrous magnesium sulfate. Concentration under reduced pressure to 2 mL followed by addition of hexane (20 mL) gave crystals, affording 62.6 mg (33%) of the title compound as a colorless powder.

mp 202.0–207.0° C.; $^1$H-NMR (500 MHz, DMSO-d$_6$+D$_2$O) δ 8.41 (s, 1H), 7.97 (d, J=8.3 Hz, 2H), 7.57 (d, J=8.3 Hz, 2H), 7.53 (t, J=7.5 Hz, 1H), 7.38 (t, J=7.9 Hz, 2H), 7.31 (d, J=7.3 Hz, 2H), 7.22–7.14 (m, 5H), 5.27 (s, 2H), 4.40 (d, J=16.3 Hz, 1H), 4.34 (d, J=16.3 Hz, 1H), 4.26 (dd, J=11.3, 2.2 Hz, 1H), 3.14 (dd, J=14.2, 2.2 Hz, 1H), 2.66 (dd, J=14.2, 11.3 Hz, 1H); IR (KBr) 3350, 3250, 3050, 3000, 2900, 2780, 2600, 2450, 2300, 1730, 1715, 1705, 1695, 1685, 1650, 1645, 1630, 1570, 1560, 1540, 1520, 1510, 1505 cm$^{-1}$ MS (SIMS, positive) m/z 641 (hydrate, MH$^+$), 623 (MH$^+$)

EXAMPLE 54

Synthesis of 2-[5-[3-(carboxy)benzyloxycarbonyl]amino-6-oxo-2-phenyl-1,6-dihydro-1-pyrimidyl]-N-(1-benzyl-3,3,3-trifluoro-2-oxopropyl)-acetamide.

(1) A mixture of dimethyl m-phthalate (40.0 g, 0.206 mol) and 1,1-dimethylhydrazine (78.3 mL, 1.03 mol) was stirred at room temperature for 17 h and refluxed under heating for 21 h. The reaction mixture was concentrated, and the residue was washed with dichloromethane to give a powder, to which were added water (300 mL) and 1N hydrochloric acid (300 mL). The precipitated solids were collected by filtration, dried under reduced pressure, and recrystallized from chloroformmethanol (9:1) to give 9.05 g (24%) of 3-methoxycarbonylbenzoic acid as colorless crystals.

mp 178.0–183.5° C.; $^1$H-NMR (200 MHz, CDCl$_3$) δ 8.78 (t, J=1.6 Hz, 1H), 8.30 (td, J=7.8, 1.6 Hz, 2H), 7.58 (d, J=7.8, 1H), 3.97 (s, 3H); IR (KBr) 3450, 3090, 3000, 2950, 2800, 2650, 2550, 2320, 1725, 1605, 1580 cm$^{-1}$ (2) To a suspension of 3-methoxycarbonybenzoic acid (4.00 g, 27.8 mmol) in THF (100 mL) was added borane-dimethylsulfide complex (10 M, 4.44 mL, 44.4 mmol) under ice-cooling. The resulting mixture was stirred at room temperature for 17 h. Water (50 mL) was added and the solvent was distilled under reduced pressure to 50 mL. The resulting suspension was extracted with ethyl acetate, and washed successively with saturated aqueous sodium hydrogencarbonate solution and saturated brine, and the organic layer was dried over anhydrous magnesium sulfate. The solvent was concentrated to give 3.50 g (95%) of a colorless oil. The oil was added to an alkoxide solution prepared from sodium hydride (60% in oil, 1.68 g, 42.1 mmol) and allyl alcohol (100 mL) under ice-cooling. The resulting mixture was stirred at room temperature for 17 h, adjusted with 1N hydrochloric acid to pH 3, and concentrated under reduced pressure. Ethyl acetate (200 mL) was added to the residue and the mixture was washed successively with saturated aqueous sodium hydrogencarbonate solution and saturated brine, and dried over anhydrous magnesium sulfate. The solvent was concentrated and the residue was separated and purified by silica gel column chromatography (hexane-ethyl acetate, 5:2) to give 2.89 g (71%) of allyl 3-hydroxymethylbezoate as a colorless oil.

$^1$H-NMR (300 MHz, CDCl$_3$) δ 8.06 (s, 1H), 7.99 (d, J=7.7 Hz, 1H), 7.58 (d, J=7.5 Hz, 1H), 7.45 (t, J=7.7 Hz, 1H), 6.09–6.00 (m, 1H), 5.45–5.37 (m, 1H), 5.32–5.27 (m, 1H), 4.85–4.81 (m, 2H), 4.76 (d, J=5.7 Hz, 2H); IR (neat) 3400, 3080, 3000, 2930, 2880, 1715, 1705, 1695, 1680, 1665, 1660, 1645, 1635, 1610, 1585, 1575 cm$^{-1}$ (3) 2-[5-[3-(Allyloxycarbonyl)benzyloxycarbonyl]amino-6-oxo-2-phenyl-1,6-dihydro-1-pyrimidyl]-N-(1-benzyl-2-hydroxy-3,3,3-trifluoro-propyl)acetamide was synthesized in the same manner as in Example 53. That is, the target compound in Example 53-(2) (500 mg, 2.07 mmol) was reacted with triethylamine (2.30 mL, 0.892 mmol), triphosgene (150 mg, 0.505 mmol) and allyl 3-hydroxymethylbenzoate (1.04 g, 6.28 mmol) in dichloromethane (10 mL) to give an oil. The obtained oil was treated with a solution (1.0 M, 1.07 mL, 1.07 mmol) of tetrabutylammonium fluoride in THF to afford 465 mg (78%) of the target compound as colorless crystals.

mp 192.0–195.0° C.; $^1$H-NMR (300 MHz, DMSO-$d_6$) δ 9.02 (s, 1H), 8.43 (s, 1H), 8.34 (d, J=8.6 Hz, 0.8H), 8.27 (d, J=9.1 Hz, 0.2H), 8.06 (s, 1H), 7.91 (d, J=7.8 Hz, 1H), 7.75 (d, J=7.8 Hz, 1H), 7.57 (d, J=7.8 Hz, 1H), 7.58–7.28 (m, 10H), 6.79 (d, J=6.6 Hz, 0.2H), 6.72 (d, J=7.0 Hz, 0.2H), 6.13–5.99 (m, 1H), 5.45–5.37 (m, 1H), 5.31–5.23 (m, 1H), 5.27 (s, 2H), 4.84–4.81 (m, 2H), 4.42 (d, J=16.5 Hz, 1H), 4.25 (d, J=16.5 Hz, 1H), 4.11–4.01 (m, 1H), 3.94–3.86 (m, 1H), 2.92 (dd, J=14.2, 2.8 Hz, 0.8H), 2.82 (dd, J=13.9, 7.2 Hz, 0.2H), 2.74 (dd, J=14.2, 10.2 Hz, 0.8H), 2.65 (dd, J=13.9, 7.9 Hz, 0.2H); IR (KBr) 3420, 3370, 3320, 3250, 3080, 3050, 3005, 2920, 1730, 1720, 1705, 1690, 1675, 1660–1645, 1640, 1635, 1620, 1600, 1595, 1585, 1575, 1560, 1540, 1520–1505 cm$^{-1}$ (4) 2-[5-[3-(Allyloxycarbonyl)benzyloxycarbonyl]amino-6-oxo-2-phenyl-1,6-dihydro-1-pyrimidyl]-N-(1-benzyl-3,3,3-trifluoro-2-oxopropyl)-acetamide was synthesized in the same manner as in Example 53. That is, the target compound in step (3) (400 mg, 0.602 mmol) was treated with Dess-Martin periodinane (510 mg, 1.20 mmol) in dichloromethane (25 mL) to give 329 mg (82%) of the target compound as a pale-brown oil.

$^1$H-NMR (500 MHz, DMSO-$d_6$+$D_2O$) δ 8.40 (s, 1H), 8.05 (s, 1H), 7.99–7.96 (m, 1H), 7.75–7.7. (m, 1H), 7.59 (t, J=7.7 Hz, 1H), 7.55–7.51 (m, 1H), 7.38 (t, J=8.0 Hz, 2H), 7.32–7.29 (m, 2H), 7.21–7.14 (m, 5H), 6.17–6.10 (m, 1H), 5.43–5.38 (m, 1H), 5.32–5.28 (m, 1H), 5.27 (s, 2H), 4.84–4.81 (m, 2H), 4.40 (d, J=16.5 Hz, 1H), 4.34 (d, J=16.5 Hz, 1H), 4.26 (dd, J=11.5, 2.5 Hz, 1H), 3.13 (dd, J=14.2, 2.5 Hz, 1H), 2.66 (dd, J=14.2, 11.5 Hz, 1H); IR (KBr) 3280, 3050, 3010, 2920, 1720–1695, 1670, 1660, 1650–1640, 1630, 1615, 1600, 1565, 1560, 1540, 1525, 1505 cm$^{-1}$ (5) 2-[5-[3-(Carboxy)benzyloxycarbonyl]amino-6-oxo-2-phenyl-1,6-dihydro-1-pyrimidyl]-N-(1-benzyl-3,3,3-trifluoro-2-oxopropyl)acetamide was synthesized in the same manner as in Example 53. That is, the target compound in step (4) (200 mg, 0.302 mmol) was reacted with triphenylphosphine (31.7 mg, 0.121 mmol), tetrakis(triphenylphosphine)palladium (69.8 mg, 0.0604 mmol) and pyrrolidine (26.6 μL, 0.320 mmol) in dichloromethane (10 mL) to give 64.2 mg (34%) of the title compound as a colorless powder.

mp 213.0–215.0° C.; $^1$H-NMR (500 MHz, DMSO-$d_6$+$D_2O$) δ 8.40 (s, 1H), 8.01 (s, 1H), 7.93 (d, J=7.7 Hz, 1H), 7.70 (d, J=7.7 Hz, 1H), 7.56 (t, J=7.7 Hz, 1H), 7.52 (d, J=7.7 Hz, 1H), 7.38 (t, J=7.9 Hz, 2H), 7.30 (d, J=7.6 Hz, 2H), 7.21–7.14 (m, 5H), 5.26 (s, 2H), 4.39 (d, J=16.3 Hz, 1H), 4.34 (d, J=16.3 Hz, 1H), 4.25 (dd, J=11.3, 1.9 Hz, 1H), 3.13 (dd, J=13.4, 1.9 Hz, 1H), 2.60 (dd, J=13.4, 11.3 Hz, 1H); IR (KBr) 3380, 3250, 3050, 2900, 1735, 1720, 1705, 1690, 1650, 1640, 1635, 1620, 1605, 1565, 1560, 1535, 1520, 1515, 1505 cm$^{-1}$ MS (SIMS, positive) m/z 641 (hydrate, MH$^+$), 623 (MH$^+$)

EXAMPLE 55

Synthesis of 2-(5-isopropyloxycarbonylamino-6-oxo-2-phenyl-1,6-dihydro-1-pyrimidyl)-N-(1-benzyl-3,3,3-trifluoro- 2-oxopropyl)-acetamide.

To a solution of the title compound in Example 2 (200 mg, 0.452 mmol) in THF (10 mL) were added sodium carbonate (128 mg, 1.21 mmol) and isopropyl chlorocarbonate (68.8 μL, 0.605 mmol). The resulting mixture was stirred at room temperature for 17 h. Ethyl acetate (70 mL) was added and the mixture was washed with saturated aqueous ammonium chloride solution and saturated brine, dried over anhydrous magnesium sulfate, and concentrated under reduced pressure. The residue was separated and purified by silica gel column chromatography (chloroform-methanol, 19:1) to give 167 mg (66%) of the title compound as colorless crystals.

mp 170.0–172.0° C. (decomposition); $^1$H-NMR (500 MHz, DMSO-$d_6$+$D_2O$) δ 8.38 (s, 1H), 7.53 (t, J=7.5 Hz, 1H), 7.38 (t, J=7.9 Hz, 2H), 7.30 (d, J=7.3 Hz, 2H), 7.23–7.13 (m, 5H), 4.89 (m, 1H), 4.39 (d, J=16.1 Hz, 1H), 4.33 (d, J=16.1 Hz, 1H), 4.25 (dd, J=11.3, 2.0 Hz, 1H), 3.13 (dd, J=14.1, 2.0 Hz, 1H), 2.60 (dd, J=14.1, 11.3 Hz, 1H), 1.26 (d, J=6.3 Hz, 6H); IR (KBr) 3420, 3370, 3260, 3050, 3010, 2980, 2920, 2880, 1720–1700, 1695, 1685, 1680, 1675, 1670, 1660, 1655–1640, 1635, 1620, 1600, 1575, 1565, 1560, 1545, 1530, 1520, 1505 cm$^{-1}$

EXAMPLE 56

Synthesis of 2-(5-methoxyoxalylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (600 mg, 1.36 mmol) was reacted with sodium carbonate (400 mg, 3.77 mmol) and methyloxalyl chloride (167 μL, 1.76 mmol) in THF (30 mL) to give 467 mg (65%) of the title compound as pale-yellow crystals.

mp 210.0–211.0° C.; $^1$H-NMR (500 MHz, DMSO-$d_6$) δ 9.66 (s, 1H), 8.73 (s, 1H), 8.19 (d, J=9.8 Hz, 1H), 7.52 (m, 1H), 7.39–7.32 (m, 4H), 7.21–7.14 (m, 5H), 7.13 (s, 1H), 7.11 (s, 1H), 4.41 (d, J=16.3 Hz, 1H), 4.33 (d, J=16.3 Hz, 1H), 4.26 (m, 1H), 3.86 (s, 3H), 3.13 (dd, J=14.2, 2.4 Hz, 1H), 2.60 (dd, J=14.2, 11.4 Hz, 1H); IR (KBr) 3450, 3300, 3050, 2950, 2850, 1760, 1735, 1715, 1705, 1695, 1690, 1675, 1670, 1650, 1620, 1600, 1560, 1545, 1520, 1505 cm$^{-1}$ MS (CI, positive) m/z 531 (MH$^+$)

EXAMPLE 57

Synthesis of 2-(5-methoxymalonylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (600 mg, 1.36 mmol) was reacted with sodium carbonate (400 mg, 3.77 mmol) and methylmalonyl chloride (189 μL, 1.76 mmol) in THF (30 mL) to give 293 mg (40%) of the title compound as pale-yellow crystals.

mp 76.5–77.50° C.; $^1$H-NMR (500 MHz, DMSO-$d_6$) δ 9.84 (s, 1H), 8.80 (s, 1H), 8.15 (d, J=9.8 Hz, 1H), 7.50 (m, 1H), 7.35 (t, J=7.5 Hz, 2H), 7.30 (d, J=7.2 Hz, 2H), 7.21–7.14 (m, 5H), 7.12 (s, 1H), 7.11 (s, 1H), 4.43 (d, J=16.2 Hz, 1H), 4.32–4.23 (m, 2H), 3.70 (s, 2H), 3.66 (s, 3H), 3.13 (dd, J=14.2, 2.3 Hz, 1H), 2.60 (dd, J=14.2, 11.4 Hz, 1H); IR (KBr) 3280, 3050, 3020, 2950, 1730, 1720, 1700, 1680, 1670, 1650, 1615, 1605, 1580, 1560, 1545, 1520, 1505 cm$^{-1}$ MS (CI, positive) m/z 545 (MH$^+$)

EXAMPLE 58

Synthesis of 2-(5-methoxysuccinylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (600 mg, 1.36 mmol) was reacted with sodium carbonate (400 mg, 3.77 mmol) and methylsuccinyl chloride (217 μL, 1.76 mmol) in THF (30 mL) to give 576 mg (76%) of the title compound as colorless crystals.

mp 78.5–79.5° C.; $^1$H-NMR (500 MHz, DMSO-$d_6$) δ 9.52 (s, 1H), 8.75 (s, 1H), 8.15 (d, J=9.7 Hz, 1H), 7.49 (m, 1H), 7.34 (t, J=7.8 Hz, 2H), 7.29 (d, J=7.3 Hz, 2H), 7.21–7.14 (m, 5H), 7.12 (s, 1H), 7.11 (s, 1H), 4.42 (d, J=16.1 Hz, 1H), 4.31–4.24 (m, 2H), 3.59 (s, 3H), 3.14–3.11 (m, 1H), 2.77 (t, J=5.6 Hz, 2H), 2.62–2.56 (m, 3H); IR (KBr) 3300, 3050, 3020, 2950, 1730, 1720, 1700, 1690, 1650, 1605, 1560, 1550, 1520, 1505 cm$^{-1}$ MS (CI, positive) m/z 559 (MH$^+$), 527

EXAMPLE 59
Synthesis of 2-(5-methoxyglutarylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (900 mg, 2.03 mmol) was reacted with sodium carbonate (600 mg, 5.66 mmol) and methylglutaryl chloride (364 μL, 2.63 mmol) to give 762 mg (66%) of the title compound as a colorless solid.

mp 74.5–75.5° C.; $^1$H-NMR (500 MHz, DMSO-$d_6$) δ 9.39 (s, 1H), 8.77 (s, 1H), 8.14 (d, J=9.7 Hz, 1H), 7.50 (m, 1H), 7.35 (d, J=8.0 Hz, 2H), 7.30 (m, 2H), 7.21–7.14 (m, 5H), 7.11 (s, 1H), 7.10 (s, 1H), 4.41 (d, J=16.6 Hz, 1H), 4.33 (d, J=16.6 Hz, 1H), 4.26 (m, 1H), 3.60 (s, 3H), 3.13 (dd, J=14.2, 2.4 Hz, 1H), 2.60 (dd, J=14.2, 11.3 Hz, 1H), 2.52–2.49 (m, 2H), 2.35 (t, J=6.0 Hz, 2H), 1.81 (m, 2H); IR (KBr) 3290, 3050, 3010, 2930, 1720, 1650, 1600, 1560, 1540, 1535, 1520, 1505 cm$^{-1}$ MS (CI, positive) m/z 573 (MH$^+$)

EXAMPLE 60
Synthesis of 2-(5-hydroxyoxalylamino-6-oxo-2-phenyl-1,6-dihydro-1-pyrimidyl)-N-(1-benzyl-3,3,3-trifluoro-2-oxopropyl)acetamide.

To a solution of the title compound in Example 56 (350 mg, 0.660 mmol) in THF (20 mL) was added 0.1N aqueous sodium hydroxide solution (6.60 mL). The resulting mixture was stirred at room temperature for 2 h. 1N Hydrochloric acid (0.726 mL) was added and the mixture was concentrated under reduced pressure. The resulting suspension was extracted with ethyl acetate. The extract was washed with saturated brine and the organic layer was dried over anhydrous magnesium sulfate. The solvent was evaporated under reduced pressure. Recrystallization from ethyl acetate-hexane (1:5) gave 313 mg (92%) of the title compound as pale-yellow crystals.

mp 193.0–195.0° C.; $^1$H-NMR (500 MHz, DMSO-$d_6$) δ 9.54 (s, 1H), 8.76 (s, 1H), 8.19 (d, J=9.8 Hz, 1H), 7.52 (m, 1H), 7.39–7.32 (m, 4H), 7.20–7.14 (m, 5H), 7.13 (s, 1H), 7.11 (s, 1H), 4.40 (d, J=16.4 Hz, 1H), 4.34 (d, J=16.4 Hz, 1H), 4.25 (m, 1H), 3.13 (dd, J=14.2, 2.4 Hz, 1H), 2.60 (dd, J=14.2, 11.4 Hz, 1H); IR (KBr) 3400, 3350, 3300, 3050, 3020, 2920, 1730, 1720, 1650, 1620, 1605, 1575, 1560, 1550, 1520, 1505 cm$^{-1}$ MS (CI, positive) m/z 517 (MH$^+$), 499, 473

EXAMPLE 61
Synthesis of 2-(5-hydroxymalonylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 60. That is, the title compound in Example 57 (280 mg, 0.514 mmol) was reacted with 0.1N aqueous sodium hydroxide solution (5.14 mL) in THF (15 mL) to give 251 mg (92%) of the title compound as pale-yellow crystals.

mp 126.0–128.0° C.; $^1$H-NMR (500 MHz, DMSO-$d_6$) δ 13–12 (bs, 1H), 9.81 (s, 1H), 8.81 (s, 1H), 8.15 (d, J=9.8 Hz, 1H), 7.50 (m, 1H), 7.35 (t, J=8.0 Hz, 2H), 7.31 (d, J=7.1 Hz, 2H), 7.20–7.14 (m, 5H), 7.11 (s, 1H), 7.10 (s, 1H), 4.42 (d, J=16.2 Hz, 1H), 4.31 (d, J=16.2 Hz, 1H), 4.26 (m, 1H), 3.57 (s, 1H), 3.13 (dd, J=14.3, 2.3 Hz, 1H), 2.60 (dd, J=14.3, 11.4 Hz, 1H); IR (KBr) 3300, 3050, 3020, 2950, 2920, 1720, 1705, 1700, 1695, 1685, 1670, 1665, 1650, 1635, 1615, 1600, 1580, 1560, 1545, 1520, 1505 cm$^{-1}$

EXAMPLE 62
Synthesis of 2-(5-hydroxysuccinylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 60. That is, the title compound in Example 58 (360 mg, 0.645 mmol) was treated with 0.1N aqueous sodium hydroxide solution (6.45 mL) in THF (15 mL) to give 311 mg (88%) of the title compound as colorless crystals.

mp 100.0–101.0° C.; $^1$H-NMR (500 MHz, DMSO-$d_6$) δ 13–11.5 (bs, 1H), 9.46 (s, 1H), 8.76 (s, 1H), 8.14 (d, J=9.7 Hz, 1H), 7.49 (m, 1H), 7.35 (t, J=8.0 Hz, 2H), 7.29 (d, J=7.1 Hz, 2H), 7.21–7.14 (m, 5H), 7.13 (s, 1H), 7.11 (s, 1H), 4.42 (d, J=16.0 Hz, 1H), 4.30 (d, J=16.0 Hz, 1H), 4.26 (m, 1H), 3.13 (dd, J=14.1, 2.2 Hz, 1H), 2.71 (t, J=7.2 Hz, 2H), 2.60 (dd, J=14.1, 11.4 Hz, 1H), 2.51–2.48 (m, 2H); IR (KBr) 3250, 3050, 2920, 1730, 1720, 1700, 1690, 1680, 1670, 1660, 1645, 1600, 1560, 1540, 1535, 1515 cm$^{-1}$ MS (CI, positive) m/z 545 (MH$^+$), 527

EXAMPLE 63
Synthesis of 2-(5-benzoylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (300 mg, 0.678 mmol) was reacted with sodium carbonate (200 mg, 1.89 mmol) and benzoyl chloride (106 μL, 0.908 mmol) in THF (15 mL) to give 271 mg (73%) of the title compound as colorless crystals.

mp 225.0–227.0° C.; $^1$H-NMR (300 MHz, DMSO-$d_6$) δ 9.42 (s, 1H), 8.75 (s, 1H), 8.21 (d, J=9.7 Hz, 1H), 7.96 (m, 2H), 7.67–7.49 (m, 4H), 7.38–7.36 (m, 4H), 7.23–7.18 (m, 5H), 7.16 (s, 1H), 7.14 (s, 1H), 4.44 (d, J=16.6 Hz, 1H), 4.35 (d, J=16.6 Hz, 1H), 4.27 (m, 1H), 3.14 (dd, J=14.1, 2.1 Hz, 1H), 2.61 (dd, J=14.1, 11.4 Hz, 1H); IR (KBr) 3380, 3300, 3050, 3020, 2950, 2920, 1740, 1700, 1680, 1650, 1630, 1595, 1580, 1560, 1550, 1540, 1525, 1515 cm$^{-1}$ MS (CI, positive) m/z 549 (MH$^+$)

EXAMPLE 64
Synthesis of 2-(6-oxo-2-phenyl-5-phenylacetylamino-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2

(300 mg, 0.678 mmol) was reacted with sodium carbonate (200 mg, 1.89 mmol) and phenylacetyl chloride (120 μL, 0.908 mmol) in THF (30 mL) to give 188 mg (50%) of the title compound as colorless crystals.

pmp 210.0–211.0° C.; $^1$H-NMR (500 MHz, DMSO-d$_6$) δ 9.56 (s, 1H), 8.77 (s, 1H), 8.18 (d, J=9.5 Hz, 1H), 7.53–7.12 (m, 17H), 4.41 (d, J=16.5 Hz, 1H), 4.32 (d, J=16.5 Hz, 1H), 4.25 (m, 1H), 3.84 (s, 2H), 3.13 (dd, J=14.2, 2.2 Hz, 1H), 2.60 (dd, J=14.2, 11.3 Hz, 1H); IR (KBr) 3450, 3350, 3280, 3050, 3020, 2950, 2920, 1760, 1700, 1685, 1675, 1650, 1600, 1560, 1550, 1535, 1520, 1505 cm$^{-1}$ MS (CI, positive) m/z 563 (MH$^+$)

EXAMPLE 65

Synthesis of 2-(5-cinnamoylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 55. That is, the title compound in Example 2 (300 mg, 0.678 mmol) was treated with sodium carbonate (200 mg, 1.89 mmol) and cinnamoyl chloride (151 mg, 0.908 mmol) in THF (30 mL) to give 176 mg (45%) of the title compound as pale-yellow crystals.

mp 238.0–240.0° C.; $^1$H-NMR (500 MHz, DMSO-d$_6$) δ 9.66 (s, 1H), 8.97 (s, 1H), 8.18 (d, J=9.8 Hz, 1H), 7.65 (m, 2H), 7.59 (d, J=15.7 Hz, 1H), 7.52 (m, 1H), 7.48–7.40 (m, 3H), 7.40–7.34 (m, 3H), 7.34–30 (m, 2H), 7.23–7.15 (m, 5H), 4.47 (d, J=16.3 Hz, 1H), 4.34 (d, J=16.3 Hz, 1H), 4.29 (m, 1H), 3.15 (dd, J=14.1, 2.2 Hz, 1H), 2.62 (dd, J=14.1, 11.5 Hz, 1H); IR (KBr) 3300, 3050, 3020, 1760, 1720, 1705, 1700, 1680, 1675, 1670, 1655, 1645, 1620, 1600, 1575, 1560, 1540, 1520, 1510 cm$^{-1}$ MS (CI, positive) m/z 575 (MH$^+$)

EXAMPLE 66

Synthesis of 2-(5-benzenesulfonylamino-6-oxo-2-phenyl-1,6-dihydro- 1-pyrimidyl)-N-(1-benzyl-3,3,3-trifluoro-2-oxopropyl)acetamide.

To a solution of the title compound in Example 2 (400 mg, 0.900 mmol) in THF (30 mL) were added pyridine (362 μL, 4.50 mmol) and benzenesulfonyl chloride (138 μL, 1.08 mmol) under ice-cooling. The resulting mixture was stirred at room temperature for 7 h. Benzenesulfonyl chloride (69.0 μL, 0.540 mmol) was added and the resulting mixture was stirred at room temperature for 17 h. Benzenesulfonyl chloride (69.0 μL, 0.540 mmol) was further added, and the mixture was stirred at room temperature for 8 h. Ethyl acetate (70 mL) was added and the mixture was washed with saturated aqueous potassium dihydrogenphosphate solution and saturated brine, and dried over anhydrous magnesium sulfate. The solvent was concentrated and the residue was separated and purified by silica gel column chromatography (dichloromethane-ethyl acetate, 4:3) to give a colorless oil, which was crystallized from ethyl acetate-hexane (1:20) to afford 396 mg (75%) of the title compound as a colorless powder.

mp 92.0–94.0° C.; $^1$H-NMR (300 MHz, DMSO-d$_6$) δ 10.05 (s, 1H), 8.13 (d, J=9.7 Hz, 1H), 7.94–7.90 (m, 2H), 7.87 (s, 1H), 7.68–7.54 (m, 3H), 7.51–7.46 (m, 1H), 7.42–7.23 (m, 4H), 7.20–7.12 (m, 5H), 7.11 (s, 1H), 7.10 (s, 1H), 4.35–4.19 (m, 3H), 3.12 (dd, J=14.0, 2.2 Hz, 1H), 2.57 (dd, J=14.0, 11.4 Hz, 1H); IR (KBr) 3300, 3200, 3050, 1760, 1720, 1700, 1680, 1675, 1670, 1650, 1630, 1620, 1600, 1595, 1585, 1560, 1540, 1530, 1520, 1505 cm$^{-1}$ MS (CI, positive) m/z 585 (MH$^+$)

EXAMPLE 67

Synthesis of 2-[6-oxo-2-phenyl-5-(p-toluenesulfonyl)amino-1,6-dihydro-1-pyrimidyl]-N-(1-benzyl-3,3,3-trifluoro-2-oxopropyl)acetamide.

The title compound was synthesized in the same manner as in Example 66. That is, the title compound in Example 2 (400 mg, 0.900 mmol) was reacted with pyridine (362 μL, 4.50 mmol) and p-toluenesulfonyl chloride (412 mg, 2.16 mmol) in THF (30 mL) to give 399 mg (74%) of the title compound as a colorless powder.

mp 91.0–93.0° C.; $^1$H-NMR (300 MHz, DMSO-d$_6$) δ 9.94 (s, 1H), 8.13 (d, J=9.7 Hz, 1H), 7.86 (s, 1H), 7.81 (d, J=8.2 Hz, 2H), 7.48 (m, 1H), 7.37 (d, J=8.2 Hz, 2H), 7.32 (m, 2H), 7.24 (m, 2H), 7.17–7.12 (m, 5H), 7.11 (s, 1H), 7.10 (s, 1H), 4.35–4.18 (m, 3H), 3.11 (dd, J=13.9, 1.6 Hz, 1H), 2.58 (dd, J=13.9, 11.4 Hz, 1H); IR (KBr) 3500, 3300, 3200, 3050, 3020, 2950, 2920, 1760, 1720, 1700, 1685, 1650, 1635, 1625, 1605, 1595, 1580, 1560, 1545, 1535, 1520, 1510 cm$^{-1}$ MS (CI, positive) m/z 599 (MH$^+$)

EXAMPLE 68

Synthesis of 2-(5-methanesulfonylamino-6-oxo-2-phenyl-1,6-dihydro-1-pyrimidyl)-N-(1-benzyl-3,3,3-trifluoro-2-oxopropyl)acetamide.

The title compound was synthesized in the same manner as in Example 66. That is, the title compound in Example 2 (400 mg, 0.900 mmol) was reacted with pyridine (362 μL, 4.50 mmol) and methanesulfonyl chloride (140 μL, 1.80 mmol) in THF (30 mL) to give 307 mg (65%) of the title compound as a colorless powder.

mp 93.0–96.0° C.; $^1$H-NMR (300 MHz, DMSO-d$_6$) δ 9.27 (s, 1H), 8.19 (d, J=9.8 Hz, 1H), 7.95 (s, 1H), 7.54 (m, 1H), 7.40 (m, 2H), 7.33 (m, 2H), 7.24–7.15 (m, 5H), 7.13 (s, 1H), 7.10 (s, 1H), 4.37 (s, 2H), 4.28 (m, 1H), 3.14 (dd, J=14.2, 2.0 Hz, 1H), 3.06 (s, 3H), 2.61 (dd, J=14.2, 11.6 Hz, 1H); IR (KBr) 3300, 3200, 3050, 3020, 2920, 1760, 1720, 1700, 1680, 1655, 1635, 1620, 1600, 1560, 1545, 1530, 1520, 1505 cm$^{-1}$ MS (CI, positive) m/z 523 (MH$^+$), 306

EXAMPLE 69

Synthesis of 2-[5-[4-(carboxy)phenylsulfonyl]amino-6-oxo-2-phenyl-1,6-dihydro-1-pyrimidyl]-N-(1-benzyl-3,3,3-trifluoro-2-oxopropyl)acetamide.

To a solution of the title compound in Example 2 (400 mg, 0.900 mmol) in THF (30 mL) were added pyridine (362 μL, 4.50 mmol) and 4-(chlorosulfonyl)benzoic acid (298 mg, 1.35 mmol) under ice-cooling. The resulting mixture was stirred at room temperature for 16 h. Saturated aqueous potassium dihydrogenphosphate solution (20 mL) and ethyl acetate (30 mL) were added. The aqueous layer was separated and extracted with ethyl acetate. The organic layers were combined, washed with saturated brine, and dried over anhydrous magnesium sulfate. The solvent was evaporated and the residue was applied to reversed phase (ODS) column chromatography (methanol-water, 55:45). The eluate was concentrated to 100 mL under reduced pressure, and then lyophilized to give a colorless oil, which was separated and purified by reversed phase (ODS) high performance liquid chromatography (acetonitrile-water, 50:50–80:20) to afford 43 mg (7.6%) of the title compound as a colorless powder and 57 mg (9.9%) of 2-[5-[4-(methoxycarbonyl) phenylsulfonyl]amino-6-oxo-2-phenyl-1,6-dihydro-1-pyrimidyl]-N-(1-benzyl-3,3,3-trifluoro-2-oxopropyl) acetamide as a colorless powder.

Title compound mp 127.0–130.0° C.; $^1$H-NMR (500 MHz, DMSO-d$_6$) δ 14–12.5 (bs, 1H), 10.22 (s, 1H), 8.09 (m, 3H), 8.01 (d, J=6.8 Hz, 2H), 7.91 (s, 1H), 7.49 (m, 1H), 7.33 (t, J=7.5 Hz, 2H), 7.29 (m, 2H), 7.15–7.10 (m, 7H), 4.31–4.19 (m, 3H), 3.10 (dd, J=14.1, 2.3 Hz, 1H), 2.57 (dd, J=14.1, 11.1 Hz, 1H); IR (KBr) 3350, 3320, 3180, 3030, 2600, 2450, 2300, 1730, 1710, 1700, 1695, 1690, 1680, 1675, 1650, 1640, 1630, 1620, 1600, 1570, 1560, 1540, 1525, 1515, 1500 cm$^{-1}$ MS (CI, positive) m/z 647 (MH$^+$)

2-[5-[4-(Methoxyoarbonyl)phenylsulfonyl]amino-6-oxo-2-phenyl-1,6-dihydro-1-pyrimidyl]-N-(1-benzyl-3,3,3-trifluoro-2-oxopropyl)-acetamide mp 195.0–210.0° C.; $^1$H-NMR (500 MHz, DMSO-d$_6$) δ 10.24 (s, 1H), 8.10 (m, 3H), 8.01 (m, 2H), 7.92 (s, 1H), 7.50 (m, 1H), 7.34 (m, 2H), 7.28 (m, 2H), 7.16–7.06 (m, 7H), 4.29 (d, J=16.4 Hz, 1H), 4.20 (d, J=16.4 Hz, 1H), 4.19 (m, 1H), 3.88 (s, 3H), 3.10 (dd, J=14.2, 2.3 Hz, 1H), 2.57 (dd, J=14.2, 11.3 Hz, 1H); IR (KBr) 3280, 3200, 3050, 2950, 1715, 1680, 1670, 1660, 1650, 1640, 1630, 1620, 1600, 1580, 1560, 1540, 1530, 1520, 1515, 1500 cm$^{-1}$ MS (CI, positive) m/z 661 (MH$^+$)

EXAMPLE 70

Synthesis of 2-[3-[4-(methoxycarbonyl)benzyloxycarbonyl] amino-2-oxo-6-phenyl-1,2-dihydro-1-pyridyl]-N-(1-benzyl-3,3,3-trifluoro-2-oxopropyl)acetamide.

(1) 2-(3-Amino-2-oxo-6-phenyl-1,2-dihydro-1-pyridyl)-N-[1-benzyl-2-(tert-butyldimethylsilyl)oxy-3,3,3-trifluoropropyl]acetamide was synthesized in the same manner as in Example 2. That is, the target compound in Example 13-(1) (10.6 g, 15.3 mmol) was reacted under a hydrogen atmosphere in the presence of 10% palladium carbon (2.00 g) in THF (70 mL) to give 6.97 g (81%) of the target compound as a colorless solid.

$^1$H-NMR (500 MHz, DMSO-d$_6$) δ 8.12 (d, J=7.4 Hz, 1H), 7.38 (t, J=7.3 Hz, 1H), 7.31 (t, J=7.3 Hz, 1H), 7.28–7.18 (m, 5H), 7.15 (d, J=6.9 Hz, 2H), 6.50 (d, J=7.4 Hz, 1H), 5.94 (d, J=7.4 Hz, 1H), 5.13 (s, 2H), 4.36–4.20 (m, 3H), 4.08 (m, 1H), 2.92 (dd, J=14.9, 2.3 Hz, 1H), 2.72 (dd, J=14.9, 11.1 Hz, 1H), 0.90 (s, 9H), 0.10 (s, 3H), 0.09 (s, 3H); IR (KBr) 3380, 3040, 2900, 2830, 1680, 1635, 1590, 1530 cm$^{-1}$ (2) 2-[3-[4-(Methoxycarbonyl)benzyloxycarbonyl] amino-2-oxo-6-phenyl-1,2-dihydro-1-pyridyl]-N-[1-benzyl-2-(tert-butyldimethylsilyl)oxy-3,3,3-trifluoropropyl] acetamide was synthesized in the same manner as in Example 53. That is, the target compound in step (1) (500 mg, 0.893 mmol) was reacted with triethylamine (1.00 mL, 7.20 mmol), triphosgene (150 mg, 0.505 mmol) and methyl 4-hydroxymethylbenzoate (450 mg, 2.71 mmol) in dichloromethane (10 mL) to give 548 mg (81%) of the target compound as pale-yellow crystals.

mp 79–80° C.; $^1$H-NMR (500 MHz, DMSO-d$_6$) δ 8.59 (s, 1H), 8.19 (d, J=7.4 Hz, 1H), 7.98 (d, J=8.4 Hz, 2H), 7.88 (d, J=7.6 Hz, 1H), 7.59 (t, J=8.4 Hz, 2H), 7.46 (t, J=7.5 Hz, 1H), 7.37 (t, J=7.5 Hz, 2H), 7.31–7.18 (m, 5H), 7.14 (d, J=6.8 Hz, 2H), 6.18 (d, J=7.6 Hz, 1H), 5.28 (s, 2H), 4.36 (d, J=16.4 Hz, 1H), 4.33 (d, J=16.4 Hz, 1H), 4.22 (m, 1H), 4.07 (m, 1H), 3.86 (s, 3H), 2.92 (dd, J=14.9, 2.3 Hz, 1H), 2.70 (dd, J=14.9, 11.2 Hz, 1H), 0.90 (s, 9H), 0.08 (s, 6H); IR (KBr) 3450, 3350, 3280, 3050, 3000, 2950, 2930, 2880, 2840, 1735, 1720, 1680, 1650, 1645, 1640, 1625, 1560, 1540, 1520, 1510 cm$^{-1}$ (3) 2-[3-[4-(Methoxycarbonyl)benzyloxycarbonyl] amino-2-oxo-6-phenyl-1,2-dihydro-1-pyridyl]-N-(1-benzyl-2-hydroxy-3,3,3-trifluoropropyl) acetamide was synthesized in the same manner as in Example 53. That is, the target compound in step (2) (450 mg, 0.598 mmol) was treated with a THF solution (1.0 M, 0.718 mL, 0.718 mmol) of tetrabutylammonium fluoride in THF (5 mL) to give 340 mg (89%) of the target compound as pale-yellow crystals.

mp 217.0–218.0° C.; $^1$H-NMR (500 MHz, DMSO-d$_6$) δ 8.60 (s, 1H), 8.23 (d, J=8.6 Hz, 1H), 7.98 (d, J=8.4 Hz, 2H), 7.89 (d, J=7.7 Hz, 1H), 7.59 (d, J=7.8 Hz, 1H), 7.46 (d, J=7.8 Hz, 1H), 7.37 (t, J=7.8 Hz, 2H), 7.28 (d, J=7.8 Hz, 2H), 7.24–7.17 (m, 3H), 7.11 (dd, J=1.9, 7.9 Hz, 2H), 6.69 (d, J=7.0 Hz, 1H), 6.17 (d, J=7.7 Hz, 1H), 5.28 (s, 2H), 4.39 (d, J=16.2 Hz, 1H), 4.22 (d, J=16.2 Hz, 1H), 4.07 (m, 1H), 3.92 (m, 1H), 3.86 (s, 3H), 2.91 (dd, J=14.2, 2.9 Hz, 1H), 2.76 (dd, J=14.9, 10.2 Hz, 1H); IR (KBr) 3780, 3450, 3380, 3270, 3000, 3020, 2940, 1735, 1725, 1705, 1700, 1695, 1660, 1645, 1640, 1605, 1595, 1560, 1535, 1520, 1505 cm$^{-1}$ MS (CI, positive) m/z 638 (MR +), 472, 253

(4) To a mixed solution of the target compound in step (3) (300 mg, 0.470 mmol) in DMSO (3 mL) and toluene (3 mL) were added WSCI hydrochloride (451 mg, 2.35 mmol) and dichloroacetic acid (19.4 μL). The resulting mixture was stirred at room temperature for 5 h. Ethyl acetate (100 mL) was added and the mixture was washed with 1N hydrochloric acid, saturated aqueous sodium hydrogencarbonate solution and saturated brine, dried over anhydrous magnesium sulfate, and concentrated under reduced pressure. The residue was separated and purified by silica gel column chromatography (dichloromethane-ethyl acetate, 4:1) to give 176 mg (59%) of the title compound as pale-yellow crystals.

mp 186.0–189.0° C.; $^1$H-NMR (500 MHz, DMSO-d$_6$) δ 8.55 (s, 1H), 8.08 (d, J=9.6 Hz, 1H), 7.98 (d, J=8.5 Hz, 2H), 7.87 (d, J=7.6 Hz, 1H), 7.59 (d, J=8.5 Hz, 2H), 7.45 (t, J=7.5 Hz, 1H), 7.33 (t, J=7.5 Hz, 2H), 7.23 (d, J=7.5 Hz, 2H), 7.21–7.15 (m, 3H), 7.10 (s, 1H), 7.05 (s, 1H), 6.14 (d, J=7.6 Hz, 1H), 5.28 (s, 2H), 4.31 (m, 2H), 4.22 (m, 1H), 3.86 (s, 3H), 3.12 (dd, J=14.2, 2.3 Hz, 1H), 2.62 (dd, J=14.2, 11.2 Hz, 1H); IR (KBr) 3380, 3290, 3070, 3010, 2930, 1715, 1665, 1640, 1600, 1590, 1560, 1520, 1510 cm$^{-1}$ MS (CI, positive) m/z 636 (MH$^+$), 470, 253

EXAMPLE 71

Synthesis of 2-[3-[4-(carboxy)benzyloxycarbonyl]amino-2-oxo-6-phenyl-1,2-dihydro-1-pyridyl]-N-(1-benzyl-3,3,3-trifluoro-2-oxopropyl)-acetamide.

To a solution of the title compound in Example 70 (110 mg, 0.173 mmol) in THF (1 mL) was added an aqueous solution (0.3 mL) of lithium hydroxide (18.2 mg, 0.433 mmol). The resulting mixture was stirred at room temperature overnight. 1N Hydrochloric acid was added adjust the mixture to pH 3, and then concentrated under reduced pressure. The residue was dissolved in ethyl acetate (100 mL), and the mixture was washed with water and saturated brine, dried over anhydrous magnesium sulfate, and concentrated under reduced pressure. The residue was separated and purified by silica gel column chromatography (dichloromethane-ethyl acetate-acetic acid, 75:25:1) to give 52 mg (48%) of the title compound as colorless crystals.

mp 214.0–216.0° C.; ¹H-NMR (500 MHz, DMSO-d$_6$+D$_2$O) δ 7.96 (d, J=8.3 Hz, 2H), 7.88 (d, J=7.7 Hz, 1H), 7.57 (d, J=8.3 Hz, 2H), 7.47–7.43 (m, 1H), 7.34 (t, J=7.8 Hz, 2H), 7.26–7.10 (m, 7H), 6.16 (d, J=7.7 Hz, 1H), 5.27 (s, 2H), 4.57 (s, 1H), 4.31 (s, 1H), 4.22 (m, 1H), 3.11 (dd, J=14.3, 2.6 Hz, 1H), 2.61 (dd, J=14.3, 11.3 Hz, 1H); IR (KBr) 3350, 3280, 3080, 2930, 2610, 2500, 2300, 1750, 1735, 1720, 1705, 1695, 1680, 1660, 1635, 1610, 1600, 1590, 1560, 1535, 1525, 1505 cm⁻¹ MS (CI, positive) m/z 622 (MH⁺), 470, 444, 253

EXAMPLE 72

Synthesis of 2-[3-[3-(methoxycarbonyl)benzyloxycarbonyl]amino-2-oxo-6-phenyl-1,2-dihydro-1-pyridyl]-N-(1-benzyl-3,3,3-trifluoro-2-oxopropyl)acetamide.

(1) 2-[3-[3-(Methoxycarbonyl)benzyloxycarbonyl]amino-2-oxo-6-phenyl-1,2-dihydro-1-pyridyl]-N-[1-benzyl-2-(tert-butyldimethylsilyl)oxy-3,3,3-trifluoropropyl]acetamide was synthesized in the same manner as in Example 53. That is, the target compound in Example 70-(1) (500 mg, 0.893 mmol) was reacted with triethylamine (1.00 mL, 7.20 mmol), triphosgene (150 mg, 0.505 mmol) and methyl 3-hydroxymethylbezoate (450 mg, 2.71 mmol) in dichloromethane (10 mL) to give 549 mg (81%) of the target compound as pale-yellow crystals.

mp 69–71° C.; ¹H-NMR (500 MHz, DMSO-d$_6$) δ 8.55 (s, 1H), 8.19 (d, J=7.4 Hz, 1H), 8.04 (s, 1H), 7.93 (d, J=7.8 Hz, 1H), 7.88 (d, J=7.6 Hz, 1H), 7.74 (d, J=7.8 Hz, 1H), 7.55 (t, J=7.8 Hz, 1H), 7.46 (d, J=7.8 Hz, 1H), 7.37 (t, J=7.8 Hz, 2H), 7.31–7.19 (m, 5H), 7.13 (d, J=8.2 Hz, 2H), 6.18 (d, J=7.6 Hz, 1H), 5.27 (s, 2H), 4.39 (d, J=16.3 Hz, 1H), 4.33 (d, J=16.3 Hz, 1H), 4.22 (m, 1H), 4.08 (m, 1H), 3.87 (s, 3H), 2.93 (dd, J=14.9, 2.3 Hz, 1H), 2.70 (dd, J=14.9, 11.2 Hz, 1H), 0.90 (s, 9H), 0.08 (s, 6H); IR (KBr) 3370, 3290, 3050, 3010, 2930, 2920, 2850, 1720, 1675, 1640, 1600, 1580, 1510 cm⁻¹

(2) 2-[3-[3-(Methoxycarbonyl)benzyloxycarbonyl]amino-2-oxo-6-phenyl-1,2-dihydro-1-pyridyl]-N-(1-benzyl-2-hydroxy-3,3,3-trifluoro-propyl)acetamide was synthesized in the same manner as in Example 53. That is, the target compound in step (1) (450 mg, 0.598 mmol) was treated with a THF solution (1.0 M, 0.718 mL, 0.718 mmol) of tetrabutylammonium fluoride in THF (5 mL) to give 381 mg (99%) of the target compound as pale-yellow crystals.

mp 208.0–209.5° C.; ¹H-NMR (500 MHz, DMSO-d$_6$) δ 8.59 (s, 1H), 8.28 (d, J=8.6 Hz, 1H), 8.07 (s, 1H), 7.97 (dt, J=1.9, 7.7 Hz, 1H), 7.93 (d, J=7.6 Hz, 1H), 7.77 (d, J=7.8 Hz, 1H), 7.59 (t, J=7.7 Hz, 1H), 7.50 (m, 1H), 7.40 (t, J=7.8 Hz, 2H), 7.31 (d, J=7.1 Hz, 2H), 7.27–7.20 (m, 5H), 7.15 (m, 1H), 6.21 (d, J=7.6 Hz, 1H), 5.30 (s, 2H), 4.43 (d, J=16.3 Hz, 1H), 4.25 (d, J=16.3 Hz, 1H), 4.10 (m, 1H), 3.96 (m, 1H), 2.95 (dd, J=14.3, 2.9 Hz, 1H), 2.80 (dd, J=14.3, 10.2 Hz, 1H); IR (KBr) 3350, 3250, 3050, 3020, 3000, 2950, 1720, 1675, 1640, 1605, 1590, 1560, 1520 cm⁻¹ MS (CI, positive) m/z 638 (MH⁺), 472, 253

(3) 2-[3-[3-(Methoxycarbonyl)benzyloxycarbonyl]amino-2-oxo-6-phenyl-1,2-dihydro-1-pyridyl]-N-(1-benzyl-3,3,3-trifluoro-2-oxopropyl)-acetamide was synthesized in the same manner as in Example 53. That is, the target compound in step (2) (74.2 mg, 0.116 mmol) was reacted with Dess-Martin periodinane (98.7 mg, 0.233 mmol) in dichloromethane (2 mL) to give 42.6 mg (58%) of the title compound as pale-yellow crystals.

mp 197.0–199.0° C.; ¹H-NMR (500 MHz, DMSO-d$_6$) δ 8.51 (s, 1H), 8.08 (d, J=9.5 Hz, 1H), 8.03 (s, 1H), 7.93 (d, J=7.9 Hz, 2H), 7.86 (d, J=7.6 Hz, 1H), 7.74 (d, J=7.8 Hz, 1H), 7.55 (t, J=7.8 Hz, 1H), 7.52–7.40 (m, 1H), 7.33 (t, J=7.9 Hz, 2H), 7.22 (d, J=7.2 Hz, 2H), 7.20–7.17 (m, 5H), 6.14 (d, J=7.6 Hz, 1H), 5.26 (s, 2H), 4.30 (s, 2H), 4.21 (m, 1H), 3.87 (s, 3H), 3.11 (dd, J=14.2, 2.2 Hz, 1H), 2.61 (dd, J=14.2, 11.4 Hz, 1H); IR (KBr) 3350, 1715, 1660, 1640, 1585, 1540, 1520, 1505 cm⁻¹ MS (CI, positive) m/z 636 (MH⁺), 508, 470, 253

EXAMPLE 73

Synthesis of 2-[3-[3-(carboxy)benzyloxycarbonyl]amino-2-oxo-6-phenyl-1,2-dihydro-1-pyridyl]-N-(1-benzyl-3,3,3-trifluoro-2-oxopropyl)-acetamide.

The title compound was synthesized in the same manner as in Example 71. That is, the title compound in Example 72 (65.9 mg, 0.104 mmol) was treated with an aqueous solution (0.3 mL) of lithium hydroxide (4.79 mg, 0.114 mmol) in THF (1 mL) to give 13 mg (20%) of the title compound as pale-yellow crystals.

mp 205.0–207.0° C.; ¹H-NMR (500 MHz, DMSO-d$_6$) δ 8.49 (s, 1H), 8.08 (d, J=9.5 Hz, 1H), 8.01 (s, 1H), 7.90 (d, J=7.8 Hz, 2H), 7.87 (d, J=7.6 Hz, 1H), 7.69 (d, J=7.7 Hz, 1H), 7.52 (t, J=7.7 Hz, 1H), 7.50–7.40 (m, 1H), 7.33 (t, J=7.8 Hz, 2H), 7.23 (d, J=7.1 Hz, 2H), 7.20–7.10 (m, 5H), 6.14 (d, J=7.6 Hz, 1H), 5.25 (s, 2H), 4.30 (s, 2H), 4.21 (m, 1H), 3.11 (dd, J=14.2, 2.3 Hz, 1H), 2.61 (dd, J=14.2, 11.3 Hz, 1H); IR (KBr) 3350, 2900, 1720, 1705, 1690, 1680, 1675, 1665, 1660, 1640, 1620, 1585, 1560, 1515, 1505 cm⁻¹ MS (CI, positive) m/z 622 (MH⁺), 510, 470, 253

EXAMPLE 74

Synthesis of 2-[3-[4-(methoxycarbonyl)benzyloxycarbonyl]amino-2-oxo-1,2-dihydro-1-pyridyl]-N-(1-benzyl-3,3,3-trifluoro-2-oxopropyl)-acetamide.

(1) 2-(3-Amino-2-oxo-1,2-dihydro-1-pyridyl)-N-[1-benzyl-2-(tert-butyldimethylsilyl)oxy-3,3,3-trifluoropropyl)acetamide was synthesized in the same manner as in Example 2. That is, the target compound in Example 17-(1) (15.0 g, 24.3 mmol) was reacted under a hydrogen atmosphere in the presence of 10% palladium carbon (2.60 g) in THF (120 mL) to give 11.4 g (97%) of the target compound as a colorless solid.

¹H-NMR (500 MHz, DMSO-$_6$) δ 8.21 (d, J=7.8 Hz, 1H), 7.28 (t, J=7.4 Hz, 2H), 7.25–7.17 (m, 3H), 6.58 (dd, J=6.9, 1.6 Hz, 1H), 6.42 (dd, J=6.9, 1.6 Hz, 1H), 5.96 (t, J=6.9 Hz, 1H), 5.03 (s, 2H), 4.44 (ABq, J=15.0 Hz, 2H), 4.30 (m, 1H), 4.12 (m, 1H), 2.97 (dd, J=14.3, 2.1 Hz, 1H), 2.72 (dd, J=14.3, 11.3 Hz, 1H), 0.94 (s, 9H), 0.22 (s, 3H), 0.12 (s, 3H); IR (KBr) 3420, 3300, 3200, 3050, 2900, 2830, 1680, 1640, 1590, 1560, 1530 cm⁻¹

(2) 2-[3-[4-(Methoxycarbonyl)benzyloxycarbonyl]amino-2-oxo-1,2-dihydro-1-pyridyl]-N-(1-benzyl-2-hydroxy-3,3,3-trifluoropropyl)-acetamide was synthesized in the same manner as in Example 53. That is, the target compound in step (1) (1.00 g, 2.07 mmol) was reacted with triethylamine (2.30 mL, 16.6 mmol), triphosgene (347 mg, 1.17 mmol) and methyl 4-hydroxymethylbenzoate (1.04 g, 6.28 mmol) in dichloromethane (20 mL) to give a pale-yellow oil (mixture with methyl 4-hydroxymethylbezoate). The obtained oil was treated with a THF solution (1.0 M, 2.48 mL, 2.48 mmol) of tetrabutylammonium fluoride in THF (5 mL) to afford 905 mg (78%) of the target compound as colorless crystals.

mp 177.5–178.5° C.; $^1$H-NMR (500 MHz, DMSO-d$_6$) δ 8.50 (s, 1H), 8.41 (d, J=8.7 Hz, 1H), 7.97 (d, J=8.2 Hz, 2H), 7.82 (d, J=7.2 Hz, 1H), 7.57 (d, J=8.2 Hz, 2H), 7.30–7.18 (m, 5H), 7.07 (dd, J=1.5, 6.9 Hz, 1H), 6.70 (d, J=6.9 Hz, 1H), 6.22 (t, J=7.2 Hz, 1H), 5.26 (s, 2H), 4.58 (d, J=15.7 Hz, 1H), 4.45 (d, J=15.7 Hz, 1H), 4.13 (m, 1H), 4.00 (m, 1H), 3.86 (s, 3H), 2.98 (dd, J=14.1, 2.7 Hz, 1H), 2.79 (dd, J=14.1, 10.5 Hz, 1H); IR (KBr) 3350, 3280, 3070, 3010, 3000, 2930, 1730, 1720, 1650, 1580, 1560, 1520, 1515, 1505 cm$^{-1}$ MS (CI, positive) m/z 562 (MH$^+$), 396, 369

(3) 2-[3-[4-(Methoxycarbonyl)benzyloxycarbonyl]amino-2-oxo-1,2-dihydro-1-pyridyl]-N-(1-benzyl-3,3,3-trifluoro-2-oxopropyl)acetamide was synthesized in the same manner as in Example 53. That is, the target compound in step (2) (300 mg, 0.470 mmol) was reacted with Dess-Martin periodinane (566 mg, 1.34 mmol) in dichloromethane (60 mL) to give 258 mg (86%) of the title compound as slightly red crystals.

mp 131.5–133.0° C.; $^1$H-NMR (500 MHz, DMSO-d$_6$) δ 8.49 (s, 1H), 8.20 (d, J=9.9 Hz, 1H), 7.96 (d, J=8.2 Hz, 2H), 7.79 (dd, J=1.4, 7.3 Hz, 1H), 7.57 (d, J=8.2 Hz, 2H), 7.26–7.10 (m, 5H), 7.15 (s, 1H), 7.10 (s, 1H), 6.82 (dd, J=6.9, 1.7 Hz, 1H), 6.18 (t, J=7.2 Hz, 1H), 5.25 (s, 2H), 4.61 (d, J=15.7 Hz, 1H), 4.41 (d, J=15.7 Hz, 1H), 4.25 (m, 1H), 3.85 (s, 3H), 3.12 (dd, J=13.8, 2.5 Hz, 1H), 2.66 (dd, J=13.8, 11.6 Hz, 1H); IR (KBr) 3350, 3290, 3050, 3020, 2990, 2950, 1720, 1715, 1710, 1700, 1695, 1690, 1660, 1650, 1645, 1635, 1630, 1625, 1615, 1580, 1560, 1520, 1515 cm$^{-1}$ MS (CI, positive) m/z 560 (MH$^+$), 394, 369, 343, 303

EXAMPLE 75

Synthesis of 2-[3-[4-(carboxy)benzyloxycarbonyl]amino-2-oxo-1,2-dihydro-1-pyridyl]-N-(1-benzyl-3,3,3-trifluoro-2-oxopropyl)acetamide.

The title compound was synthesized in the same manner as in Example 71. That is, the title compound in Example 74 (150 mg, 0.268 mmol) was treated with an aqueous solution (0.5 mL) of lithium hydroxide (25.2 mg, 0.600 mmol) in THF (2 mL) to give 30 mg (21%) of the title compound as colorless crystals.

mp 163.0–164.0° C.; $^1$H-NMR (500 MHz, DMSO-d$_6$) δ 8.46 (s, 1H), 8.20 (d, J=9.9 Hz, 1H), 7.94 (d, J=8.3 Hz, 2H), 7.79 (dd, J=1.5, 7.3 Hz, 1H), 7.54 (d, J=8.3 Hz, 2H), 7.30–7.10 (m, 5H), 7.16 (s, 1H), 7.10 (s, 1H), 6.82 (dd, J=6.9, 1.8 Hz, 1H), 6.17 (t, J=7.1 Hz, 1H), 5.24 (s, 2H), 4.60 (d, J=15.7 Hz, 1H), 4.41 (d, J=15.7 Hz, 1H), 4.25 (m, 1H), 3.12 (dd, J=13.9, 2.7 Hz, 1H), 2.66 (dd, J=13.9, 11.6 Hz, 1H); IR (KBr) 3260, 3050, 2950, 2600, 2450, 2300, 1730, 1720, 1700, 1680, 1670, 1650, 1640, 1580, 1560, 1545, 1535, 1505 cm$^{-1}$ MS (CI, positive) m/z 546 (MH$^+$), 528, 510, 394, 376, 366, 350

EXAMPLE 76

Synthesis of 2-[3-[3-(methoxycarbonyl)benzyloxycarbonyl]amino- 2-oxo-1,2-dihydro-1-pyridyl]-N-(1-benzyl-3,3,3-trifluoro-2-oxopropyl)-acetamide.

(1) 2-[3-[3-(Methoxycarbonyl)benzyloxycarbonyl]amino-2-oxo-1,2-dihydro-1-pyridyl]-N-(1-benzyl-2-hydroxy-3,3,3-trifluoropropyl)-acetamide was synthesized in the same manner as in Example 53. That is, the target compound in Example 74-(1) (1.00 g, 2.07 mmol) was reacted with triethylamine (2.30 mL, 16.6 mmol), triphosgene (347 mg, 1.17 mmol) and methyl 3-hydroxymethylbenzoate (1.04 g, 6.28 mmol) in dichloromethane (20 mL) to give a pale-yellow oil (mixture with methyl 3-hydroxymethylbenzoate). The obtained oil was treated with a THF solution (1.0 M, 2.48 mL, 2.48 mmol) of tetrabutylammonium fluoride in THF (5 mL) to afford 830 mg (72%) of the target compound as colorless crystals.

mp 172.0–173.0° C.; $^1$H-NMR (500 MHz, DMSO-d$_6$) δ 8.45 (s, 1H), 8.40 (d, J=8.7 Hz, 1H), 8.02 (s, 1H), 7.92 (d, J=7.8 Hz, 1H), 7.82 (dd, J=7.3, 1.3 Hz, 1H), 7.72 (d, J=7.7 Hz, 1H), 7.54 (t, J=7.7 Hz, 1H), 7.29–7.17 (m, 5H), 7.07 (dd, J=1.7, 6.9 Hz, 1H), 6.69 (d, J=7.0 Hz, 1H), 6.22 (t, J=7.1 Hz, 1H), 5.24 (s, 2H), 4.58 (d, J=15.7 Hz, 1H), 4.44 (d, J=15.7 Hz, 1H), 4.13 (m, 1H), 3.99 (m, 1H), 3.86 (s, 3H), 2.97 (dd, J=14.1, 2.8 Hz, 1H), 2.78 (dd, J=14.1, 10.5 Hz, 1H); IR (KBr) 3380, 3270, 3080, 3050, 3005, 2995, 2920, 1730, 1715, 1660, 1645, 1585, 1555, 1505 cm$^{-1}$ MS (CI, positive) m/z 562 (MH$^+$), 396, 369

(2) 2-[3-[3-(Methoxycarbonyl)benzyloxycarbonyl]amino-2-oxo-1,2-dihydro-1-pyridyl]9-N-(1-benzyl-3,3,3-trifluoro-2-oxopropyl)acetamide was synthesized in the same manner as in Example 53. That is, the target compound in step (1) (300 mg, 0.470 mmol) was reacted with Dess-Martin periodinane (566 mg, 1.34 mmol) in dichloromethane (60 mL) to give 269 mg (90%) of the title compound as slightly red crystals.

mp 116.5–118.0° C.; $^1$H-NMR (500 MHz, DMSO-d$_6$) δ 8.44 (s, 1H), 8.20 (d, J=9.8 Hz, 1H), 8.01 (s, 1H), 7.92 (d, J=7.8 Hz, 1H), 7.78 (dd, J=1.4, 7.3 Hz, 1H), 7.71 (d, J=7.7 Hz, 1H), 7.54 (t, J=7.7 Hz, 1H), 7.25–7.13 (m, 5H), 7.15 (s, 1H), 7.10 (s, 1H), 6.82 (dd, J=6.9, 1.7 Hz, 1H), 6.18 (t, J=7.2 Hz, 1H), 5.23 (s, 2H), 4.60 (d, J=15.7 Hz, 1H), 4.41 (d, J=15.7 Hz, 1H), 4.25 (m, 1H), 3.86 (s, 3H), 3.12 (dd, J=13.9, 2.5 Hz, 1H), 2.65 (dd, J=13.9, 11.6 Hz, 1H); IR (KBr) 3520, 3350, 3300, 3200, 3090, 3080, 3010, 2930, 2840, 1730, 1720, 1680, 1645, 1600, 1560, 1545, 1525, 1520, 1510 cm$^{-1}$ MS (CI, positive) m/z 560 (MH$^+$), 394, 366, 343

EXAMPLE 77

Synthesis of 2-[3-[3-(carboxy)benzyloxycarbonyl]amino-2-oxo-1,2-dihydro-1-pyridyl]-N-(1-benzyl-3,3,3-trifluoro-2-oxopropyl)acetamide.

The title compound was synthesized in the same manner as in Example 71. That is, the title compound in Example 76 (150 mg, 0.268 mmol) was treated with an aqueous solution (0.5 mL) of lithium hydroxide (25.2 mg, 0.600 mmol) in THF (2 mL) to give 50 mg (34%) of the title compound as colorless crystals.

mp 137.0–138.5° C.; $^1$H-NMR (500 MHz, DMSO-d$_6$) δ 14–11.5 (bs, 1H), 8.43 (s, 1H), 8.19 (d, J=9.8 Hz, 1H), 7.90 (d, J=7.8 Hz, 1H), 7.78 (dd, J=1.5, 7.4 Hz, 1H), 7.67 (d, J=7.7 Hz, 1H), 7.51 (t, J=7.7 Hz, 1H), 7.25–7.15 (m, 5H), 7.16 (s, 1H), 7.10 (s, 1H), 6.82 (dd, J=6.9, 1.7 Hz, 1H), 6.17 (t, J=7.21 Hz, 1H), 5.22 (s, 2H), 4.59 (d, J=15.7 Hz, 1H), 4.40 (d, J=15.7 Hz, 1H), 4.24 (m, 1H), 3.11 (dd, J=13.8, 2.6 Hz, 1H), 2.64 (dd, J=13.8, 11.6 Hz, 1H); IR (KBr) 3500, 3360, 3300, 3200, 3050, 1730, 1680, 1675, 1665, 1645, 1635, 1595, 1580, 1575, 1510, 1505 cm$^{-1}$ MS (CI, positive) m/z 546 (MH$^+$), 528, 394, 376

EXAMPLE 78
Synthesis of 2-(5-acetylamino-6-oxo-2-phenyl-1,6-dihydro-1-pyrimidyl)-N-(1-benzyl-3,3,3-trifluoro-2-oxopropyl) acetamide.

The title compound was synthesized in the same manner as in Example 55. That is, the title compound in Example 2 (559 mg, 1.26 mmol) was reacted with sodium carbonate (372 mg, 3.51 mmol) and acetyl chloride (0.10 mL, 1.4 mmol) in THF (10 mL) to give 509 mg (83%) of the title compound as colorless crystals.

mp 110–112° C.; $^1$H-NMR (500 MHz, DMSO-d$_6$+D$_2$O) δ 8.73 (s, 1H), 7.53 (t, J=7.5 Hz, 1H), 7.38 (t, J=7.5 Hz, 2H), 7.29 (d, J=7.5 Hz, 2H), 7.23–7.13 (m, 5H), 4.42 (d, J=15.9 Hz, 1H), 4.33 (d, J=15.9 Hz, 1H), 4.26 (dd, J=11.5, 2.2 Hz, 1H), 3.13 (dd, J=13.9, 2.2 Hz, 1H), 2.59 (dd, J=13.9, 11.5 Hz, 1H), 2.15 (s, 3H); IR (KBr) 3300, 1640, 1515 cm$^{-1}$ MS (SIMS, positive) m/z 487 (MH$^+$)

EXAMPLE 79
Synthesis of 2-[2-(4-fluorophenyl)-5-methoxysuccinylamino-6-oxo-1,6-dihydro-1-pyrimidyl]-N-(1-benzyl-3,3,3-trifluoro-2-oxopropyl)-acetamide.

The title compound was synthesized in the same manner as in Example 55. That is, the title compound in Example 4 (600 mg, 1.30 mmol) was reacted with sodium carbonate (384 mg, 3.62 mmol) and methylsuccinyl chloride (0.18 mL, 1.5 mmol) in THF (12 mL) to give 736 mg (98%) of the title compound as a colorless amorphous.

$^1$H-NMR (500 MHz, DMSO-d$_6$+D$_2$O) δ 8.73 (s, 1H), 7.34 (dd, J=8.5, 5.5 Hz, 2H), 7.22–7.12 (m, 7H), 4.45 (d, J=16.5 Hz, 1H), 4.27 (m, 1H), 4.25 (dd, J=11.3, 2.1 Hz, 1H), 3.60 (s, 3H), 3.12 (dd, J=14.2, 2.1 Hz, 1H), 2.76 (t, J=7.3 Hz, 2H), 2.62–2.54 (m, 3H); IR (KBr) 3300, 1720, 1655, 1645, 1605, 1525, 1500 cm$^{-1}$

EXAMPLE 80
Synthesis of 2-[2-(4-fluorophenyl)-5-hydroxysuccinylamino-6-oxo-1,6-dihydro-1-pyrimidyl]-N-(1-benzyl-3,3,3-trifluoro-2-oxopropyl)acetamide.

The title compound was synthesized in the same manner as in Example 60. That is, the title compound in Example 79 (347 mg, 0.602 mmol) was reacted with 0.1N aqueous sodium hydroxide solution (10 mL) in THF (10 mL) to give 295 mg (87%) of the title compound as colorless crystals.

mp 140–147° C.; $^1$H-NMR (500 MHz, DMSO-d$_6$+D$_2$O) δ 8.75 (s, 1H), 7.35 (dd, J=8.5, 5.5 Hz, 2H), 7.22–7.12 (m, 7H), 4.45 (d, J=16.2 Hz, 1H), 4.27 (m, 1H), 4.25 (dd, J=11.5, 2.0 Hz, 1H), 3.12 (dd, J=13.9, 2.0 Hz, 1H), 2.71 (t, J=6.3 Hz, 2H), 2.59 (dd, J=13.9, 11.5 Hz, 1H), 2.51 (t, J=6.3 Hz, 2H); IR (KBr) 3320, 3280, 3060, 1680, 1655, 1645, 1600, 1540, 1520 cm$^{-1}$ MS (SIMS, negative) m/z 561 ((M–H)$^-$]

EXAMPLE 81
Synthesis of 2-[5-methoxysuccinylamino-6-oxo-2-(m-tolyl)-1,6-dihydro-1-pyrimidyl]-N-(1-benzyl-3,3,3-trifluoro-2-oxopropyl)aacetamide.

The title compound was synthesized in the same manner as in Example 55. That is, the title compound in Example 8 (350 mg, 0.763 mmol) was reacted with sodium carbonate (226 mg, 2.13 mmol) and methylsuccinyl chloride (0.11 mL, 0.89 mmol) in THF (8 mL) to give 250 mg (57%) of the title compound as a colorless amorphous.

$^1$H-NMR (500 MHz, DMSO-d$_6$+D$_2$O) δ 8.72 (s, 1H), 7.34 (d, J=7.8 Hz, 1H), 7.24 (t, J=7.8 Hz, 1H), 7.21–7.12 (m, 6H), 7.05 (d, J=7.8 Hz, 1H), 4.38 (brs, 2H), 4.21 (dd, J=11.6, 2.4 Hz, 1H), 3.60 (s, 3H), 3.12 (dd, J=14.2, 2.4 Hz, 1H), 2.76 (t, J=7.1 Hz, 2H), 2.63–2.55 (m, 3H), 2.31 (s, 3H); IR (KBr) 3250, 1720, 1645, 1510 cm$^{-1}$

EXAMPLE 82
Synthesis of 2-[5-hydroxysuccinylamino-6-oxo-2-(m-tolyl)-1,6-dihydro-1-pyrimidyl]-N-(1-benzyl-3,3,3-trifluoro-2-oxopropyl)acetamide.

The title compound was synthesized in the same manner as in Example 60. That is, the title compound in Example 81 (203 mg, 0.355 mmol) was reacted with 0.1N aqueous sodium hydroxide solution (5 mL) in THF (5 mL) to give the title compound (quant.) as a colorless amorphous.

$^1$H-NMR (500 MHz, DMSO-d$_6$) δ 12.13 (brs, 1H), 9.47 (s, 1H), 8.76 (s, 1H), 8.16 (d, J=9.7 Hz, 1H), 7.31 (d, J=7.7 Hz, 1H), 7.23–7.10 (m, 9H), 7.06 (d, J=7.6 Hz, 1H), 4.37 (brs, 2H), 4.21 (m, 1H), 3.12 (dd, J=14.0, 2.1 Hz, 1H), 2.71 (t, J=7.1 Hz, 2H), 2.59 (dd, J=14.0, 11.2 Hz, 1H), 2.49 (t, J=7.1 Hz, 2H), 2.30 (s, 3H)

EXAMPLE 83
Synthesis of 2-[5-amino-6-oxo-2-(m-tolyl)-1,6-dihydro-1-pyrimidinyl]-N-[1-benzyl-3,3-difluoro-2-oxo-3-[N-(carboxymethyl)carbamoyl]propyl]-acetamide.

(1) To a solution of DL-phenylalanine (25.26 g, 0.1529 mol) in 1,4-dioxane (300 mL), 1N aqueous sodium hydroxide solution (153 mL) and water (153 mL) was added dropwise di-tert-butyl dicarbonate (39 mL, 0.17 mol) under ice-cooling. The resulting mixture was allowed to warm to room temperature with stirring for 21 h, and concentrated to ca. 200 mL. Ethyl acetate (450 mL) was added to the concentrate and then citric acid was added under ice-cooling to adjust the pH to 3. The organic layer was separated, and the aqueous layer was further extracted with ethyl acetate. The combined organic layers were washed with water, dried over anhydrous sodium sulfate, and concentrated under reduced pressure. The residue was crystallized from ethyl acetate-hexane to give 35.42 g (87%) of N-tert-butoxycarbonyl-DL-phenylalanine as colorless crystals.

(2) To a solution of the target compound in step (1) (10.37 g, 39.08 mmol) in dichloromethane (300 mL) were added triethylamine (5.6 mL, 40 mmol), benzotriazol-1-yloxytris (dimethylamino)phosphonium hexafluorophosphate (17.33 g, 39.18 mmol), N,O-dimethylhydroxylamine hydrochloride (4.23 g, 43.4 mmol) and triethylamine (6.0 mL, 43 mmol). The resulting mixture was stirred at room temperature for 3 h. Triethylamine (2.1 mL, 15 mmol) was added, and after 25 min, triethylamine (1.0 mL. 7.2 mmol) was again added. The mixture was stirred for 10 min, diluted with dichloromethane (1000 mL), washed successively with 3N hydrochloric acid, saturated aqueous sodium hydrogencarbonate solution and saturated brine, dried over anhydrous magnesium sulfate, and concentrated under reduced pressure. The residue was separated by silica gel column chromatography (ethyl acetate-hexane, 1:1) and further recrystallized from ethyl acetate-hexane to give 10.17 g (84%) of N-tert-butoxycarbonyl-DL-phenylalanine-N-methoxy-N-methylamide as colorless crystals.

(3) To a mixed solution of the target compound in step (2) (10.01 g, 32.46 mmol) in ether (325 mL) and THF (100 mL) was added lithium aluminum hydride (1.54 g, 40.6 mmol). The resulting mixture was stirred at room temperature for 40 min and cooled with ice. An aqueous solution of potassium hydrogensulfate (7.74 g/160 mL) was added. The mixture was stirred for 40 min and diluted with ether (400 mL). The organic layer was separated, and the aqueous layer was further extracted with ether. The organic layers were combined and washed successively with 3N hydrochloric acid, saturated aqueous sodium hydrogencarbonate solution and saturated brine, and dried over anhydrous magnesium sulfate. Evaporation of the solvent under reduced pressure gave 7.36 g (91%) of N-tert-butoxycarbonyl-DL-phenylalaninal as a colorless solid.

(4) To a mixture of activated zinc powder (4.76 g, 72.8 mmol) and THF (15 mL) was added dropwise a solution of the target compound in step (3) (7.23 g, 29.0 mmol) and ethyl bromodifluoroacetate (9.3 mL, 73 mmol) in THF (65 mL) over 10 min with ultrasonication. The resulting mixture was ultrasonicated with occasional stirring for 27 min, refluxed under heating for 7 min and cooled with ice. 1N Aqueous potassium hydrogensulfate solution (100 mL) was added and the mixture was diluted with 1N aqueous potassium hydrogensulfate solution (200 mL) and then extracted with dichloromethane. The extract was washed with saturated brine, dried over anhydrous magnesium sulfate and concentrated under reduced pressure. The residue was separated and purified by silica gel column chromatography (hexane-ethyl acetate, 65:35) and silica gel column chromatography (hexane-ethyl acetate, 2:1) to give 3.38 g (31%) of ethyl 4(S*)-[(tert-butoxycarbonyl)amino]-2-2-difluoro-3 (R*)-hydroxy-5-phenylpentanoate as a colorless solid.

(5) To a solution of the target compound in step (4) (2.14 g, 5.74 mmol) in THF (12 mL) was added dropwise 1N aqueous sodium hydroxide solution (5.9 mL). The resulting mixture was stirred at room temperature for 2.5 h, and THF was evaporated under reduced pressure. The obtained aqueous solution was diluted with water (10 mL), and then lyophilized to give 2.14 g (100%) of sodium 4(S*)-[(tert-butoxycarbonyl)amino]-2-2-difluoro-3(R*)-hydroxy-5-phenylpentanoate as a slightly yellow solid.

(6) To a solution of the target compound of step (5) (1.62 g, 4.43 mmol), HOBT (1.21 g, 8.97 mmol) and glycine benzyl ester p-toluenesulfonate (1.51 g, 4.46 mmol) in DMF (20 mL) were added N-ethylmorpholine (0.57 mL, 4.5 mmol) and WSCI hydrochloride (907 mg, 4.73 mmol). The resulting mixture was stirred at room temperature for 19 h, diluted with water, and then extracted with ethyl acetate. The extract was washed successively with saturated aqueous sodium hydrogencarbonate solution, 10% aqueous citric acid solution and saturated brine, dried over anhydrous magnesium sulfate and concentrated under reduced pressure. The residue was separated and purified by silica gel column chromatography (hexane-ethyl acetate, 3:2) to give 1.51 g (69%) of benzyl 2-[4(S*)-[(tert-butoxycarbonyl)-amino]-2-2-difluoro-3(R*)-hydroxy-5-phenylpentanoylamino]acetate as a colorless oil.

(7) To a solution of the target compound in step (6) (1.47 g, 2.99 mmol) in 1,4-dioxane (5 mL) was added a solution (5.3N, 20 mL) of hydrogen chloride in 1,4-dioxane. The resulting mixture was stirred at room temperature for 30 min and then concentrated under reduced pressure. The residue was crystallized from ether to give 1.40 g (96%) of benzyl 2-[4(S*)-amino-2-2-difluoro-3(R*)-hydroxy-5-phenylpentanoylamino]acetate hydrochloride as a colorless solid.

$^1$H-NMR (300 MHz, DMSO-d$_6$) δ 9.44 (brs, 1H), 8.07 (brs, 3H), 7.43–7.23 (m, 11H), 5.16 (s, 2H), 4.00 (brs, 2H), 3.97–3.87 (1H), 3.68 (dd, J=9.8, 4.5 Hz, 1H), 3.10 (dd, J=13.5, 4.7 Hz, 1H), 2.89 (dd, J=9.8, 4.5 Hz); IR (KBr) 3150, 2900, 1745, 1670, 1560 cm$^{-1}$ (8) In the same manner as in Example 1, [5-benzyloxycarbonylamino-6-oxo-2-(m-tolyl)-1,6-dihydro-1-pyrimidinyl]acetic acid (title compound in Reference Example 5, 653 mg, 1.66 mmol) and the target compound in step (7) (710 mg, 1.66 mmol) were subjected to amide bond formation followed by oxidation. The compound obtained was deprotected in the same manner as in Example 2 to give the title compound as a pale-brown solid.

mp 128–132° C.; $^1$H-NMR (500 MHz, DMSO-d$_6$) δ 9.41 (t, J=5.6 Hz, 1H), 8.93 (d, J=7.1 Hz, 1H), 7.31 (s, 1H), 7.28–7.05 (m, 9H), 5.13 (brs, 2H), 4.93 (m, 1H), 4.41 (d, J=16.5 Hz, 1H), 4.35 (d, J=16.6 Hz, 1H), 3.81 (d, J=5.7 Hz, 2H), 3.17 (dd, J=14.2, 3.8 Hz, 1H), 2.71 (dd, J=14.3, 9.8 Hz, 1H), 2.29 (s, 3H); IR (KBr) 3250, 3000, 2900, 1645, 1600, 1520 cm$^{-1}$ MS (SIMS, positive) m/z 560 (hydrate, MH$^+$), 542 (MH$^+$)

EXAMPLE 84

Synthesis of 2-(5-amino-6-oxo-2-(m-tolyl)-1,6-dihydro-1-pyrimidinyl]-N-[1-benzyl-3,3-difluoro-2-oxo-3-[N-(carboxyethyl)carbamoyl]propyl]-acetamide.

(1) In the saae manner as in Example 83-(6) except for using β-alanine benzyl ester p-toluenesulfonate instead of glycine benzyl ester p-toluenesulfonate, 871 mg (78%) of benzyl 3-[4(S*)-[(tert-butoxycarbonyl)amino]-2-2-difluoro-3(R*)-hydroxy-5-phenylpentanoyl-amino]propionate was obtained as a colorless oil.

(2) In the same manner as in Example 83-(7), 740 mg (100%) of benzyl 3-[4(S*)-amino-2-2-difluoro-3(R*)-hydroxy-5-phenylpentanoylamino]-propionate hydrochloride was obtained as a pale-yellow solid from the target compound in step (1).

$^1$H-NMR (300 MHz, DMSO-d$_6$) δ 9.07 (t, J=5.3 Hz, 1H), 8.10 (brs, 3H), 7.44–7.24 (m, 10H), 7.18 (brs, 1H), 5.09 (s, 2H), 3.93 (t, J=12.9 Hz, 1H), 3.61 (dd, J=9.7, 4.5 Hz, 1H), 3.39 (m, 2H), 3.10 (dd, J=13.5, 4.6 Hz, 1H), 2.88 (dd, J=13.4, 10.3 Hz, 1H), 2.59 (t, J=7.0 Hz, 2H); IR (KBr) 3400, 3150, 3000, 2900, 1715, 1680, 1540 cm$^{-1}$ (3) In the same manner as in Example 1, [5-benzyloxycarbonylamino- 6-oxo-2-(m-tolyl)-1,6-dihydro-1-pyrimidinyl]acetic acid (title compound in Reference Example 5, 629 mg, 1.60 mmol) and the target compound in step (2) (705 mg, 1.59 mmol) were subjected to amide bond formation followed by oxidation. The compound obtained was deprotected in the same manner as in Example 2 to give the title compound as a slightly brown solid.

mp >152° C. (decomposition); $^1$H-NMR (500 MHz, DMSO-d$_6$) δ 9.18 (brs, 1H), 8.81 (d, J=7.3 Hz, 1H), 7.36–7.03 (m, 9H), 5.13 (brs, 2H), 4.94 (m, 1H), 4.41, 4.36 (ABq, J=16.5 Hz, 2H), 3.33 (m, 2H), 3.15 (dd, J=14.3, 3.8

Hz, 1H), 2.71 (dd, J=14.2, 9.5 Hz, 1H), 2.33 (t, J=7.3 Hz, 2H), 2.29 (s, 3H); IR (KBr) 3275, 3050, 2900, 1645, 1600, 1530 cm$^{-1}$ MS (SIMS, positive) m/z 574 (hydrate, MH$^+$), 556 (MH$^+$)

EXAMPLES 85–93

The compounds shown in Tables 6–7 were synthesized in the same manner as in Examples 83 and 84.

EXAMPLE 94

Synthesis of 2-[5-benzyloxycarbonylamino-6-oxo-2-(m-tolyl)-1,6-dihydro-1-pyrimidinyl]-N-[1(S)-benzyl-3,3-difluoro-2-oxo-3-(ethoxycarbonyl)propyl]acetamide.

(1) Ethyl 4(S)-amino-2,2-difluoro-3(R)-hydroxy-5-phenylpentanoate hydrochloride was synthesized in the same manner as in Example 83-(7). That is, ethyl 4(S)-[(tert-butoxycarbonyl)amino]-2,2-difluoro-3(R)-hydroxy-5-phenylpentanoate (an intermediate in Reference Example 6, 908 mg, 2.43 mmol) was treated with a solution of hydrogen chloride in 1,4-dioxane (4N, 6 mL) to give 750 mg (100%) of the target compound as a colorless solid.

(2) To a solution of [5-benzyloxycarbonylamino-6-oxo-2-(m-tolyl)-1,6-dihydro-1-pyrimidinyl]acetic acid (title compound in Reference Example 5, 950 mg, 2.41 mmol), the target compound in step (1) (748 mg, 2.41 mmol) and HOBT monohydrate (651 mg, 4.82 mmol) in DMF (10 mL) were added triethylamine (0.40 mL, 2.9 mmol) and WSCI hydrochloride (508 mg, 2.65 mmol). The resulting mixture was stirred at room temperature for 17 h, poured into 0.5N hydrochloric acid (60 mL), and then extracted with ethyl acetate. The extract was washed with saturated aqueous sodium hydrogencarbonate solution and saturated brine, dried over anhydrous magnesium sulfate and concentrated under reduced pressure. The residue was separated and purified by silica gel column chromatography (chloroform-methanol, 98:2) to give 1.77 g (96%) of 2-[5-benzyloxycarbonylamino-6-oxo-2-(m-tolyl)-1,6-dihydro-1-pyrimidinyl]-N-[1(S)-benzyl-3,3-difluoro-2(R)-hydroxy-3-(ethoxycarbonyl)propyl]acetamide as a colorless solid.

(3) In the same manner as in Example 53, the target compound in step (2) (1.70 g, 2.21 mmol) was treated with Dess-Martin periodinane (1.49 g, 3.51 mmol) in dichloromethane (20 mL) to give 1.30 g (91%) of the title compound as colorless crystals.

mp 138–140° C.; $^1$H-NMR (500 MHz, DMSO-d$_6$) δ 8.95 (d, J=6.8 Hz, 1H), 8.88 (s, 1H), 8.42 (s, 1H), 7.44 (d, J=7.1 Hz, 2H), 7.39 (t, J=7.1 Hz, 2H), 7.36–7.17 (m, 10H), 5.19 (s, 2H), 4.86 (m, 1H), 4.48 (d, J=16.6 Hz, 1H), 4.41 (d, J=16.6 Hz, 1H), 4.25 (q, J=7.1 Hz, 2H), 3.09 (dd, J=14.2, 5.0 Hz, 1H), 2.79 (dd, J=14.2, 9.0 Hz, 1H), 2.32 (s, 3H), 1.16 (t, J=7.1 Hz, 3H); IR (KBr) 3290, 3020, 2920, 1775, 1725, 1655, 1595, 1515 cm$^{-1}$ MS (SIMS, positive) m/z 647 (MH$^+$)

EXAMPLE 95

Synthesis of 2-[5-benzyloxycarbonylamino-6-oxo-2-(m-tolyl)-1,6-dihydro-1-pyrimidinyl]-N-[1(S)-benzyl-3,3-difluoro-2-oxo-3-carboxypropyl]acetamide.

The title compound was synthesized in the same manner as in Example 60. That is, the title compound in Example 94 (200 mg, 0.309 mmol) was reacted with 0.1N aqueous sodium hydroxide solution (4 mL) in THF (4 mL) to give 171 mg (89%) of the title compound as colorless crystals.

mp 109–113° C.; $^1$H-NMR (500 MHz, DMSO-d$_6$) δ 8.88 (s, 1H), 8.84 (d, J=7.3 Hz, 1H), 8.42 (s, 1H), 7.44 (d, J=7.1 Hz, 2H), 7.39 (t, J=7.1 Hz, 2H), 7.36–7.17 (m, 10H), 5.18 (s, 2H), 4.94 (m, 1H), 4.43 (m, 2H), 3.13 (dd, J=14.3, 4.1 Hz, 1H), 2.75 (dd, J=14.3, 9.4 Hz, 1H), 2.31 (s, 3H); IR (KBr) 3350, 3020, 1720, 1655, 1505 cm$^{-1}$ MS (SIMS, positive) m/z 619 (MH$^+$)

EXAMPLE 96

Synthesis of 2-[5-amino-6-oxo-2-(m-tolyl)-1,6-dihydro-1-pyrimidinyl]-N-[1(S)-benzyl-3,3-difluoro-2-oxo-3-(ethoxycarbonyl)propyl]acetamide.

The title compound was synthesized in the same manner as in Example 2. That is, the title compound in Example 94 (930 mg, 1.44 mmol) was reacted under a hydrogen atmosphere in the presence of 10% palladium carbon (306 mg) in methanol (10 mL) to give 682 mg (92%) of the title compound as colorless crystals.

mp 146–147° C.; $^1$H-NMR (500 MHz, DMSO-d$_6$) δ 8.89 (d, J=6.8 Hz, 1H), 7.31–7.09 (m, 10H), 5.12 (s, 2H), 4.85 (m, 1H), 4.44 (d, J=16.5 Hz, 1H), 4.36 (d, J=16.5 Hz, 1H), 4.25 (q, J=7.1 Hz, 2H), 3.09 (dd, J=14.1, 5.0 Hz, 1H), 2.81 (dd, J=14.1, 9.0 Hz, 1H), 2.30 (s, 3H), 1.18 (t, J=7.1 Hz, 3H); IR (KBr) 3400, 3310, 3020, 1750, 1640, 1605, 1520 cm$^{-1}$ MS (SIMS, positive) m/z 513 (MH$^+$)

EXAMPLE 97

Synthesis of 2-[5-amino-6-oxo-2-(m-tolyl)-1,6-dihydro-1-pyrimidinyl]-N-[1(S)-benzyl-3,3-difluoro-2-oxo-3 carboxypropyl]acetamide.

The title compound was synthesized in the same manner as in Example 60. That is, the title compound in Example 96 (90.2 mg, 0.176 mmol) was reacted with 0.1N aqueous sodium hydroxide solution (2.5 mL) in THF (2.5 mL) to give 71 mg (83%) of the title compound as colorless crystals.

mp 118–121° C.; $^1$H-NMR (500 MHz, DMSO-d$_6$) δ 8.79 (d, J=7.3 Hz, 1H), 7.31–7.10 (m, 10H), 4.94 (m, 1H), 4.42 (d, J=16.5 Hz, 1H), 4.37 (d, J=16.5 Hz, 1H), 3.13 (dd, J=14.2, 4.1 Hz, 1H), 2.75 (dd, J=14.2, 9.3 Hz, 1H), 2.30 (s, 3H); IR (KBr) 3400, 3300, 3050, 1690, 1655, 1605, 1555 cm$^{-1}$ MS (SIMS, negative) m/z 483 [(M–H)$^-$]

EXAMPLE 98

Synthesis of 2-[5-methoxysuccinylamino-6-oxo-2-(m-tolyl)-1,6-dihydro-1-pyrimidinyl]-N-[1(S)-benzyl-3,3difluoro-2-oxo-3-(ethoxy-carbonyl)propyl]acetamide.

The title compound was synthesized in the same manner as in Example 55. That is, the title compound in Example 96 (470 mg, 0.917 mmol) was reacted with sodium carbonate (272 mg, 2.57 mmol) and methylsuccinyl chloride (0.14 mL, 1.1 mmol) in THF (10 mL) to give 548 mg (95%) of the title compound as a colorless amorphous.

$^1$H-NMR (500 MHz, DMSO-d$_6$) δ 9.56 (s, 1H), 8.97 (d, J=6.8 Hz, 1H), 8.78 (s, 1H), 7.36–7.10 (m, 9H), 4.87 (m, 1H), 4.49 (d, J=16.8 Hz, 1H), 4.43 (d, J=16.8 Hz, 1H), 4.26 (q, J=7.1 Hz, 2H), 3.59 (s, 3H), 3.10 (dd, J=14.1, 5.0 Hz, 1H), 2.80 (dd, J=14.1, 9.0 Hz, 1H), 2.76 (t, J=7.0 Hz, 2H), 2.58 (t, J=7.0 Hz, 2H), 2.32 (s, 3H), 1.17 (t, J=7.1 Hz, 3H); IR (KBr) 3330, 1775, 1735, 1690, 1645, 1595, 1515 cm$^{-1}$ MS (SIMS, positive) m/z 627 (MH$^+$)

EXAMPLE 99

Synthesis of 2-[5-hydroxysuccinylamino-6-oxo-2-(m-tolyl)-1,6-dihydro-1-pyrimidinyl]-N-[1(S)-benzyl-3,3-difluorso-2-oxo-3 carboxypropyl]-acetamide.

The title compound was synthesized in the same manner as in Example 60. That is, the title compound in Example 98 (265 mg, 0.423 mmol) was reacted with 0.1N aqueous sodium hydroxide solution (10 mL) in THF (10 mL) to give 208 mg (84%) of the title compound as colorless crystals.

mp 134–136° C.; $^1$H-NMR (500 MHz, DMSO-$d_6$) δ 12.0 (brs, 1H), 9.54 (s, 1H), 8.90 (d, J=7.2 Hz, 1H), 8.79 (s, 1H), 7.35–7.15 (m, 9H), 4.96 (m, 1H), 4.44 (s, 2H), 3.14 (dd, J=14.2, 3.9 Hz, 1H), 2.75 (dd, J=14.2, 9.5 Hz, 1H), 2.70 (t, J=6.9 Hz, 2H), 2.50 (m, 2H), 2.31 (s, 3H); IR (KBr) 3700–2300, 1755, 1720, 1700, 1680, 1655, 1605, 1510 cm$^{-1}$ MS (SIMS, positive) m/z 585 (MH$^+$)

The compounds obtained in the above Examples are shown in Tables 1–7.

TABLE 1

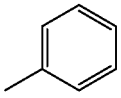

| Ex. No. | Z | M | R$^5$ | R$^6$ | R |
|---|---|---|---|---|---|
| 1 | CF$_3$ | N | 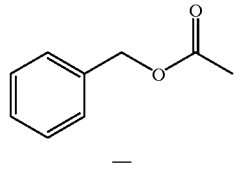 | — | 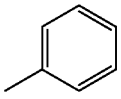 |
| 2 | CF$_3$ | N | 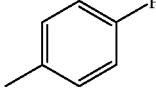 | — | H |
| 3 | CF$_3$ | N | 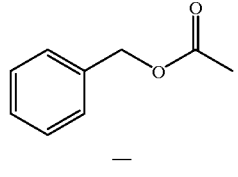 | — | 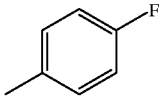 |
| 4 | CF$_3$ | N | 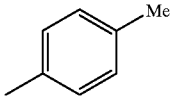 | — | H |
| 5 | CF$_3$ | N | 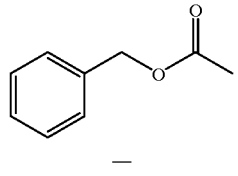 | — | 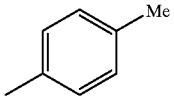 |
| 6 | CF$_3$ | N | (p-Me-C$_6$H$_4$-CH$_2$-) | — | H |

TABLE 1-continued
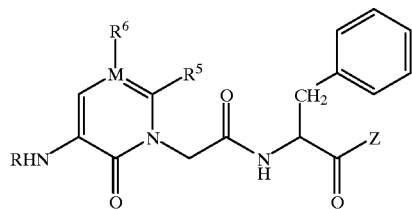
| Ex. No. | Z | M | R5 | R6 | R |
|---|---|---|---|---|---|
| 7 | CF$_3$ | N | 3-methylphenyl | — | benzyl acetate |
| 8 | CF$_3$ | N | 3-methylphenyl | — | H |
| 9 | CF$_2$C(O)NH-benzyl | N | 4-fluorophenyl | — | benzyl acetate |
| 10 | CF$_2$C(O)NH-benzyl | N | 4-fluorophenyl | — | H |
| 11 | CF$_3$ | C | H | phenethyl | benzyl acetate |
| 12 | CF$_3$ | C | H | phenethyl | H |
| 13 | CF$_3$ | C | — | 3-methylphenyl | benzyl acetate |

TABLE 1-continued

[Structure: pyrimidine/pyrimidinone ring with R⁶ on M, R⁵, RHN substituent, N-CH₂-C(O)-NH-CH(CH₂Ph)-C(O)-Z]

| Ex. No. | Z | M | R₅ | R⁶ | R |
|---|---|---|---|---|---|
| 14 | CF₃ | C | tolyl (methylphenyl) | H | H |
| 15 | CF₃ | C | H | tolyl (methylphenyl) | benzyl acetate (PhCH₂-O-C(O)-CH₃) |

TABLE 2

[Structure: same as above]

| Ex. No. | Z | M | R₅ | R⁶ | R |
|---|---|---|---|---|---|
| 16 | CF₃ | C | H | tolyl (methylphenyl) | H |
| 17 | CF₃ | C | H | H | benzyl acetate (PhCH₂-O-C(O)-CH₃) |
| 18 | CF₃ | C | H | H | H |
| 19 | CF₃ | N | H | — | benzyl acetate (PhCH₂-O-C(O)-CH₃) |
|  |  |  |  |  | — |

TABLE 2-continued

| Ex. No. | Z | M | R⁵ | R⁶ | R |
|---|---|---|---|---|---|
| 20 | CF₃ | N | H | — | H |
| 21 | CF₃ | N | Me | — | benzyl acetate group |
| 22 | CF₃ | N | Me | — | H |
| 23 | CF₃ | N | 2-methylphenyl | — | benzyl acetate group |
| 24 | CF₃ | N | 2-methylphenyl | — | H |
| 25 | CF₃ | N | 4-chlorophenyl | — | benzyl acetate group |
| 26 | CF₃ | N | 4-chlorophenyl | — | H |
| 27 | CF₃ | N | 4-methoxyphenyl | — | benzyl acetate group |
| 28 | CF₃ | N | 4-methoxyphenyl | — | H |

TABLE 2-continued

[Structure: pyrimidine ring with R6 on top N, R5 at position 2, RHN at position 5, C=O at position 6, N-CH2-C(=O)-NH-CH(CH2-phenyl)-C(=O)-Z]

| Ex. No. | Z | M | R5 | R6 | R |
|---------|-----|---|----|----|---|
| 29 | CF$_3$ | N | 4-hydroxy-3-methylphenyl | — | H |
| 30 | CF$_3$ | N | 4-nitro-3-methylphenyl | — | benzyl acetate group |

TABLE 3

[Structure: same pyrimidine framework as above]

| Ex. No. | Z | M | R$^5$ | R$^6$ | R |
|---------|-----|---|------|------|---|
| 31 | CF$_3$ | N | 4-nitro-3-methylphenyl | — | H |
| 32 | CF$_3$ | N | 4-amino-3-methylphenyl | — | benzyl acetate group |
| 33 | CF$_3$ | N | 4-amino-3-methylphenyl | — | H |

TABLE 3-continued

[Structure: pyrimidinone core with R6 on M, R5 substituent, N-CH2-C(O)-NH-CH(CH2Ph)-C(O)-Z, and RHN group on ring]

| Ex. No. | Z | M | R5 | R6 | R |
|---|---|---|---|---|---|
| 34 | CF$_3$ | N | 4-(NMe$_2$)-C$_6$H$_3$-Me | — | benzyl acetate |
| 35 | CF$_3$ | N | 4-(NMe$_2$)-C$_6$H$_3$-Me | — | H |
| 36 | CF$_3$ | N | 4-(NMe$_2$)-C$_6$H$_3$-Me | — | Me |
| 37 | CF$_3$ | N | 4-(NHAc)-C$_6$H$_3$-Me | — | benzyl acetate |
| 38 | CF$_3$ | N | 4-(NHAc)-C$_6$H$_3$-Me | — | H |
| 39 | CF$_3$ | N | 4-(NHSO$_2$CF$_3$)-C$_6$H$_3$-Me | — | benzyl acetate |
| 40 | CF$_3$ | N | 4-(NHSO$_2$CF$_3$)-C$_6$H$_3$-Me | — | H |
| 41 | CF$_3$ | N | 4-(NHCO$_2$i-Pr)-C$_6$H$_3$-Me | — | benzyl acetate |

TABLE 3-continued

[Structure: pyrimidinone core with R6, R5, RHN, N-CH2-C(O)-NH-CH(CH2Ph)-C(O)-Z]

| Ex. No. | Z | M | R5 | R6 | R |
|---|---|---|---|---|---|
| 42 | CF₃ | N | 4-(NHCO₂i-Pr)-phenyl-methyl | — | H |
| 43 | CF₃ | N | 3,5-dinitrophenyl-methyl | — | benzyl acetate (PhCH₂-O-C(O)-) |
| 44 | CF₃ | N | 3,5-dinitrophenyl-methyl | — | H |
| 45 | CF₃ | N | 3,5-diaminophenyl-methyl | — | benzyl acetate (PhCH₂-O-C(O)-) |

TABLE 4

[Structure: pyrimidinone core with R6, R5, RHN, N-CH2-C(O)-NH-CH(CH2Ph)-C(O)-Z]

| Ex. No. | Z | M | R5 | R6 | R |
|---|---|---|---|---|---|
| 46 | CF₃ | N | 3,5-diaminophenyl-methyl | — | H |

TABLE 4-continued

| Ex. No. | Z | M | R5 | R6 | R |
|---|---|---|---|---|---|
| 47 | CF₃ | N | 3-pyridyl | — | benzyl acetate |
| 48 | CF₃ | N | 3-pyridyl | — | H |
| 49 | CF₃ | N | 4-pyridyl | — | benzyl acetate |
| 50 | CF₃ | N | 4-pyridyl | — | H |
| 51 | CF₃ | N | 2-thienyl | — | benzyl acetate |
| 52 | CF₃ | N | 2-thienyl | — | H |
| 53 | CF₃ | N | phenyl | — | 4-(HO₂C)benzyl acetate |

TABLE 4-continued
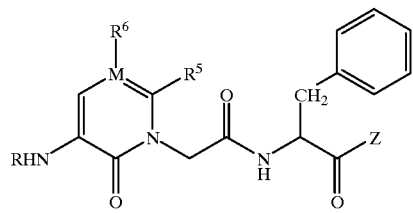
| Ex. No. | Z | M | R5 | R6 | R |
|---|---|---|---|---|---|
| 54 | CF$_3$ | N | phenyl | — | 3-(HO$_2$C)-C$_6$H$_4$-CH$_2$-O-C(O)-CH$_3$ |
| 55 | CF$_3$ | N | phenyl | — | iPr-O-C(O)-CH$_3$ |
| 56 | CF$_3$ | N | phenyl | — | MeO$_2$C-C(O)-CH$_3$ |
| 57 | CF$_3$ | N | phenyl | — | MeO$_2$C-CH$_2$-C(O)-CH$_3$ |
| 58 | CF$_3$ | N | phenyl | — | MeO$_2$C-(CH$_2$)$_2$-C(O)-CH$_3$ |
| 59 | CF$_3$ | N | phenyl | — | MeO$_2$C-(CH$_2$)$_3$-C(O)-CH$_3$ |
| 60 | CF$_3$ | N | phenyl | — | HO$_2$C-C(O)-CH$_3$ |

TABLE 5
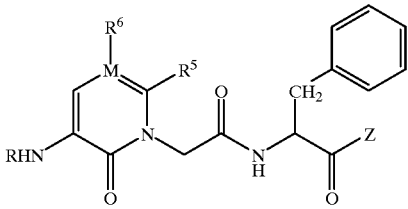
| Ex. No. | Z | M | R5 | R6 | R |
|---|---|---|---|---|---|
| 61 | CF₃ | N | 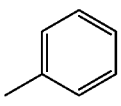 | — | 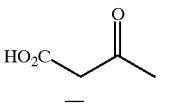 |
| 62 | CF₃ | N | 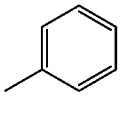 | — | 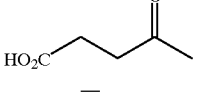 |
| 63 | CF₃ | N | 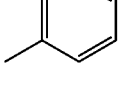 | — | 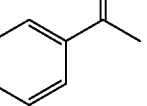 |
| 64 | CF₃ | N | 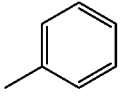 | — | 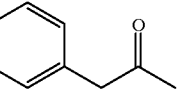 |
| 65 | CF₃ | N | 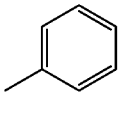 | — | 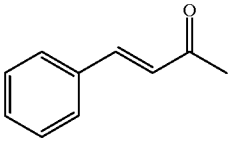 |
| 66 | CF₃ | N | 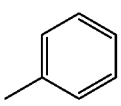 | — | 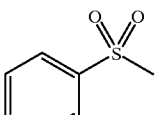 |
| 67 | CF₃ | N | 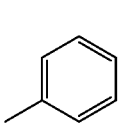 | — | 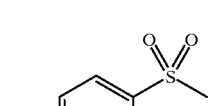 |
| 68 | CF₃ | N | 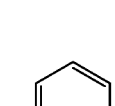 | — | 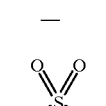 |

TABLE 5-continued
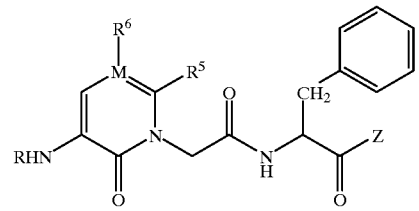
| Ex. No. | Z | M | R5 | R6 | R |
|---|---|---|---|---|---|
| 69 | CF$_3$ | N | 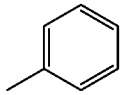 | — | 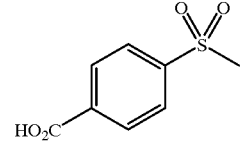 |
| 70 | CF$_3$ | C | 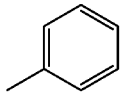 | H | 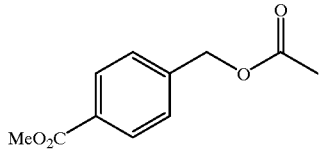 |
| 71 | CF$_3$ | C | 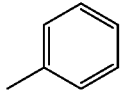 | H | 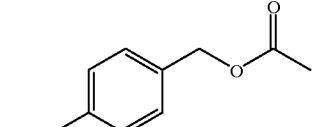 |
| 72 | CF$_3$ | C | 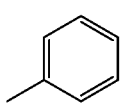 | H | 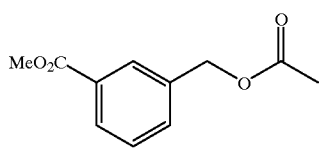 |
| 73 | CF$_3$ | C | 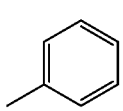 | H | 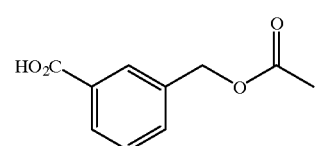 |
| 74 | CF$_3$ | C | H | H | 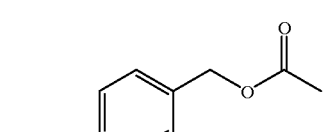 |
| 75 | CF$_3$ | C | H | H | 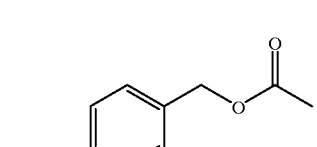 |

TABLE 6

| Ex. No. | Z | M | R5 | R6 | R |
|---|---|---|---|---|---|
| 76 | CF₃ | C | H | H | methyl 3-(acetoxymethyl)benzoate |
| 77 | CF₃ | C | H | H | 3-(acetoxymethyl)benzoic acid |
| 78 | CF₃ | N | phenyl (4-methyl) | — | acetone |
| 79 | CF₃ | N | 4-fluoro-methylphenyl | — | methyl 4-oxopentanoate |
| 80 | CF₃ | N | 4-fluoro-methylphenyl | — | 4-oxopentanoic acid |
| 81 | CF₃ | N | 3,5-dimethylphenyl | — | methyl 4-oxopentanoate |
| 82 | CF₃ | N | 3,5-dimethylphenyl | — | 4-oxopentanoic acid |
| 83 | CF₂C(O)NHCH₂CO₂H | N | 3,5-dimethylphenyl | — | H |

TABLE 6-continued
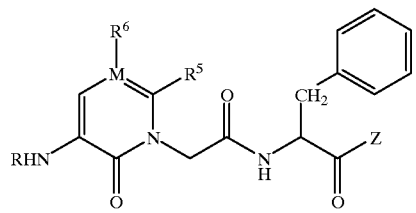
| Ex. No. | Z | M | R5 | R6 | R |
|---|---|---|---|---|---|
| 84 | CF$_2$-C(O)-NH-CH$_2$CH$_2$-CO$_2$H | N | 3-Me-phenyl | — | H |
| 85 | CF$_2$-C(O)-NH-CH$_2$-C(O)O-tBu | N | 3-Me-phenyl | — | H |
| 86 | CF$_2$-C(O)-NH-(3-CO$_2$tBu-phenyl) | N | 3-Me-phenyl | — | H |
| 87 | CF$_2$-C(O)-NH-(3-CO$_2$H-phenyl) | N | 3-Me-phenyl | — | H |
| 88 | CF$_2$-C(O)-NH-(4-CO$_2$H-phenyl) | N | 3-Me-phenyl | — | H |
| 89 | CF$_2$-C(O)-NH-CH$_2$-C(O)O-tBu | N | 4-F-phenyl | — | H |
| 90 | CF$_2$-C(O)-NH-CH$_2$-CO$_2$H | N | 4-F-phenyl | — | H |

TABLE 7

[Structure: pyrimidinone core with R6, R5, M, RHN, and linkage to -CH2-phenyl group with C(=O)Z]

| Ex. No. | Z | M | R⁵ | R⁶ | R |
|---|---|---|---|---|---|
| 91 | CF₂-C(=O)-NH-CH₂-CO₂Me | N | 4-F-phenyl | — | H |
| 92 | CF₂-C(=O)-NH-(3-substituted phenyl)-CO₂tBu | N | 4-F-phenyl | — | H |
| 93 | CF₂-C(=O)-NH-(3-substituted phenyl)-CO₂H | N | 4-F-phenyl | — | H |
| 94 | CF₂-C(=O)-OEt | N | 3-Me-phenyl | — | benzyl-OC(=O)-CH₃ |
| 95 | CF₂-C(=O)-OH | N | 3-Me-phenyl | — | benzyl-OC(=O)-CH₃ |
| 96 | CF₂-C(=O)-OEt | N | 3-Me-phenyl | — | H |
| 97 | CF₂-C(=O)-OH | N | 3-Me-phenyl | — | H |
| 98 | CF₂-C(=O)-OEt | N | 3-Me-phenyl | — | MeO₂C-CH₂CH₂-C(=O)-CH₃ |
| 99 | CF₂-C(=O)-OH | N | 3-Me-phenyl | — | HO₂C-CH₂CH₂-C(=O)-CH₃ |

EXPERIMENTAL EXAMPLE 1

Inhibitory Activity of the Inventive Compound on Human Heart Chymase

The effectiveness of the inhibitory activity of compound (I) of the present invention was evaluated based on the inhibitory activity on amidase activity of human heart chymase, which was determined as in the following.

The inhibitory activity was quantitatively determined through variation in fractional residual activity of the enzyme caused by the inventive compound in defined serial concentration (<×1, <×10, <×100-fold equivalents) relative to 5 nM chymase in the presence of synthetic substrate, succinyl-alanyl-alanyl-prolyl-phenylalanine-p-nitroanilide (final concentration 2.5 mM). The inhibitory effect was analyzed by least square regression of Easson-Stedman plot (Proc. Roy. Soc. B. 1936, 121, p. 141) utilizing bimolecular equilibrium reaction linearization formula. The inhibitory activity was evaluated by the apparent inhibitory constant (Kiapp) obtained by this analysis and inhibitory constant (Ki) calculated from final substrate concentration in the reaction mixture and Km values separately determined. The quantitative determination of initial rate of the enzyme reaction was spectrophotometrically detected in terms of an increased amount of p-nitroaniline at 405 nm produced by hydrolysis of the substrate. The chymase inhibitory activity of the compound of the present invention was calculated as ratio of residual activity in the presence of inhibitor relative to enzyme activity in the absence of inhibitor, and incorporation of the determination values was completed at a level less than initial rate guarantee absorbance at a concentration of the substrate used for the enzyme, after which analysis was performed.

The reaction mixture consisted of an $Na_2B_4O_7$ (100 mM)-$KH_2PO_4$ (50 mM) buffer (pH 9.0, 120 µl) containing 0.1% Triton-X100, the inventive compound dissolved in 20 µl of 10% dimethyl sulfoxide (DMSO), 10% bovine serum albumin dissolved in 20 µl of the same buffer, substrate dissolved in 20 µl of DMSO, and 20 µl of chymase, thus amounting to 200 µl in total.

Starting with the absorbance immediately after addition of the enzyme, increases in absorbance were recorded as a progressive curve taken precisely at equal time intervals.

From the above data, the difference between absorbances at completion of the reaction and immediately after addition was used to quantitatively determine the residual activity of the sample added with the inhibitor relative to a control wherein the inhibitor was not added. Alternatively, reaction rates of the control and the sample added with the inhibitor were calculated for certain time period (≧20 min) with successive shift (every 10 to 30 minutes) of the period, and the residual activity ratio was quantitatively determined and analyzed from the respective reaction rates averaged through the entire reaction time.

The inhibitory activity against human leukocyte elastase was determined using N-methoxysuccinyl-alanyl-alanyl-prolyl-valine-p-nitroanilide as a substrate and 0.1 M Tris-HCl (pH 8.0) containing 20 mM $CaCl_2$ and 0.1% Tween 80 as a buffer, wherein other compositions and method were the same as above.

The results of human heart chymase inhibitory activity test of representative compound (I) of the present invention are shown in Table 8.

TABLE 8

| compound | $K^i$ (µM) |
|---|---|
| Example 2 | 7.2 |
| Example 3 | 5.6 |
| Example 4 | 4.1 |
| Example 5 | 8.7 |
| Example 6 | 7.0 |
| Example 7 | 4.8 |
| Example 8 | 5.9 |
| Example 10 | 7.2 |
| Example 29 | 3.9 |
| Example 31 | 10.0 |
| Example 32 | 8.4 |
| Example 33 | 3.0 |
| Example 45 | 4.7 |
| Example 46 | 1.9 |
| Example 47 | 13.0 |
| Example 48 | 7.7 |
| Example 50 | 8.3 |
| Example 52 | 7.4 |
| Example 53 | 9.3 |
| Example 54 | 3.3 |
| Example 58 | 2.5 |
| Example 61 | 2.3 |
| Example 62 | 1.8 |
| Example 71 | 10.0 |
| Example 73 | 4.8 |
| Example 81 | 2.9 |
| Example 86 | 2.9 |
| Example 99 | 10.0 |

On the other hand, the inhibitory activity against human leukocyte elastase was >$10^5$ µM for every compound.

From the above results, it is evident that the compound (I) of the present invention does not inhibit human leukocyte elastase at all, but strongly inhibits human heart chymase.

FORMULATION EXAMPLE 1 tablets

| | |
|---|---|
| (1) compound (I) of the invention | 10 mg |
| (2) fine particle No. 209 for direct compression (manufactured by Fuji Kagaku) | 46.6 mg |
|     magnesium aluminate metasilicate | 20% |
|     corn starch | 30% |
|     lactose | 50% |
| (3) crystalline cellulose | 24.0 mg |
| (4) calcium carboxylmethylcellulose | 4.0 mg |
| (5) magnesium stearate | 0.4 mg |

(1), (3) and (4) were respectively passed through a 100 mesh sieve in advance. These (1), (3), (4) and (2) were respectively dried to certain water contents, and mixed in a mixer at the above-mentioned weight ratios. To the entirely homogeneous powder mixture was added (5) and the mixture was mixed for a short time (30 sec). The mixed powder was compressed using a pounder (6.3 mm φ, 6.0 mm R) to give tablets weighing 85 mg per tablet.

These tablets may be coated using an enteric film coating agent such as polyvinylacetal diethylaminoacetate) or edible colorant, as necessary.

FORMULATION EXAMPLE 2
capsules

| | |
|---|---|
| (1) compound (I) of the invention | 50 g |
| (2) lactose | 935 g |
| (3) magnesium stearate | 15 g |

The above-mentioned ingredients were weighed and homogeneously mixed. The mixed powder was filled in hard gelatin capsules by 200 mg each.

FORMULATION EXAMPLE 3
injections

| | |
|---|---|
| (1) hydrochloride of compound (I) of the invention | 5 mg |
| (2) sucrose | 100 mg |
| (3) physiological saline | 10 ml |

The mixed solution of the above ingredients was passed through a membrane filter, and again sterilized by filtration. The filtered solution was aseptically dispensed into-vials, and the vials were sealed after filling nitrogen gas, to give intravenous injections.

The heterocyclic amide compounds and pharmacologically acceptable salts thereof of the present invention have superior inhibitory activity against chymase groups in mammals inclusive of human, and can be administered orally or parenterally. Therefore, they are useful as chymase inhibitors and can be effective for the prophylaxis and treatment of various diseases caused by chymase, such as those caused by angiotensin II.

What is claimed is:

1. A heterocyclic amide compound of the formula (I)

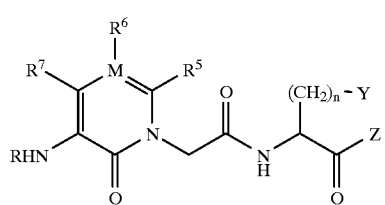

(I)

wherein
R is hydrogen, —CHO, —$CONH_2$, —$COR^1$, —$COOR^1$, —$CONHOR^1$, —$CONHR^1$, —$CONR^1R^{11}$, —$CONHSO_2R^1$, —$COSR^1$, —$COCOR^2$, —$COCOOR^2$, —$CONHCOOR^2$, —$COCONR^3R^4$, —$CSXR^1$, —$SO_2WR^1$, —$SO_2NR^1R^{11}$, or —$SO_2E$ wherein
$R^1$ and $R^{11}$ may be the same or different and each is independently substituted or unsubstituted alkyl, cycloalkyl, cycloalkylalkyl, aryl, arylalkyl, heteroaryl, heteroarylalkyl, heterocycle or heterocyclealkyl, $R^2$, $R^3$ and $R^4$ may be the same or different and each is independently hydrogen, or substituted or unsubstituted alkyl or arylalkyl, [—$NR^3R^4$ may, in combination, show heterocycle] and $R^3$ and $R^4$ may combine with the nitrogen to which they are attached to form a heterocycle, X is a direct bond, —NH—, —O— or —S—, W is a direct bond, —NH—, —NHCO—, —NHCOO— or —NHCONH—, and E is hydroxyl or amino;

$R^5$, $R^6$ and $R^7$ may be the same or different and each is independently hydrogen or substituted or unsubstituted alkyl, or one of $R^5$, $R^6$ and $R^7$ is substituted or unsubstituted aryl, arylalkyl, arylalkenyl, heteroaryl, heteroarylalkyl or heteroarylalkenyl and the rest are hydrogen;

M is a carbon or nitrogen, provided that when M is a nitrogen, $R^6$ is void;

Y is substituted or unsubstituted cycloalkyl, aryl or heteroaryl;

Z is —$CF_2R^8$, —$CF_2CONR^9R^{10}$, —$CF_2COOR^9$, $COOR^9$ or —$CONR^9R^{10}$ wherein
$R^8$ is hydrogen, halogen, alkyl, perfluoroalkyl, aminoalkyl, alkylaminoalkyl, dialkylaminoalkyl, alkoxyalkyl, hydroxyalkyl, or substituted or unsubstituted aryl, arylalkyl, arylalkenyl, heteroaryl, heteroarylalkyl or heteroarylalkenyl, $R^9$ and $R^{10}$ may be the same or different and each is independently hydrogen, or substituted or unsubstituted alkyl, alkenyl, cycloalkyl, cycloalkylalkyl, heterocyclealkyl, aryl, arylalkyl, arylalkenyl, heteroaryl, heteroarylalkyl or heteroarylalkenyl, and [—$NR^9R^{10}$ may, in combination, show heterocylcle] and $R^9$ and $R^{10}$ may combine with the nitrogen to which they are attached to form a heterocycle; and n is 0 or 1; or a pharmacologically acceptable salt thereof.

2. The heterocyclic amide compound of claim 1, wherein, in the formula (I), Y is substituted or unsubstituted aryl, or a pharmacologically acceptable salt thereof.

3. The heterocyclic amide compound of claim 1, wherein, in the formula (I), Z is —$CF_2R^8$ or —$CF_2CONR^9R^{10}$, or a pharmacologically acceptable salt thereof.

4. The heterocyclic amide compound of claim 1, wherein, in the formula (I), one of $R^5$, $R^6$ and $R^7$ is substituted or unsubstituted aryl and the rest are hydrogen, provided that when M is nitrogen, $R^6$ is void, or a pharmacologically acceptable salt thereof.

5. A compound of the formula (II)

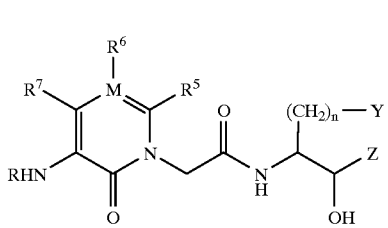

(II)

wherein
R is hydrogen, —CHO, —$CONH_2$, —$COR^1$, —$COOR^1$, —$CONHOR^1$, —$CONHR^1$, —$CONR^1R^{11}$, —$CONHSO_2R^1$, —$COSR^1$, —$COCOR^2$, $COCOOR^2$, —$CONHCOOR^2$, —$COCONR^3R^4$, —$CSXR^1$, —$SO_2WR^1$, —$SO_2NR^1R^{11}$, or —$SO_2E$, wherein
$R^1$ and $R^{11}$ may be the same or different and each is independently substituted or unsubstituted alkyl, cycloalkyl, cycloalkylalkyl, aryl, arylalkyl, heteroaryl, heteroarylalkyl, heterocycle or heterocyclealkyl, $R^2$, $R^3$ and $R^4$ may be the same or different and each is independently hydrogen, or substituted or unsubstituted alkyl or arylalkyl,

[—NR$^3$R$^4$ may, in combination, show heterocycle] and R$^3$ and R$^4$ may combine with the nitrogen to which they are attached to form a heterocycle, X is a direct bond, —NH—, —O— or —S—, W is a direct bond, —NH—, —NHCO—, —NHCOO— or —NHCONH—, and E is hydroxyl or amino;

R$^5$, R$^6$ and R$^7$ may be the same or different and each is independently hydrogen or substituted or unsubstituted alkyl, or one of R$^5$, R$^6$ and R$^7$ is substituted or unsubstituted aryl, arylalkyl, arylalkenyl, heteroaryl, heteroarylalkyl or heteroarylalkenyl and the rest are hydrogen;

M is a carbon or nitrogen, provided that when M is a nitrogen, R$^6$ is void;

Y is substituted or unsubstituted cycloalkyl, aryl or heteroaryl;

Z is —CF$_2$R$^8$, —CF$_2$CONR$^9$R$^{10}$, —CF$_2$COOR$^9$, COOR$^9$ or —CONR$^9$R$^{10}$ wherein R$^8$ is hydrogen, halogen, alkyl, perfluoroalkyl, aminoalkyl, alkylaminoalkyl, dialkylaminoalkyl, alkoxyalkyl, hydroxyalkyl, or substituted or unsubstituted aryl, arylalkyl, arylalkenyl, heteroaryl, heteroarylalkyl or heteroarylalkenyl, R$^9$ and R$^{10}$ may be the same or different and each is independently hydrogen, or substituted or unsubstituted alkyl, alkenyl, cycloalkyl, cycloalkylalkyl, heterocyclealkyl, aryl, arylalkyl, arylalkenyl, heteroaryl, heteroarylalkyl or heteroarylalkenyl, and [—NR$^9$R$^{10}$ may, in combination, show heterocylcle] and R$^9$ and R$^{10}$ may combine with the nitrogen to which they are attached to form a heterocycle; and n is 0 or 1.

6. The heterocyclic amide compound of claim 2, wherein, in the formula (I), Z is —CF$_2$R$^8$ or —CF$_2$CONR$^9$R$^{10}$, or a pharmacologically acceptable salt thereof.

7. The heterocyclic amide compound of claim 2, wherein, in the formula (I), one of R$^5$, R$^6$, and R$^7$ is substituted or unsubstituted aryl and the rest are hydrogen, provided that when M is nitrogen, R$^6$ is void, or a pharmacologically acceptable salt thereof.

8. The heterocyclic amide compound of claim 3, wherein, in the formula (I), one of R$^5$, R$^6$, and R$^7$ is substituted or unsubstituted aryl and the rest are hydrogen, provided that when M is nitrogen, R$^6$ is void, or a pharmacologically acceptable salt thereof.

9. The heterocyclic amide compound of claim 1, wherein, in the formula (I), M is carbon.

10. The heterocyclic amide compound of claim 1, wherein, in the formula (I), M is nitrogen.

11. The heterocyclic amide compound of claim 5, wherein, in the formula (I), M is carbon.

12. The heterocyclic amide compound of claim 5, wherein, in the formula (I), M is nitrogen.

13. A pharmaceutical composition comprising a therapeutically effective amount of the heterocyclic amide compound of any one of claims 1 to 4, and 6 to 12 or a pharmacologically acceptable salt thereof, and a pharmacologically acceptable carrier.

14. The pharmaceutical composition of claim 13, which is a chymase inhibitor containing a chymase inhibiting effective amount of the heterocyclic amide compound.

\* \* \* \* \*